US006277381B1

(12) United States Patent
Reed et al.

(10) Patent No.: US 6,277,381 B1
(45) Date of Patent: Aug. 21, 2001

(54) **COMPOUNDS AND METHODS FOR THE DIAGNOSIS AND TREATMENT OF *EHRLICHIA* INFECTION**

(75) Inventors: Steven G. Reed, Bellevue; Michael J. Lodes, Seattle; Raymond L. Houghton, Bothell; Patricia D. McNeill, Des Moines, all of WA (US)

(73) Assignee: Corixa Corporation, Seattle, WA (US)

(*) Notice: Subject to any disclaimer, the term of this patent is extended or adjusted under 35 U.S.C. 154(b) by 0 days.

(21) Appl. No.: 09/295,028

(22) Filed: Apr. 20, 1999

Related U.S. Application Data

(63) Continuation-in-part of application No. 09/159,469, filed on Sep. 23, 1998, which is a continuation-in-part of application No. 09/106,582, filed on Jun. 29, 1998, which is a continuation-in-part of application No. 08/975,762, filed on Nov. 20, 1997, which is a continuation-in-part of application No. 08/821,324, filed on Mar. 21, 1997.

(51) Int. Cl.[7] .............................. A61K 39/02; C12Q 1/68; C07H 21/04
(52) U.S. Cl. .................... 424/234.1; 435/6; 536/23.7; 536/24.32; 536/24.33
(58) Field of Search .................... 424/234.1; 435/6; 536/23.7, 24.32, 24.33

(56) References Cited

FOREIGN PATENT DOCUMENTS

| WO 96/39484 | 12/1996 | (WO) . |
| WO 98/14584 | 4/1998 | (WO) . |
| WO 98/42740 | 10/1998 | (WO) . |
| WO 98/49313 | 11/1998 | (WO) . |

OTHER PUBLICATIONS

Asanovich et al., "Partial Characterization of Cloned Genes Encoding Immunoreactive Proteins of *Ehrlichia equi* and the Agent of Human Granulocytic Ehrlichiosis," *Abstracts of the General Meeting of the American Society for Microbiology*: Abstract No. D–22, 1996.

Dumler et al., "Serologic Cross–Reactions among *Ehrlichia equi, Ehrlichia phagocytophila*, and Human Granulocytic Ehrlichia," *Journal of Clinical Microbiology* 33(11): 1098–1103, 1995.

Palmer et al., "The Immunoprotective *Anaplasma marginale* Major Surface Protein 2 Is Encoded by a Polymorphic Multigene Family," *Infection And Immunity* 62(9): 3808–3816, 1994.

Magnarelli et al., "Coexistence of Antibodies to Tick–Borne Pathogens of Babesiosis Ehrlichiosis, and Lyme Borreliosis in Human Sera," *Journal Of Clinical Microbiology* 33(11): 3054–3057, 1995.

*Primary Examiner*—Rodney P Swartz
(74) *Attorney, Agent, or Firm*—Seed Intellectual Property Law Group PLLC

(57) ABSTRACT

Compounds and methods for the diagnosis and treatment of Ehrlichia infection, in particular human granulocytic ehrlichiosis, are disclosed. The compounds provided include polypeptides that contain at least one antigenic portion of an Ehrlichia antigen and DNA sequences encoding such polypeptides. Pharmaceutical compositions an vaccines comprising such polypeptides or DNA sequences are also provided. Diagnostic kits containing such polypeptides or DNA sequences and a suitable detection reagent may be used for the detection of Ehrlichia infection in patients and biologiacal samples. Antibodies directed against such polypeptides are also provided.

10 Claims, 5 Drawing Sheets

SEQUENCE LISTING

<160> NUMBER OF SEQ ID NOS: 85

<210> SEQ ID NO 1
<211> LENGTH: 1345
<212> TYPE: DNA
<213> ORGANISM: Ehrlichia sp.

<400> SEQUENCE: 1

```
ttgagcttga gattggttac gagcgcttca agaccaaggg tattagagat agtggtagta      60
aggaagatga agctgataca gtatatctac tagctaagga gttagcttat gatgttgtta     120
ctggtcagac tgataacctt gccgctgctc ttgccaaaac ctccggtaag gatattgttc     180
agtttgctaa ggcggtggag atttctcatt ccgagattga tggcaaggtt tgtaagacga     240
agtcggcggg aactggaaaa aatccgtgtg atcatagcca aaagccgtgt agtacgaatg     300
cgtattatgc gaggagaacg cagaagagta ggagttcggg aaaaacgtct ttatgcgggg     360
acagtgggta tagcgggcag gagctaataa cgggtgggca ttatagcagt ccaagcgtat     420
tccggaattt tgtcaaagac acactacaag gaaatggtag tgagaactgg cctacatcta     480
ctggagaagg aagtgagagt aacgacaacg ccatagccgt tgctaaggac ctagtaaatg     540
aacttactcc tgaagaacga accatagtgg ctgggttact tgctaaaatt attgaaggaa     600
gcgaggttat tgagattagg gccatctctt cgacttcagt tacaatgaat atttgctcag     660
atatcacgat aagtaatatc ttaatgccgt atgtttgtgt tggtccaggg atgagctttg     720
ttagtgttgt tgatggtcac actgctgcaa agtttgcata tcggttaaag gcaggtctga     780
gttataaatt ttcgaaagaa gttacagctt ttgcaggtgg tttttaccat cacgttatag     840
gagatggtgt ttatgatgat ctgccattgc ggcatttatc tgatgatatt agtcctgtga     900
aacatgctaa ggaaaccgcc attgctagat tcgtcatgag gtactttggc ggggaatttg     960
gtgttaggct cgcttttaa ggttgcgacc taaaagcact tagctcgcct tcactccccc    1020
```

-continued

| | |
|---|---|
| ttaagcaata tgatgcacat ttgttgccct acaaatctaa tataaggttt gttgcctata | 1080 |
| ctcgtgccga attcggcacg aggaggaagc tgaactcacc catcagtctc tctcatccgt | 1140 |
| tggccacctg ctgtccccac ccacccacca aactggtgct tttaatggaa tcagctttaa | 1200 |
| aaagaaaaaa atcctccaag taacaaagca ccctataatt attccgcagc tccttgtcct | 1260 |
| cggtaatttt aggcttgtgc tgctatcatt acacattaca tggagttagg gagtcatagc | 1320 |
| tcttgtgtgg ccaatcagtg ataca | 1345 |

<210> SEQ ID NO 2
<211> LENGTH: 1132
<212> TYPE: DNA
<213> ORGANISM: Ehrlichia sp.

<400> SEQUENCE: 2

| | |
|---|---|
| atttctatat tggtttggat tacagtccag cgtttagcaa gataagagat tttagtataa | 60 |
| gggagagtaa cggagagaca aaggcagtat atccatactt aaaggatgga aagagtgtaa | 120 |
| agctagagtc acacaagttt gactggaaca cacctgatcc tcggattggg tttaaggaca | 180 |
| acatgcttgt agctatggaa ggtagtgttg gttatggtat tggtggtgcc agggttgagc | 240 |
| ttgagattgg ttacgagcgc ttcaagacca agggtattag agatagtggt agtaaggaag | 300 |
| atgaagctga tacagtatat ctactagcta aggagttagc ttatgatgtt gttactggac | 360 |
| agactgataa ccttgctgct gctcttgcta agacctcggg gaaagacatc gttcagtttg | 420 |
| ctaaggcggt tggggtttct catcctagta ttgatgggaa ggtttgtaag acgaaggcgg | 480 |
| atagctcgaa gaaatttccg ttatatagtg acgaaacgca cacgaagggg gcaaatgagg | 540 |
| ggagaacgtc tttgtgcggt gacaatggta gttctacgat aacaaccagt ggtacgaatg | 600 |
| taagtgaaac tgggcaggtt tttagggatt ttatcagggc aacgctgaaa gaggatggta | 660 |
| gtaaaaactg gccaacttca agcggcacgg gaactccaaa acctgtcacg aacgacaacg | 720 |
| ccaaagccgt agctaaagac ctagtacagg agctaacccc tgaagaaaaa accatagtag | 780 |
| cagggttact agctaagact attgaagggg gtgaagttgt tgagatcagg gcggtttctt | 840 |
| ctacttccgt aatggtcaat gcttgttatg atcttcttag tgaaggttta ggtgttgttc | 900 |
| cttatgcttg tgttggtctc ggtggtaact tcgtgggcgt ggttgatgga attcattaca | 960 |
| caaaccatct ttaactctga ataccctagt taaggtaagt gaagtaacta ggcaaattag | 1020 |
| tgctgcacca ctcgtgaaac aaactacgat cagcgattca ccatacttag taggtccgta | 1080 |
| cagtggcttt acgctcttac ccatcatgaa aaatacttgc tatctaggaa tc | 1132 |

<210> SEQ ID NO 3
<211> LENGTH: 554
<212> TYPE: DNA
<213> ORGANISM: Ehrlichia sp.

<400> SEQUENCE: 3

| | |
|---|---|
| ctactagcta aggagttagc ttatgatgtt gttactgggc agactgataa ccttgctgct | 60 |
| gctcttgcca agacttctgg taaagatatt gttcagtttg ctaagactct taatatttct | 120 |
| cactctaata tcgatgggaa ggtttgtagg agggaaaagc atgggagtca aggttttgact | 180 |
| ggaaccaaag caggttcgtg tgatagtcag ccacaaacgg cgggtttcga ttccatgaaa | 240 |
| caaggtttga tggcagcttt aggcgaacaa ggcgctgaaa agtggcccaa aattaacaat | 300 |
| ggtggccacg caacaattta tagtagtagc gcaggtccag gaaatgcgta tgctagagat | 360 |
| gcatctacta cggtagctac agacctaaca aagctcacta ctgaagaaaa aaccatagta | 420 |

```
gcagggttac tagctagaac tattgaaggg ggtgaagttg ttgagattag ggcagtttct        480
tctacttctg tgatggttaa tgcttgttat gatcttctta gtgaaggttt aggtgttgta        540
ccttatgctt gtgt                                                          554

<210> SEQ ID NO 4
<211> LENGTH: 559
<212> TYPE: DNA
<213> ORGANISM: Ehrlichia sp.

<400> SEQUENCE: 4
atgctgtgaa aattactaac tccactatcg atgggaaggt ttgtaatggt agtagagaga         60 agggaatag tgctgggaac aacaacagtg ctgtggctac ctacgcgcag actcacacag         120
cgaatacatc aacgtcacag tgtagcggtc tagggaccac tgttgtcaaa caaggttatg        180
gaagtttgaa taagtttgtt agcctgacgg gggttggtga aggtaaaaat tggcctacag        240
gtaagataca cgacggtagt agtggtgtca agatggtgaa acagaacggg aatgccaaag        300
ccgtagctaa agacctagta gatcttaatc gtgacgaaaa aaccatagta gcaggattac        360
tagctaaaac tattgaaggg ggtgaagttg ttgagatcag ggcggtttct tctacttctg        420
tgatggttaa tgcttgttat gatcttctta gtgaaggttt aggcgttgtt ccttacgctt        480
gtgtcggtct cggaggtaac ttcgtgggcg ttgttgatgg gcatatcact cctaagcttg        540
cttatagatt aaaggctgg                                                    559

<210> SEQ ID NO 5
<211> LENGTH: 201
<212> TYPE: DNA
<213> ORGANISM: Ehrlichia sp.

<400> SEQUENCE: 5
agcgcttcaa gaccaagggt attagagata gtggtagtaa ggaagatgaa gctgatacag         60
tatatctact agctaaggag ttagcttatg atgttgttac tggacagact gataaccttg        120
ccgctgctct tgctaaaacc tcggggaaag actttgttca gtttgctaag gccgtggaga        180
tttctaattc tacgattggg g                                                  201

<210> SEQ ID NO 6
<211> LENGTH: 467
<212> TYPE: DNA
<213> ORGANISM: Ehrlichia sp.

<400> SEQUENCE: 6
ggtatatcga tagcctacgt agtcactcct tattattaaa aaggaagacc aagggtatta         60
gagatagtgg aagtaaggaa gatgaagcag atacagtata tctactagct aaggagttag        120
cttatgatgt tgttactggg cagactgata accttgccgc tgctcttgcc aaaacctccg        180
gtaaggactt tgttaaattt gccaatgctg ttgttggaat ttctcacccc gatgttaata        240
agaaggtttg tgcgacgagg aaggacagtg gtggtactag atatgcgaag tatgctgcca        300
cgactaataa gagcagcaac cctgaaacct cactgtgtgg agacgaaggt ggctcgagcg        360
gcacgaataa tacacaagag tttcttaagg aatttgtagc ccaaacccta gtagaaaatg        420
aaagtaaaaa ctggcctact tcaagcggga ctgggttgaa gactaac                     467

<210> SEQ ID NO 7
<211> LENGTH: 530
<212> TYPE: DNA
```

<213> ORGANISM: Ehrlichia sp.

<400> SEQUENCE: 7

```
aagatgaagc tgatacagta tatctactgg ctaaggagtt agcttatgat gttgttactg      60
gacagactga taagcttact gctgctcttg ctaagacctc cgggaaggac tttgttcagt     120
ttgctaaggc ggttgggtt tctcatccta atatcgatgg gaaggtttgt aagactacgc     180
tagggcacac gagtgcggat agctacggtg tgtatgggga gttaacaggc caggcgagtg     240
cgagtgagac atcgttatgt ggtggtaagg gtaaaaatag tagtggtggt ggagctgctc     300
ccgaagtttt aagggacttt gtaaagaaat ctctgaaaga tgggggccaa aactggccaa     360
catctagggc gaccgagagt tcacctaaga ctaaatctga aactaacgac aatgcaaaag     420
ctgtcgctaa agacctagta gaccttaatc ctgaagaaaa aaccatagta gcagggttac     480
tagctaaaac tattgaaggt ggggaagttg tagaaatcag agcagtttct     530
```

<210> SEQ ID NO 8
<211> LENGTH: 325
<212> TYPE: PRT
<213> ORGANISM: Ehrlichia sp.

<400> SEQUENCE: 8

Glu Leu Glu Ile Gly Tyr Glu Arg Phe Lys Thr Lys Gly Ile Arg Asp
1               5                   10                  15

Ser Gly Ser Lys Glu Asp Glu Ala Asp Thr Val Tyr Leu Leu Ala Lys
            20                  25                  30

Glu Leu Ala Tyr Asp Val Val Thr Gly Gln Thr Asp Asn Leu Ala Ala
        35                  40                  45

Ala Leu Ala Lys Thr Ser Gly Lys Asp Ile Val Gln Phe Ala Lys Ala
    50                  55                  60

Val Glu Ile Ser His Ser Glu Ile Asp Gly Lys Val Cys Lys Thr Lys
65                  70                  75                  80

Ser Ala Gly Thr Gly Lys Asn Pro Cys Asp His Ser Gln Lys Pro Cys
                85                  90                  95

Ser Thr Asn Ala Tyr Tyr Ala Arg Arg Thr Gln Lys Ser Arg Ser Ser
            100                 105                 110

Gly Lys Thr Ser Leu Cys Gly Asp Ser Gly Tyr Ser Gly Gln Glu Leu
        115                 120                 125

Ile Thr Gly Gly His Tyr Ser Ser Pro Ser Val Phe Arg Asn Phe Val
    130                 135                 140

Lys Asp Thr Leu Gln Gly Asn Gly Ser Glu Asn Trp Pro Thr Ser Thr
145                 150                 155                 160

Gly Glu Gly Ser Glu Ser Asn Asp Asn Ala Ile Ala Val Ala Lys Asp
                165                 170                 175

Leu Val Asn Glu Leu Thr Pro Glu Glu Arg Thr Ile Val Ala Gly Leu
            180                 185                 190

Leu Ala Lys Ile Ile Glu Gly Ser Glu Val Ile Glu Ile Arg Ala Ile
        195                 200                 205

Ser Ser Thr Ser Val Thr Met Asn Ile Cys Ser Asp Ile Thr Ile Ser
    210                 215                 220

Asn Ile Leu Met Pro Tyr Val Cys Val Gly Pro Gly Met Ser Phe Val
225                 230                 235                 240

Ser Val Val Asp Gly His Thr Ala Ala Lys Phe Ala Tyr Arg Leu Lys
                245                 250                 255

Ala Gly Leu Ser Tyr Lys Phe Ser Lys Glu Val Thr Ala Phe Ala Gly

```
                260                 265                 270
Gly Phe Tyr His His Val Ile Gly Asp Gly Val Tyr Asp Asp Leu Pro
            275                 280                 285

Leu Arg His Leu Ser Asp Asp Ile Ser Pro Val Lys His Ala Lys Glu
        290                 295                 300

Thr Ala Ile Ala Arg Phe Val Met Arg Tyr Phe Gly Gly Glu Phe Gly
305                 310                 315                 320

Val Arg Leu Ala Phe
                325

<210> SEQ ID NO 9
<211> LENGTH: 323
<212> TYPE: PRT
<213> ORGANISM: Ehrlichia sp.

<400> SEQUENCE: 9

Phe Tyr Ile Gly Leu Asp Tyr Ser Pro Ala Phe Ser Lys Ile Arg Asp
  1               5                  10                  15

Phe Ser Ile Arg Glu Ser Asn Gly Glu Thr Lys Ala Val Tyr Pro Tyr
             20                  25                  30

Leu Lys Asp Gly Lys Ser Val Lys Leu Glu Ser His Lys Phe Asp Trp
         35                  40                  45

Asn Thr Pro Asp Pro Arg Ile Gly Phe Lys Asp Asn Met Leu Val Ala
     50                  55                  60

Met Glu Gly Ser Val Gly Tyr Gly Ile Gly Gly Ala Arg Val Glu Leu
 65                  70                  75                  80

Glu Ile Gly Tyr Glu Arg Phe Lys Thr Lys Gly Ile Arg Asp Ser Gly
                 85                  90                  95

Ser Lys Glu Asp Glu Ala Asp Thr Val Tyr Leu Leu Ala Lys Glu Leu
            100                 105                 110

Ala Tyr Asp Val Val Thr Gly Gln Thr Asp Asn Leu Ala Ala Ala Leu
        115                 120                 125

Ala Lys Thr Ser Gly Lys Asp Ile Val Gln Phe Ala Lys Ala Val Gly
    130                 135                 140

Val Ser His Pro Ser Ile Asp Gly Lys Val Cys Lys Thr Lys Ala Asp
145                 150                 155                 160

Ser Ser Lys Lys Phe Pro Leu Tyr Ser Asp Glu Thr His Thr Lys Gly
                165                 170                 175

Ala Asn Glu Gly Arg Thr Ser Leu Cys Gly Asp Asn Gly Ser Ser Thr
            180                 185                 190

Ile Thr Thr Ser Gly Thr Asn Val Ser Glu Thr Gly Gln Val Phe Arg
        195                 200                 205

Asp Phe Ile Arg Ala Thr Leu Lys Glu Asp Gly Ser Lys Asn Trp Pro
    210                 215                 220

Thr Ser Ser Gly Thr Gly Thr Pro Lys Pro Val Thr Asn Asp Asn Ala
225                 230                 235                 240

Lys Ala Val Ala Lys Asp Leu Val Gln Glu Leu Thr Pro Glu Glu Lys
                245                 250                 255

Thr Ile Val Ala Gly Leu Leu Ala Lys Thr Ile Glu Gly Gly Glu Val
            260                 265                 270

Val Glu Ile Arg Ala Val Ser Ser Thr Ser Val Met Val Asn Ala Cys
        275                 280                 285

Tyr Asp Leu Leu Ser Glu Gly Leu Gly Val Val Pro Tyr Ala Cys Val
    290                 295                 300
```

```
Gly Leu Gly Gly Asn Phe Val Gly Val Val Asp Gly Ile His Tyr Thr
305                 310                 315                 320

Asn His Leu
```

```
<210> SEQ ID NO 10
<211> LENGTH: 185
<212> TYPE: PRT
<213> ORGANISM: Ehrlichia sp.

<400> SEQUENCE: 10

Leu Leu Ala Lys Glu Leu Ala Tyr Asp Val Val Thr Gly Gln Thr Asp
1               5                   10                  15

Asn Leu Ala Ala Ala Leu Ala Lys Thr Ser Gly Lys Asp Ile Val Gln
            20                  25                  30

Phe Ala Lys Thr Leu Asn Ile Ser His Ser Asn Ile Asp Gly Lys Val
        35                  40                  45

Cys Arg Arg Glu Lys His Gly Ser Gln Gly Leu Thr Gly Thr Lys Ala
    50                  55                  60

Gly Ser Cys Asp Ser Gln Pro Gln Thr Ala Gly Phe Asp Ser Met Lys
65                  70                  75                  80

Gln Gly Leu Met Ala Ala Leu Gly Glu Gln Gly Ala Glu Lys Trp Pro
                85                  90                  95

Lys Ile Asn Asn Gly Gly His Ala Thr Ile Tyr Ser Ser Ser Ala Gly
            100                 105                 110

Pro Gly Asn Ala Tyr Ala Arg Asp Ala Ser Thr Thr Val Ala Thr Asp
        115                 120                 125

Leu Thr Lys Leu Thr Thr Glu Glu Lys Thr Ile Val Ala Gly Leu Leu
    130                 135                 140

Ala Arg Thr Ile Glu Gly Gly Glu Val Val Glu Ile Arg Ala Val Ser
145                 150                 155                 160

Ser Thr Ser Val Met Val Asn Ala Cys Tyr Asp Leu Leu Ser Glu Gly
                165                 170                 175

Leu Gly Val Val Pro Tyr Ala Cys Val
            180                 185
```

```
<210> SEQ ID NO 11
<211> LENGTH: 185
<212> TYPE: PRT
<213> ORGANISM: Ehrlichia sp.

<400> SEQUENCE: 11

Ala Val Lys Ile Thr Asn Ser Thr Ile Asp Gly Lys Val Cys Asn Gly
1               5                   10                  15

Ser Arg Glu Lys Gly Asn Ser Ala Gly Asn Asn Ser Ala Val Ala
            20                  25                  30

Thr Tyr Ala Gln Thr His Thr Ala Asn Thr Ser Thr Ser Gln Cys Ser
        35                  40                  45

Gly Leu Gly Thr Thr Val Val Lys Gln Gly Tyr Gly Ser Leu Asn Lys
    50                  55                  60

Phe Val Ser Leu Thr Gly Val Gly Glu Gly Lys Asn Trp Pro Thr Gly
65                  70                  75                  80

Lys Ile His Asp Gly Ser Ser Gly Val Lys Asp Gly Glu Gln Asn Gly
                85                  90                  95

Asn Ala Lys Ala Val Ala Lys Asp Leu Val Asp Leu Asn Arg Asp Glu
            100                 105                 110

Lys Thr Ile Val Ala Gly Leu Leu Ala Lys Thr Ile Glu Gly Gly Glu
```

```
                  115                 120                 125
Val Val Glu Ile Arg Ala Val Ser Ser Thr Ser Val Met Val Asn Ala
    130                 135                 140
Cys Tyr Asp Leu Leu Ser Glu Gly Leu Gly Val Val Pro Tyr Ala Cys
145                 150                 155                 160
Val Gly Leu Gly Gly Asn Phe Val Gly Val Val Asp Gly His Ile Thr
                165                 170                 175
Pro Lys Leu Ala Tyr Arg Leu Lys Ala
                180                 185

<210> SEQ ID NO 12
<211> LENGTH: 66
<212> TYPE: PRT
<213> ORGANISM: Ehrlichia sp.

<400> SEQUENCE: 12

Arg Phe Lys Thr Lys Gly Ile Arg Asp Ser Gly Ser Lys Glu Asp Glu
  1               5                  10                  15

Ala Asp Thr Val Tyr Leu Leu Ala Lys Glu Leu Ala Tyr Asp Val Val
                 20                  25                  30

Thr Gly Gln Thr Asp Asn Leu Ala Ala Ala Leu Ala Lys Thr Ser Gly
             35                  40                  45

Lys Asp Phe Val Gln Phe Ala Lys Ala Val Glu Ile Ser Asn Ser Thr
 50                  55                  60

Ile Gly
 65

<210> SEQ ID NO 13
<211> LENGTH: 155
<212> TYPE: PRT
<213> ORGANISM: Ehrlichia sp.

<400> SEQUENCE: 13

Tyr Ile Asp Ser Leu Arg Ser His Ser Leu Leu Lys Arg Lys Thr
  1               5                  10                  15

Lys Gly Ile Arg Asp Ser Gly Ser Lys Glu Asp Glu Ala Asp Thr Val
                 20                  25                  30

Tyr Leu Leu Ala Lys Glu Leu Ala Tyr Asp Val Val Thr Gly Gln Thr
             35                  40                  45

Asp Asn Leu Ala Ala Ala Leu Ala Lys Thr Ser Gly Lys Asp Phe Val
 50                  55                  60

Lys Phe Ala Asn Ala Val Val Gly Ile Ser His Pro Asp Val Asn Lys
 65                  70                  75                  80

Lys Val Cys Ala Thr Arg Lys Asp Ser Gly Thr Arg Tyr Ala Lys
                 85                  90                  95

Tyr Ala Thr Thr Asn Lys Ser Ser Asn Pro Glu Thr Ser Leu Cys
            100                 105                 110

Gly Asp Glu Gly Gly Ser Ser Gly Thr Asn Asn Thr Gln Glu Phe Leu
            115                 120                 125

Lys Glu Phe Val Ala Gln Thr Leu Val Glu Asn Glu Ser Lys Asn Trp
        130                 135                 140

Pro Thr Ser Ser Gly Thr Gly Leu Lys Thr Asn
145                 150                 155

<210> SEQ ID NO 14
<211> LENGTH: 176
<212> TYPE: PRT
```

-continued

<213> ORGANISM: Ehrlichia sp.

<400> SEQUENCE: 14

```
Asp Glu Ala Asp Thr Val Tyr Leu Leu Ala Lys Glu Leu Ala Tyr Asp
 1               5                  10                  15

Val Val Thr Gly Gln Thr Asp Lys Leu Thr Ala Ala Leu Ala Lys Thr
            20                  25                  30

Ser Gly Lys Asp Phe Val Gln Phe Ala Lys Ala Val Gly Val Ser His
        35                  40                  45

Pro Asn Ile Asp Gly Lys Val Cys Lys Thr Thr Leu Gly His Thr Ser
    50                  55                  60

Ala Asp Ser Tyr Gly Val Tyr Gly Glu Leu Thr Gly Gln Ala Ser Ala
65                  70                  75                  80

Ser Glu Thr Ser Leu Cys Gly Gly Lys Gly Lys Asn Ser Ser Gly Gly
                85                  90                  95

Gly Ala Ala Pro Glu Val Leu Arg Asp Phe Val Lys Lys Ser Leu Lys
            100                 105                 110

Asp Gly Gly Gln Asn Trp Pro Thr Ser Arg Ala Thr Glu Ser Ser Pro
        115                 120                 125

Lys Thr Lys Ser Glu Thr Asn Asp Asn Ala Lys Ala Val Ala Lys Asp
    130                 135                 140

Leu Val Asp Leu Asn Pro Glu Glu Lys Thr Ile Val Ala Gly Leu Leu
145                 150                 155                 160

Ala Lys Thr Ile Glu Gly Gly Glu Val Val Glu Ile Arg Ala Val Ser
                165                 170                 175
```

<210> SEQ ID NO 15
<211> LENGTH: 1185
<212> TYPE: DNA
<213> ORGANISM: Ehrlichia sp.

<400> SEQUENCE: 15

```
gaaacagcat tgctagattt cgttgaacaa tttgctaatt tgcaactaaa gcactcatga     60
taaagcttga tagtatttta gaggatagta ggcaatatgg tttaggggat ttcttcgcat    120
acttgttatc atcgtcctta tttgtgctta gttggtcgga tatttgtgca agttgttgta    180
aaatatgcat attgtatgta taggtgtgca agatatcatc tctttaggtg tatcgtgtag    240
cacttaaaca aatgctggtg aacgtagagg gattaaagga ggatttgcgt atatgtatgg    300
tatagatata gagctaagtg attacagaat tggtagtgaa accatttcca gtggagatga    360
tggctactac gaaggatgtg cttgtgacaa agatgccagc actaatgcgt actcgtatga    420
caagtgtagg gtagtacggg gaacgtggag accgagcgaa ctggttttat atgttggtga    480
tgagcatgtg gcatgtagag atgttgcttc gggtatgcat catggtaatt tgccagggga    540
aggtgtattt tatagaggca gaagcgggca gagctgctac tgctgaaggt ggtgtttata    600
ctaccgttgt ggaggcatta tcgctggtgc aagaggaaga gggtacaggt atgtacttga    660
taaacgcacc agaaaaagcg gtcgtaaggt ttttcaagat agaaaagagt gcagcagagg    720
aacctcaaac agtagatcct agtgtagttg agtcagcaac agggtcgggt gtagatacgc    780
aagaagaaca agaaatagat caagaagcac cagcaattga agaagttgag acagaagagc    840
aagaagttat tctggaagaa ggtactttga tagatcttga gcaacctgta gcgcaagtac    900
ctgtagtagc tgaagcagaa ttacctggtg ttgaagctgc agaagcgatt gtaccatcac    960
tagaagaaaa taagcttcaa gaagtggtag ttgctccaga agcgcaacaa ctagaatcag   1020
```

| | |
|---|---|
| ctcctgaagt tctgcgcca gcacaacctg agtctacagt tcttggtgtt gctgaaggtg | 1080 |
| atctaaagtc tgaagtatct gtagaagcta atgctgatgt acgcaaaaag aagtaatctc | 1140 |
| tggtccacra gagcaagaaa ttgcagaagc actagaggga actga | 1185 |

<210> SEQ ID NO 16
<211> LENGTH: 1131
<212> TYPE: DNA
<213> ORGANISM: Ehrlichia sp.

<400> SEQUENCE: 16

| | |
|---|---|
| ataaagggc tccagcaacg cagagagatg cttatggtaa gacggcttta catatagcag | 60 |
| ctgctaatgg tgacggtaag ctatataagt taattgcgaa aaaatgccca gatagctgtc | 120 |
| aagcactcct ttctcatatg ggagatacag cgttacatga ggctttatat tctgataagg | 180 |
| ttacagaaaa atgcttttta agatgctta aagagtctcg aaagcatttg tcaaactcat | 240 |
| ctttcggaga cttgcttaat actcctcaag aagcaaatgg tgacacgtta ctgcatctgg | 300 |
| ctgcatcgcg tggtttcggt aaagcatgta aaatactact aaagtctggg gcgtcagtat | 360 |
| cagtcgtgaa tgtagaggga aaaacaccgg tagatgttgc ggatccatca ttgaaaactc | 420 |
| gtccgtggtt ttttggaaag tccgttgtca caatgatggc tgaacgtgtt caagttcctg | 480 |
| aaggggggatt cccaccatat ctgccgcctg aaagtccaac tccttcttta ggatctattt | 540 |
| caagttttga gagtgtctct gcgctatcat ccttgggtag tggcctagat actgcaggag | 600 |
| ctgaggagtc tatctacgaa gaaattaagg atacagcaaa aggtacaacg gaagttgaaa | 660 |
| gcacatatac aactgtagga gctgaggagt ctatctacga agaaattaag gatacagcaa | 720 |
| aaggtacaac ggaagttgaa agcacatata caactgtagg agctgaaggt ccgagaacac | 780 |
| cagaaggtga agatctgtat gctactgtgg gagctgcaat tacttccgag gcgcaagcat | 840 |
| cagatgcggc gtcatctaag ggagaaaggc cggaatccat ttatgctgat ccatttgata | 900 |
| tagtgaaacc taggcaggaa aggcctgaat ctatctatgc tgacccattt gctgcggaac | 960 |
| gaacatcttc tggagtaacg acatttggcc ctaaggaaga gccgatttat gcaacagtga | 1020 |
| aaaagggtcc taagaagagt gatacttctc aaaaagaagg aacagcttct gaaaaagtcg | 1080 |
| gctcaacaat aactgtgatt aagaagaaag tgaaacctca ggttccagct a | 1131 |

<210> SEQ ID NO 17
<211> LENGTH: 800
<212> TYPE: DNA
<213> ORGANISM: Ehrlichia sp.

<400> SEQUENCE: 17

| | |
|---|---|
| aatgcgctcc acataactag cataacgttt tcagcaacgg cagatcttca tatataagca | 60 |
| ctgaacacct acgttccaag atcatgctct tcgcgcctgt ttacttggtg gctcagagtc | 120 |
| atcatcacta ggagttcgtg gtctgtgaga gctaacttgt gcttcttcca gcgtataact | 180 |
| agcacctccc aatcctgatg ctgaaggttg atcccacgaa taaggcataa tcccttgatc | 240 |
| ctgaggtggc acatagggag cttgtgatct tcccattcca gtactagtac ctcctagccc | 300 |
| agatgttgag aattggctag atggataagg aacattctct aggacacgta gtataatatg | 360 |
| aggggggggg ggaacgagtt gagctccctg tccggcagta cctcccaatc ctgatgttga | 420 |
| gggttgatcc catgatgttg agggttgatc ccacgatgtt gaaggttgtg catacgaata | 480 |
| gggcatcatc cctggatcat gtggtggaat atgcgaagct tgttgacttc ccattccagc | 540 |
| ggcacttcct aaccctgatg ttgagggttg atcccacgat gttgaatgtt gtgcatacga | 600 |

```
ataggcatc atccctggat catgtggtgg aatatgcgaa gcttgttgac ttcccattcc      660
agcggcactt cctaaccctg atgttgaggg ttgatcccac gatgttgaag gttgtgcata      720
cgaatagggc atcatccctg gatcatgtgg tggaatatgc gaagcttgtt gacttcccgt      780
tccagcggca cttcctaacc                                                  800
```

<210> SEQ ID NO 18
<211> LENGTH: 1011
<212> TYPE: DNA
<213> ORGANISM: Ehrlichia sp.

<400> SEQUENCE: 18

```
aatgtataca gtctcagatt cagaatctat aacttctttc gttactccac caatgttaat      60
ggcgaatatc tcatcgacta agcgttcagg atacttgcta tcattgtcgg tagagccatc     120
tgactttttt accgtgacat tctttttaaa gaaactcca tttacaacgg acaattcagt      180
gccattttgt agcttcgagc gcaactccac agcaaattca cgtattttct tcatacgtaa     240
tgcactcttc cattcttcag taagaataga cctgctttct tcaagtgtcc ttggtcttgg     300
aggcactact tcagtaacaa gaacgccgaa ataagcgtca ccattgctaa ccagatgaga     360
cggttttcct acggcagatg aaaacgccaa agtagtaaag gcgtttatac caagctgcaa     420
cggaaagtct ttcactaagt tgccagattt atcgagccca tgcatatcaa aattcgtcaa     480
aacaccactg atccgcgcac caaacatatc ctttagttca ttcagcaatg ccccgcggct     540
gatcatatcg tttgctttt tcacattgct aactagcaac tcacctgcct tttgccttct     600
aatatttgaa gatatcttct ctttcagctt ttctaggtct tccttagtga tctcatgctt     660
ccttattacc ttcatgatat gccagccgac aacgctacgg aacatttcac tgacttctcc     720
ttcatttagt gcaaacacca catttcgcac acctaccgga agaacatcct tagagatatt     780
attgagtgca atatcctcta tggtgtagcc agcatcacta accaattcct caaaagactt     840
accctcttgg taagctttgt aagctagctc agcttcattt ttgtctgtaa atactaaatt     900
tagaacatct ctttgatcat gtagttcact gttttttaatc tcaacgtcta ccttcttgat     960
ccgaaacaat gacatcagca agcaagtcgt cttctgccat gattatatga t             1011
```

<210> SEQ ID NO 19
<211> LENGTH: 513
<212> TYPE: DNA
<213> ORGANISM: Ehrlichia sp.

<400> SEQUENCE: 19

```
gcaaatattt ttcttggtgc cgccctaaaa gcctgaaaaa tttaaagaaa tgttactgct      60
ctagtcattc ataaaatgca aatagcctac agaaggagta tttactgcta taggcttgaa     120
agtgcaatcg ttatttacta tttttatac atatcgcagt acagagattt tacgcgctac     180
gcctgtgcat catagccgta ttgcatcaat aaattgtcgt tgctacgcgg gaaagctgct     240
tagcgcttga ccatttttca tacacattgt accatcatag cgagtgtggt gctcatgaga     300
gtgcgtagtg ttgccgccgg tttctcatgt tataatcttg ctgccgtttt gtgcagaagg     360
aggagtagtc tcgtttttttt ccaaaagaca atgtgctgga gtgtcccggt gagcctcaag     420
gttcttgtgg gatttgtgtg ggctgttgta taaataccac gttcgaagct gtcctagtgt     480
attcagcata tgttgaggaa gttgttgcta tga                                  513
```

<210> SEQ ID NO 20

<211> LENGTH: 464
<212> TYPE: DNA
<213> ORGANISM: Ehrlichia sp.

<400> SEQUENCE: 20

```
agtcattgag tcgagggtag tcttgtggat ccctgataaa tgttctaaaa tttaaaacaa      60
cactagagtt ttgatcacat gttggttgtc agaaaaaaaa tgtcaaaaaa tttaccaggg     120
cttttttgaaa tgcctagatt ttccatttct caatgaaact tgtttgatca tgactattcc    180
agctaatgga gcagtgtgat gtagaggaag gagccactga gggtatgtgg ggtgttagac     240
tggatcatca ttcttcaagg cgtgttcctt ggaatgcctg ggaggagagc aattttctat     300
taaaatttaa ttcgcctcct tccaaatatg gttccctgga cgatttagca aatagcattc     360
cttttttgga gattcaaaaa gcacattagc attgaggatt gctacagtaa agaaatctgc     420
ctaactttgt tttatccagt attgcctaaa attattggac cact                     464
```

<210> SEQ ID NO 21
<211> LENGTH: 527
<212> TYPE: DNA
<213> ORGANISM: Ehrlichia sp.

<400> SEQUENCE: 21

```
cctatggcag ctctaaactc ggcacgactg gtttctacaa gagattggtc gacattaaac      60
catgcgaaat cattgcgatc aattcttcct tcttttttcct gtatagcact acagacttcc    120
tctgcactag aagccactcg tgtcccgatg cgtacgtcac ggatgcaaag ccccaggtct     180
tttacgctgc cgggtgtgtc tatatcttcc acaacataat caacgcaagc gtgaatatgg     240
ataccagaaa cagaggtaac cctgtatact aaatgctctt ccaaaacatg ttgattaaca     300
ggtaagcgcc tagcactatc accattatca gcaacaacgc cttcatgcgc aacgtaatga     360
gcagcgagct caactggcag agatgaccca ctactgttac tcaagatact agataagagt     420
acccggagat tttctgtgtt tacaccagtt ttctccacaa tatttgcagc atgcttcggc     480
tgtgaccttta agatttcacg tatttcatcg gagtgttgta tgaaaat                 527
```

<210> SEQ ID NO 22
<211> LENGTH: 464
<212> TYPE: DNA
<213> ORGANISM: Ehrlichia sp.

<400> SEQUENCE: 22

```
ttcacctggc caaatcttat tggatcttca ggacaaagac caagaatctg cttctccaag      60
aagcattctc tgaccccac ctacctatct gactcttagc ttagattcct aatggtgtga    120
gtgtgtcaga gcctttactt agtctaagcg taactgtaaa aacatctttt caaaagtctc    180
tgcatgactg tctaggtctc acctatcaca ctgtaagcat ctggaaaaca aagccactga    240
gtcttccttt taccaaaaag gcctagcctt gttttttgaca aatggcaaga acacattaga   300
tgtttgttga gagaacaaaa ggagagaact cattatgaaa ctctgacaa catttatata    360
cctctctaca ttttttgtgt tggaggttag ttttcttttc taataatttg atttctttgg   420
atacatcgag gcaatacact taagaagcaa gaagattggg ggcc                   464
```

<210> SEQ ID NO 23
<211> LENGTH: 233
<212> TYPE: PRT
<213> ORGANISM: Ehrlichia sp.

<400> SEQUENCE: 23

-continued

```
Tyr Gly Glu Arg Gly Asp Arg Ala Asn Trp Phe Tyr Met Leu Val Met
 1               5                  10                  15

Ser Met Trp His Val Glu Met Leu Leu Arg Val Cys Ile Met Val Ile
            20                  25                  30

Cys Gln Gly Lys Val Tyr Phe Ile Glu Ala Glu Ala Gly Arg Ala Ala
        35                  40                  45

Thr Ala Glu Gly Gly Val Tyr Thr Thr Val Val Glu Ala Leu Ser Leu
    50                  55                  60

Val Gln Glu Glu Glu Gly Thr Gly Met Tyr Leu Ile Asn Ala Pro Glu
65                  70                  75                  80

Lys Ala Val Val Arg Phe Phe Lys Ile Glu Lys Ser Ala Ala Glu Glu
                85                  90                  95

Pro Gln Thr Val Asp Pro Ser Val Val Glu Ser Ala Thr Gly Ser Gly
            100                 105                 110

Val Asp Thr Gln Glu Glu Gln Glu Ile Asp Gln Glu Ala Pro Ala Ile
        115                 120                 125

Glu Glu Val Glu Thr Glu Glu Gln Glu Val Ile Leu Glu Glu Gly Thr
    130                 135                 140

Leu Ile Asp Leu Glu Gln Pro Val Ala Gln Val Pro Val Val Ala Glu
145                 150                 155                 160

Ala Glu Leu Pro Gly Val Glu Ala Ala Glu Ala Ile Val Pro Ser Leu
                165                 170                 175

Glu Glu Asn Lys Leu Gln Glu Val Val Val Ala Pro Glu Ala Gln Gln
            180                 185                 190

Leu Glu Ser Ala Pro Glu Val Ser Ala Pro Ala Gln Pro Glu Ser Thr
        195                 200                 205

Val Leu Gly Val Ala Glu Gly Asp Leu Lys Ser Glu Val Ser Val Glu
    210                 215                 220

Ala Asn Ala Asp Val Arg Lys Lys Lys
225                 230

<210> SEQ ID NO 24
<211> LENGTH: 376
<212> TYPE: PRT
<213> ORGANISM: Ehrlichia sp.

<400> SEQUENCE: 24

Lys Gly Ala Pro Ala Thr Gln Arg Asp Ala Tyr Gly Lys Thr Ala Leu
 1               5                  10                  15

His Ile Ala Ala Ala Asn Gly Asp Gly Lys Leu Tyr Lys Leu Ile Ala
            20                  25                  30

Lys Lys Cys Pro Asp Ser Cys Gln Ala Leu Leu Ser His Met Gly Asp
        35                  40                  45

Thr Ala Leu His Glu Ala Leu Tyr Ser Asp Lys Val Thr Glu Lys Cys
    50                  55                  60

Phe Leu Lys Met Leu Lys Glu Ser Arg Lys His Leu Ser Asn Ser Ser
65                  70                  75                  80

Phe Gly Asp Leu Leu Asn Thr Pro Gln Glu Ala Asn Gly Asp Thr Leu
                85                  90                  95

Leu His Leu Ala Ala Ser Arg Gly Phe Gly Lys Ala Cys Lys Ile Leu
            100                 105                 110

Leu Lys Ser Gly Ala Ser Val Ser Val Val Asn Val Glu Gly Lys Thr
        115                 120                 125

Pro Val Asp Val Ala Asp Pro Ser Leu Lys Thr Arg Pro Trp Phe Phe
```

```
            130                 135                 140
Gly Lys Ser Val Val Thr Met Met Ala Glu Arg Val Gln Val Pro Glu
145                 150                 155                 160

Gly Gly Phe Pro Pro Tyr Leu Pro Pro Glu Ser Pro Thr Pro Ser Leu
                165                 170                 175

Gly Ser Ile Ser Ser Phe Glu Ser Val Ser Ala Leu Ser Ser Leu Gly
            180                 185                 190

Ser Gly Leu Asp Thr Ala Gly Ala Glu Glu Ser Ile Tyr Glu Glu Ile
        195                 200                 205

Lys Asp Thr Ala Lys Gly Thr Thr Glu Val Glu Ser Thr Tyr Thr Thr
    210                 215                 220

Val Gly Ala Glu Glu Ser Ile Tyr Glu Glu Ile Lys Asp Thr Ala Lys
225                 230                 235                 240

Gly Thr Thr Glu Val Glu Ser Thr Tyr Thr Thr Val Gly Ala Glu Gly
                245                 250                 255

Pro Arg Thr Pro Glu Gly Glu Asp Leu Tyr Ala Thr Val Gly Ala Ala
                260                 265                 270

Ile Thr Ser Glu Ala Gln Ala Ser Asp Ala Ala Ser Ser Lys Gly Glu
            275                 280                 285

Arg Pro Glu Ser Ile Tyr Ala Asp Pro Phe Asp Ile Val Lys Pro Arg
290                 295                 300

Gln Glu Arg Pro Glu Ser Ile Tyr Ala Asp Pro Phe Ala Ala Glu Arg
305                 310                 315                 320

Thr Ser Ser Gly Val Thr Thr Phe Gly Pro Lys Glu Pro Ile Tyr
                325                 330                 335

Ala Thr Val Lys Lys Gly Pro Lys Lys Ser Asp Thr Ser Gln Lys Glu
            340                 345                 350

Gly Thr Ala Ser Glu Lys Val Gly Ser Thr Ile Thr Val Ile Lys Lys
            355                 360                 365

Lys Val Lys Pro Gln Val Pro Ala
            370                 375

<210> SEQ ID NO 25
<211> LENGTH: 148
<212> TYPE: PRT
<213> ORGANISM: Ehrlichia sp.

<400> SEQUENCE: 25

Tyr Glu Gly Gly Gly Glu Arg Val Glu Leu Pro Val Arg Gln Tyr Leu
1               5                   10                  15

Pro Ile Leu Met Leu Arg Val Asp Pro Met Met Leu Arg Val Asp Pro
            20                  25                  30

Thr Met Leu Lys Val Val His Thr Asn Arg Ala Ser Ser Leu Asp His
        35                  40                  45

Val Val Glu Tyr Ala Lys Leu Val Asp Phe Pro Phe Gln Arg His Phe
    50                  55                  60

Leu Thr Leu Met Leu Arg Val Asp Pro Thr Met Leu Lys Val Val His
65                  70                  75                  80

Thr Asn Arg Ala Ser Ser Leu Asp His Val Val Glu Tyr Ala Lys Leu
                85                  90                  95

Val Asp Phe Pro Phe Gln Arg His Phe Leu Thr Leu Met Leu Arg Val
            100                 105                 110

Asp Pro Thr Met Leu Lys Val Val His Thr Asn Arg Ala Ser Ser Leu
        115                 120                 125
```

```
Asp His Val Val Glu Tyr Ala Lys Leu Val Asp Phe Pro Phe Gln Arg
    130                 135                 140

His Phe Leu Thr
145

<210> SEQ ID NO 26
<211> LENGTH: 89
<212> TYPE: PRT
<213> ORGANISM: Ehrlichia sp.

<400> SEQUENCE: 26

Tyr Gly Ser Ser Lys Leu Gly Thr Thr Gly Phe Tyr Lys Arg Leu Val
1               5                   10                  15

Asp Ile Lys Pro Cys Glu Ile Ile Ala Ile Asn Ser Ser Phe Phe Phe
            20                  25                  30

Leu Tyr Ser Thr Thr Asp Phe Leu Cys Thr Arg Ser His Ser Cys Pro
        35                  40                  45

Asp Ala Tyr Val Thr Asp Ala Lys Pro Gln Val Phe Tyr Ala Ala Gly
    50                  55                  60

Cys Val Tyr Ile Phe His Asn Ile Ile Asn Ala Ser Val Asn Met Asp
65                  70                  75                  80

Thr Arg Asn Arg Gly Asn Pro Val Tyr
                85

<210> SEQ ID NO 27
<211> LENGTH: 238
<212> TYPE: PRT
<213> ORGANISM: Ehrlichia sp.

<400> SEQUENCE: 27

Leu Gly Ser Ala Ala Gly Thr Gly Ser Gln Gln Ala Ser His Ile Pro
1               5                   10                  15

Pro His Asp Pro Gly Met Met Pro Tyr Ser Tyr Ala Gln Pro Ser Thr
            20                  25                  30

Ser Trp Asp Gln Pro Ser Thr Ser Gly Leu Gly Ser Ala Ala Gly Met
        35                  40                  45

Gly Ser Gln Gln Ala Ser His Ile Pro Pro His Asp Pro Gly Met Met
    50                  55                  60

Pro Tyr Ser Tyr Ala Gln Pro Ser Thr Ser Trp Asp Gln Pro Ser Thr
65                  70                  75                  80

Ser Gly Leu Gly Ser Ala Ala Gly Met Gly Ser Gln Gln Ala Ser His
                85                  90                  95

Ile Pro Pro His Asp Pro Gly Met Met Pro Tyr Ser Tyr Ala Gln Pro
            100                 105                 110

Ser Thr Ser Trp Asp Gln Pro Ser Thr Ser Trp Asp Gln Pro Ser Thr
        115                 120                 125

Ser Gly Leu Gly Gly Thr Ala Gly Gln Gly Ala Gln Leu Val Pro Pro
    130                 135                 140

Pro Pro His Ile Ile Leu Arg Val Leu Glu Asn Val Pro Tyr Pro Ser
145                 150                 155                 160

Ser Gln Phe Ser Thr Ser Gly Leu Gly Gly Thr Ser Thr Gly Met Gly
                165                 170                 175

Arg Ser Gln Ala Pro Tyr Val Pro Pro Gln Asp Gln Gly Ile Met Pro
            180                 185                 190

Tyr Ser Trp Asp Gln Pro Ser Ala Ser Gly Leu Gly Gly Ala Ser Tyr
        195                 200                 205
```

```
Thr Leu Glu Glu Ala Gln Val Ser Ser His Arg Pro Arg Thr Pro Ser
    210                 215                 220
Asp Asp Asp Ser Glu Pro Pro Ser Lys Gln Ala Arg Arg Ala
225                 230                 235
```

<210> SEQ ID NO 28
<211> LENGTH: 334
<212> TYPE: PRT
<213> ORGANISM: Ehrlichia sp.

<400> SEQUENCE: 28

```
Ser Trp Gln Lys Thr Thr Cys Leu Leu Met Ser Leu Phe Arg Ile Lys
 1               5                  10                  15
Lys Val Asp Val Glu Ile Lys Asn Ser Glu Leu His Asp Gln Arg Asp
             20                  25                  30
Val Leu Asn Leu Val Phe Thr Asp Lys Asn Glu Ala Glu Leu Ala Tyr
         35                  40                  45
Lys Ala Tyr Gln Glu Gly Lys Ser Phe Glu Glu Leu Val Ser Asp Ala
     50                  55                  60
Gly Tyr Thr Ile Glu Asp Ile Ala Leu Asn Asn Ile Ser Lys Asp Val
 65                  70                  75                  80
Leu Pro Val Gly Val Arg Asn Val Val Phe Ala Leu Asn Glu Gly Glu
                 85                  90                  95
Val Ser Glu Met Phe Arg Ser Val Val Gly Trp His Ile Met Lys Val
            100                 105                 110
Ile Arg Lys His Glu Ile Thr Lys Glu Asp Leu Glu Lys Leu Lys Glu
        115                 120                 125
Lys Ile Ser Ser Asn Ile Arg Arg Gln Lys Ala Gly Glu Leu Leu Val
    130                 135                 140
Ser Asn Val Lys Lys Ala Asn Asp Met Ile Ser Arg Gly Ala Leu Leu
145                 150                 155                 160
Asn Glu Leu Lys Asp Met Phe Gly Ala Arg Ile Ser Gly Val Leu Thr
                165                 170                 175
Asn Phe Asp Met His Gly Leu Asp Lys Ser Gly Asn Leu Val Lys Asp
            180                 185                 190
Phe Pro Leu Gln Leu Gly Ile Asn Ala Phe Thr Thr Leu Ala Phe Ser
        195                 200                 205
Ser Ala Val Gly Lys Pro Ser His Leu Val Ser Asn Gly Asp Ala Tyr
    210                 215                 220
Phe Gly Val Leu Val Thr Glu Val Val Pro Pro Arg Pro Arg Thr Leu
225                 230                 235                 240
Glu Glu Ser Arg Ser Ile Leu Thr Glu Glu Trp Lys Ser Ala Leu Arg
                245                 250                 255
Met Lys Lys Ile Arg Glu Phe Ala Val Glu Leu Arg Ser Lys Leu Gln
            260                 265                 270
Asn Gly Thr Glu Leu Ser Val Val Asn Gly Val Ser Phe Lys Lys Asn
        275                 280                 285
Val Thr Val Lys Ser Asp Gly Ser Thr Asp Asn Asp Ser Lys Tyr
    290                 295                 300
Pro Glu Arg Leu Val Asp Glu Ile Phe Ala Ile Asn Ile Gly Gly Val
305                 310                 315                 320
Thr Lys Glu Val Ile Asp Ser Glu Ser Glu Thr Val Tyr Ile
                325                 330
```

<210> SEQ ID NO 29

```
<211> LENGTH: 175
<212> TYPE: PRT
<213> ORGANISM: Ehrlichia sp.

<400> SEQUENCE: 29

Ile Phe Ile Gln His Ser Asp Glu Ile Arg Glu Ile Leu Arg Ser Gln
 1               5                  10                  15

Pro Lys His Ala Ala Asn Ile Val Glu Lys Thr Gly Val Asn Thr Glu
            20                  25                  30

Asn Leu Arg Val Leu Leu Ser Ser Ile Leu Ser Asn Ser Ser Gly Ser
        35                  40                  45

Ser Leu Pro Val Glu Leu Ala Ala His Tyr Val Ala His Glu Gly Val
    50                  55                  60

Val Ala Asp Asn Gly Asp Ser Ala Arg Arg Leu Pro Val Asn Gln His
65                  70                  75                  80

Val Leu Glu Glu His Leu Val Tyr Arg Val Thr Ser Val Ser Gly Ile
                85                  90                  95

His Ile His Ala Cys Val Asp Tyr Val Val Glu Asp Ile Asp Thr Pro
            100                 105                 110

Gly Ser Val Lys Asp Leu Gly Leu Cys Ile Arg Asp Val Arg Ile Gly
        115                 120                 125

Thr Arg Val Ala Ser Ser Ala Glu Glu Val Cys Ser Ala Ile Gln Glu
    130                 135                 140

Lys Glu Gly Arg Ile Asp Arg Asn Asp Phe Ala Trp Phe Asn Val Asp
145                 150                 155                 160

Gln Ser Leu Val Glu Thr Ser Arg Ala Glu Phe Arg Ala Ala Ile
                165                 170                 175

<210> SEQ ID NO 30
<211> LENGTH: 41
<212> TYPE: PRT
<213> ORGANISM: Ehrlichia sp.
<220> FEATURE:
<221> NAME/KEY: VARIANT
<222> LOCATION: (7)...(7)
<223> OTHER INFORMATION: Xaa = Methionine or Threonine

<400> SEQUENCE: 30

Leu Gly Ser Ala Ala Gly Xaa Gly Ser Gln Gln Ala Ser His Ile Pro
 1               5                  10                  15

Pro His Asp Pro Gly Met Met Pro Tyr Ser Tyr Ala Gln Pro Ser Thr
            20                  25                  30

Ser Trp Asp Gln Pro Ser Thr Ser Gly
        35                  40

<210> SEQ ID NO 31
<211> LENGTH: 860
<212> TYPE: DNA
<213> ORGANISM: Ehrlichia sp.

<400> SEQUENCE: 31
aaaagcttaa ggaagatgtg gcttctatgt cggatgaggc tttgctgaag tttgccaata      60
ggctcagaag aggtgttcct atggctgctc cggtgtttga gggtccgaag gatgcgcaga     120
tttcccggct tttggaatta gcggatgttg atccgtctgg gcaggtggat ctttatgatg     180
ggcgttcagg gcagaagttt gatcgcaagg taactgttgg atacatttac atgttgaagc     240
tccatcactt ggtggatgac aagatacatg ctaggtctgt tggtccgtat ggtctggtta     300
ctcagcaacc tcttggagga aagtcgcact tggtgggca  gagatttggg gaaatggaat     360
```

```
gctgggcatt gcaggcctat ggtgctgctt atactttgca ggaaatgcta actgtcaaat      420
ctgacgatat cgtaggtagg gtaacaatct atgaatccat aattaagggg gatagcaact      480
tcgagtgtgg tattcctgag tcgtttaatg tcatggtcaa ggagttacgc tcgctgtgcc      540
ttgatgttgt tctaaagcag gataaagagt ttactagtag caaggtggag tagggattta      600
caattatgaa gacgttggat ttgtatggct ataccagtat agcacagtcg ttcgataaca      660
tttgcatatc catatctagt ccacaaagta taagggctat gtcctatgga gaaatcaagg      720
atatctctac tactatctat cgtaccttta aggtggagag ggggggcta ttctgtccta       780 agatctttgg tccggttaat gatgacgagt gtctttgtgg taagtatagg aaaaagcgct      840 acagggcat tgtctgtgaa                                                    860
```

<210> SEQ ID NO 32
<211> LENGTH: 196
<212> TYPE: PRT
<213> ORGANISM: Ehrlichia sp.

<400> SEQUENCE: 32

```
Lys Leu Lys Glu Asp Val Ala Ser Met Ser Asp Glu Ala Leu Leu Lys
 1               5                  10                  15

Phe Ala Asn Arg Leu Arg Arg Gly Val Pro Met Ala Ala Pro Val Phe
            20                  25                  30

Glu Gly Pro Lys Asp Ala Gln Ile Ser Arg Leu Leu Glu Leu Ala Asp
        35                  40                  45

Val Asp Pro Ser Gly Gln Val Asp Leu Tyr Asp Gly Arg Ser Gly Gln
    50                  55                  60

Lys Phe Asp Arg Lys Val Thr Val Gly Tyr Ile Tyr Met Leu Lys Leu
65                  70                  75                  80

His His Leu Val Asp Asp Lys Ile His Ala Arg Ser Val Gly Pro Tyr
                85                  90                  95

Gly Leu Val Thr Gln Gln Pro Leu Gly Gly Lys Ser His Phe Gly Gly
           100                 105                 110

Gln Arg Phe Gly Glu Met Glu Cys Trp Ala Leu Gln Ala Tyr Gly Ala
       115                 120                 125

Ala Tyr Thr Leu Gln Glu Met Leu Thr Val Lys Ser Asp Asp Ile Val
   130                 135                 140

Gly Arg Val Thr Ile Tyr Glu Ser Ile Ile Lys Gly Asp Ser Asn Phe
145                 150                 155                 160

Glu Cys Gly Ile Pro Glu Ser Phe Asn Val Met Val Lys Glu Leu Arg
                165                 170                 175

Ser Leu Cys Leu Asp Val Val Leu Lys Gln Asp Lys Glu Phe Thr Ser
            180                 185                 190

Ser Lys Val Glu
        195
```

<210> SEQ ID NO 33
<211> LENGTH: 89
<212> TYPE: PRT
<213> ORGANISM: Ehrlichia sp.

<400> SEQUENCE: 33

```
Gly Phe Thr Ile Met Lys Thr Leu Asp Leu Tyr Gly Tyr Thr Ser Ile
 1               5                  10                  15

Ala Gln Ser Phe Asp Asn Ile Cys Ile Ser Ile Ser Ser Pro Gln Ser
            20                  25                  30
```

```
Ile Arg Ala Met Ser Tyr Gly Glu Ile Lys Asp Ile Ser Thr Thr Ile
         35                  40                  45

Tyr Arg Thr Phe Lys Val Glu Lys Gly Gly Leu Phe Cys Pro Lys Ile
 50                  55                  60

Phe Gly Pro Val Asn Asp Glu Cys Leu Cys Gly Lys Tyr Arg Lys
65                   70                  75                  80

Lys Arg Tyr Arg Gly Ile Val Cys Glu
                85
```

<210> SEQ ID NO 34
<211> LENGTH: 484
<212> TYPE: DNA
<213> ORGANISM: Ehrlichia sp.

<400> SEQUENCE: 34

```
atcataagct ttacatgtcc tatccaggcg attatcccta tccatagcat agtaacgccc      60
tgcaacagta gcaatttcgg catttaagtg ctcaatttta gcgttcagca taccgatata     120
cttctcagca gaacgcggtg gaacatccct accatctaga attacatgta taaaaacctt     180
gatgccaaat ccggtgataa cctcaataat ggtttccatg tgcgcctgaa gagaatgcac     240
tccaccatca gaaagcagac caatcatgtg catacccca ccttcgcct gtatatcgcg       300
cacaaagtcc aacaatttag gattcttgtg aacctcatta atctcaagat taattctcaa     360
cagatcctga agcactatcc tgccgcatcc tatacttatg tgccctactt ctgaattccc     420
gaactgacct gaaggcaatc cgacatccgt tccactagca gacaaactac tcataggaca     480
gcat                                                                   484
```

<210> SEQ ID NO 35
<211> LENGTH: 161
<212> TYPE: PRT
<213> ORGANISM: Ehrlichia sp.

<400> SEQUENCE: 35

```
Cys Cys Pro Met Ser Ser Leu Ser Ala Ser Gly Thr Asp Val Gly Leu
 1               5                  10                  15

Pro Ser Gly Gln Phe Gly Asn Ser Glu Val Gly His Ile Ser Ile Gly
                20                  25                  30

Cys Gly Arg Ile Val Leu Gln Asp Leu Leu Arg Ile Asn Leu Glu Ile
         35                  40                  45

Asn Glu Val His Lys Asn Pro Lys Leu Leu Asp Phe Val Arg Asp Ile
 50                  55                  60

Gln Ala Lys Gly Gly Val Cys His Met Ile Gly Leu Leu Ser Asp Gly
65                   70                  75                  80

Gly Val His Ser Leu Gln Ala His Met Glu Thr Ile Ile Glu Val Ile
                85                  90                  95

Thr Gly Phe Gly Ile Lys Val Phe Ile His Val Ile Leu Asp Gly Arg
                100                 105                 110

Asp Val Pro Pro Arg Ser Ala Glu Lys Tyr Ile Gly Met Leu Asn Ala
            115                 120                 125

Lys Ile Glu His Leu Asn Ala Glu Ile Ala Thr Val Ala Gly Arg Tyr
        130                 135                 140

Tyr Ala Met Asp Arg Asp Asn Arg Leu Asp Arg Thr Cys Lys Ala Tyr
145                 150                 155                 160

Asp
```

<210> SEQ ID NO 36
<211> LENGTH: 1039
<212> TYPE: DNA
<213> ORGANISM: Ehrlichia sp.

<400> SEQUENCE: 36

```
ttaatcagag cggttgtgct agtcctttcc gaaattcctg tgctgaatgc ggagatttca     60
ggcgatgata tagtctacag ggactattgt aacattggag tcgcggtagg taccgataag    120
gggttagtgg tgcctgttat cagaagagcg gaaactatgt cacttgctga aatggagcaa    180
gcacttgttg acttaagtac aaaagcaaga agtggcaagc tctctgtttc tgatatgtct    240
ggtgcaacct ttactattac caatggtggt gtgtatgggt cgctattgtc tacccctata    300
atcaaccctc ctcaatctgg aatcttgggt atgcatgcta tacagcagcg tcctgtggca    360
gtagatggta aggtagagat aaggcctatg atgtatttgg cgctatcata tgatcataga    420
atagttgacg ggcaaggtgc tgtgacgttt ttggtaagag tgaagcagta catagaagat    480
cctaacagat tggctctagg aatttagggg gtttttatgg ggcggggtac aataaccatc    540
cactccaaag aggattttgc ctgtatgaga agggctggga tgcttgcagc taaggtgctt    600
gattttataa cgccgcatgt tgttcctggt gtgactacta atgctctgaa tgatctatgt    660
cacgatttca tcatttctgc cggggctatt ccagcgcctt tggctatag agggtatcct    720 aagtctattt gtacttcgaa gaattttgtg gtttgccatg gcattccaga tgatattgca    780
ttaaaaaacg gcgatatagt taacatagac gttactgtga tcctcgatgg ttggcacggg    840
gatactaata ggatgtattg ggttggtgat aacgtctcta ttaaggctaa gcgcatttgt    900
gaggcaagtt ataaggcatt gatggcggcg attggtgtaa tacagccagg taagaagctc    960
aatagcatag ggttagctat agaggaagaa atcagaggtt atggatactc cattgttaga   1020
gattactgcg gacatggga                                                 1039
```

<210> SEQ ID NO 37
<211> LENGTH: 168
<212> TYPE: PRT
<213> ORGANISM: Ehrlichia sp.

<400> SEQUENCE: 37

```
Leu Ile Arg Ala Val Val Leu Val Leu Ser Glu Ile Pro Val Leu Asn
 1               5                  10                  15

Ala Glu Ile Ser Gly Asp Asp Ile Val Tyr Arg Asp Tyr Cys Asn Ile
            20                  25                  30

Gly Val Ala Val Gly Thr Asp Lys Gly Leu Val Val Pro Val Ile Arg
        35                  40                  45

Arg Ala Glu Thr Met Ser Leu Ala Glu Met Glu Gln Ala Leu Val Asp
    50                  55                  60

Leu Ser Thr Lys Ala Arg Ser Gly Lys Leu Ser Val Ser Asp Met Ser
65                  70                  75                  80

Gly Ala Thr Phe Thr Ile Thr Asn Gly Gly Val Tyr Gly Ser Leu Leu
                85                  90                  95

Ser Thr Pro Ile Ile Asn Pro Pro Gln Ser Gly Ile Leu Gly Met His
            100                 105                 110

Ala Ile Gln Gln Arg Pro Val Ala Val Asp Gly Lys Val Glu Ile Arg
        115                 120                 125

Pro Met Met Tyr Leu Ala Leu Ser Tyr Asp His Arg Ile Val Asp Gly
    130                 135                 140
```

Gln Gly Ala Val Thr Phe Leu Val Arg Val Lys Gln Tyr Ile Glu Asp
145                 150                 155                 160

Pro Asn Arg Leu Ala Leu Gly Ile
                165

<210> SEQ ID NO 38
<211> LENGTH: 177
<212> TYPE: PRT
<213> ORGANISM: Ehrlichia sp.

<400> SEQUENCE: 38

Gly Val Phe Met Gly Arg Gly Thr Ile Thr Ile His Ser Lys Glu Asp
1               5                   10                  15

Phe Ala Cys Met Arg Arg Ala Gly Met Leu Ala Ala Lys Val Leu Asp
                20                  25                  30

Phe Ile Thr Pro His Val Val Pro Gly Val Thr Thr Asn Ala Leu Asn
            35                  40                  45

Asp Leu Cys His Asp Phe Ile Ile Ser Ala Gly Ala Ile Pro Ala Pro
        50                  55                  60

Leu Gly Tyr Arg Gly Tyr Pro Lys Ser Ile Cys Thr Ser Lys Asn Phe
65                  70                  75                  80

Val Val Cys His Gly Ile Pro Asp Asp Ile Ala Leu Lys Asn Gly Asp
                85                  90                  95

Ile Val Asn Ile Asp Val Thr Val Ile Leu Asp Gly Trp His Gly Asp
                100                 105                 110

Thr Asn Arg Met Tyr Trp Val Gly Asp Asn Val Ser Ile Lys Ala Lys
            115                 120                 125

Arg Ile Cys Glu Ala Ser Tyr Lys Ala Leu Met Ala Ala Ile Gly Val
        130                 135                 140

Ile Gln Pro Gly Lys Lys Leu Asn Ser Ile Gly Leu Ala Ile Glu Glu
145                 150                 155                 160

Glu Ile Arg Gly Tyr Gly Tyr Ser Ile Val Arg Asp Tyr Cys Gly His
                165                 170                 175

Gly

<210> SEQ ID NO 39
<211> LENGTH: 2129
<212> TYPE: DNA
<213> ORGANISM: Ehrlichia sp.

<400> SEQUENCE: 39
tttacctctt tttgaagaaa tcttaaagaa aaagcatggg gcacggtcca acacatcgaa      60
ccttccccat acttttcacg agaaagatat cctaataact tagaacatct tcatcgtcag     120
gatcctttaa cggcaaagca gtcggaacat ctactaactc ttgctgcata ccagcatcag     180
cttctacaga tacttcaacc ttctcaactt cttcagttgc ttgtgtctct tgatcagaga     240
ttcctgcttc ttgctgcata ccagcatcag cttctacaga tacttcagac ttcagatcac     300
cttcagtaac accaagaact gtagactcag gttgtactgg cgcagaaact tcaggagctg     360
attctagttg ttgcgcttct ggagcaacta ccacttcttg aagcttattt tcttctagtg     420
atggtacaat cgcttctgca gcttcaacac caggtaattc tgcttcagct actacaggta     480
cttgcgctac aggttgctca agatctatca agtaccttc ttctagaata acttctggct     540
cttccgtttt tgtttctaca gatacttcaa ccttttcaac ttcttcagtt gcttgtgtct     600
cttgatcaga gattcctgct tcttgctgca taccagcatc agcttctaca gatacttcag     660

-continued

```
acttcagatc accttcagta acaccaagaa ctgtagactc aggttgtgct ggtgcagaaa      720
cttcaggagc tgattctagt tgttgcgctt ctggagcaac taccacttct tgaagcttat      780
tttcttctag tgatggtaca atcgcttctg cagcttcaac accaggtaat tctgcttcag      840
ctactacagg tacttgtgct acaggttgct caagatctat caaagtatct tcctttagaa      900
gaacttctgt ttcttctttt acttctacag gagcttcagt tccctctagt gcttctgcaa      960
tttcttgctc ttgttgacca gagattactt cttttttgcgc tacatcagca ttagcttcta     1020
cagatacttc agactttaga tcaccttcag caacaccaag aactgtagac tcaggttgtg     1080
ctggcgcaga aacttcagga gctgattcta gttgttgcgc ttctggagca actaccactt     1140
cttgaagctt attttcttct agtgatggta caatcgcttc tgcagcttca acaccaggta     1200
attctgcttc agctactaca ggtacttgcg ctacaggttg ctcaagatct atcaaagtac     1260
cttcttccag ataacttct tgctcttctg tctcaacttc ttcaattgct ggtgcttctt     1320
gatctatttc ttgttcttct tgcgtatcta cacccgaccc tgttgctgac tcaactacac     1380
taggatctac tgttttgaggt tcctctgctg cactctttttc tatcttgaaa aaccttacga     1440
ccgcttttttc tggtgcgttt atcaagtaca tacctgtacc ctcttcctct tgcaccagcg     1500
ataatgcctc cacaacggta gtataaaaca caccttcagc agtagcagct ctgcccgctt     1560
ctgcctctat aaaatacacc ttccctggca aattaccatg atgcataccc gaagcaacat     1620
ctctacatgc cacatgctca tcaccaacat ataaaaccag ttcgctcggt ctccacgttc     1680
cccgtactac cctacacttg tcatacgagt acgcattagt gctggcatct tgtcacaag     1740
cacatccttc gtagtagcca tcatctccac tggaaatggt ttcactacca attctgtaat     1800
cacttagctc tatatctata ccatacatat acgcaaatcc tcctttaatc cctctacgtt     1860
caccagcatt tgtttaagtg ctacacgata cacctaaaga gatgatatct tgcacaccta     1920
tacatacaat atgcatattt tacaacaact tgcacaaata tccgaccaac taagcacaaa     1980
taaggacgat gataacaagt atgcgaagaa atcccctaaa ccatattgcc tactatcctc     2040
taaaatacta tcaagcttta tcatgagtgc tttagttgca aattagcaaa ttgttcaacg     2100
aaatctagca atgctgtttc ctcgtgccg                                       2129
```

```
<210> SEQ ID NO 40
<211> LENGTH: 1919
<212> TYPE: DNA
<213> ORGANISM: Ehrlichia sp.

<400> SEQUENCE: 40
atgctgtgaa aattactaac tccactatcg atgggaaggt ttgtaatggt agtagagaga       60
agggaatag tgctgggaac aacaacagtg ctgtggctac ctacgcgcag actcacacag      120
cgaatacatc aacgtcacag tgtagcggtc tagggaccac tgttgtcaaa caaggttatg      180
gaagtttgaa taagtttgtt agcctgacgg gggttggtga aggtaaaaat tggcctacag      240
gtaagataca cgacggtagt agtggtgtca agatggtga acagaacggg aatgccaaag      300
ccgtagctaa agacctagta gatcttaatc gtgacgaaaa aaccatagta gcaggattac      360
tagctaaaac tattgaaggg ggtgaagttg ttgagatcag gcggttttct tctacttctg      420
tgatggttaa tgcttgttat gatcttctta gtgaaggttt aggcgttgtt ccttacgctt      480
gtgtcggtct cggaggtaac ttcgtgggcg ttgttgatgg gcatatcact cctaagcttg      540
cttatagatt aaaggctggc ttgagttatc agctctctcc tgaaatctct gcttttgctg      600
ggggtttcta ccatcgtgtt gtgggagatg gtgtttatga tgatctgcca gctcaacgtc      660
```

-continued

```
ttgtagatga tactagtccg gcgggccgta ctaaggatac tgctgttgct aacttctcca      720
tggcttatgt cggtggggaa tttggtgtta ggtttgcttt ttaaggtggt ttgttggaag      780
cggggtaagt caaacttacc ccgcttctat tagggagtta gtatatgaga tctagaagta      840
agctattatt aggaagcgta atgatgtcga tggctatagt catggctggg aatgatgtca      900
gggctcatga tgacgttagc gctttggaga ctggtggtgc gggatatttc tatgttggtt      960
tggattacag tccagcgttt agcaagataa gagattttag tataaggag agtaacggag      1020
agactaaggc agtatatcca tacttaaagg atggaaagag tgtaaagcta gagtcacaca      1080
agtttgactg gaacactcct gatcctcgga ttgggtttaa ggacaacatg cttgtagcta      1140
tggaaggcag tgttggttat ggtattggtg gtgccagggt tgagcttgag attggttacg      1200
agcgcttcaa gaccaagggt attagagata gtggtagtaa ggaagatgaa gctgatacag      1260
tatatctact agctaaggag ttagcttatg atgttgttac tggacagact gataaccttg      1320
ctgctgctct tgccaagacc tctggaaaag atatcgttca gtttgccaat gctgttaaaa      1380
ttactaactc cgctatcgat gggaagattt gtaataggg taaggctagt ggcggcagca      1440
aaggcctgtc tagtagcaaa gcaggttcat gtgatagcat agataagcag agtggaagct      1500
tggaacagag tttaacagcg gctttaggtg ataaaggtgc tgaaaagtgg cctaaaatta      1560
ataatggcac tagcgacacg acactgaatg gaaacgacac tagtagtaca ccgtacacta      1620
aagatgcctc tgctactgta gctaaagacc tcgtagctct taatcatgac gaaaaaacca      1680
tagtagcagg gttactagct aaaactattg aaggggggtga ggttgttgag attagggcgg      1740
tttcttctac ttctgtaatg gtcaatgctt gttatgatct tcttagtgaa ggtctaggcg      1800
ttgttcctta cgcttgtgtc ggtcttggag gtaacttcgt gggcgttgtt gatgggcata      1860
tcactcctaa gcttgcttat agattaaagg ctggcttgag ttatcagctc tctcctgaa      1919
```

<210> SEQ ID NO 41
<211> LENGTH: 3073
<212> TYPE: DNA
<213> ORGANISM: Ehrlichia sp.

<400> SEQUENCE: 41

```
tcccatgtcc gcagtaatct ctaacaatgg agtatccata acctctgatt tcttcctcta       60
tagctaaccc tatgctattg agcttcttac ctggctgtat tacaccaatc gccgccatca      120
atgcctata acttgcctca caaatgcgct tagccttaat agagacgtta tcaccaaccc       180
aatacatcct attagtatcc ccgtgccaac catcgaggat cacagtaacg tctatgttaa      240
ctatatcgcc gttttttaat gcaatatcat ctggaatgcc atggcaaacc acaaaattct      300
tcgaagtaca aatagactta ggatacectc tatagcccaa aggcgctgga atagcccegg     360
cagaaatgat gaaatcgtga catagatcat tcagagcatt agtagtcaca ccaggaacaa      420
catgcggcgt tataaaatca agcaccttag ctgcaagcat cccagcccct ctcatacagg      480
caaaatcctc tttggagtgg atggttattg taccccgccc cataaaaacc ccctaaattc      540
ctagagccaa tctgttagga tcttctatgt actgcttcac tcttaccaaa aacgtcacag      600
caccttgccc gtcaactatt ctatgatcat atgatacgc caaatacatc ataggcctta      660
tctctacctt accatctact gccacaggac gctgctgtat agcatgcata cccaagattc      720
cagattgagg agggttgatt ataggggtag acaatagcga cccatacaca ccaccattgg      780
taatagtaaa ggttgcacca gacatatcag aaacagagag cttgccactt cttgcttttg      840
```

-continued

```
tacttaagtc aacaagtgct tgctccattt cagcaagtga catagtttcc gctcttctga    900
taacaggcac cactaacccc ttatcggtac ctaccgcgac tccaatgtta caatagtccc    960
tgtagactat atcatcgcct gaaatctccg cattcagcac aggaatttcg gaaggacta   1020 gcacaaccgc tctgataaag aaggacataa acccaagctt aacatcatac ctcttcacaa   1080
aggcatcttt gtacttagct ctgagctcca tcactttgct catatcaact tcattaaagg   1140
tgctgagtgt agcagaggta ttttgtgact ccttaagcct agcagctata acttggcgga   1200
ttttgctcat cttcacgcgt cttccaccca ccacgtcgcc atggcaactc atcagatcct   1260
tagacggctg gctagcaact atcttcttgt cttgttcact cttagcactc atacccaaag   1320
ctctagaagt aggagttgtg ttgattcctg caacaaaatc ttctacagta ggagttacta   1380
gacctttgcc ttcaataatt gtcttttcct gcggtttttg agtgctcact gcctgtgcaa   1440 caacggggttg agcaagcacc tcctccttgc tctctggctc cttattaaca ccctctgcag   1500
tagcctcacc ctgtggccgt atgatagcca agacctgccc ttggtaatca cttcttcatc   1560
tgcaactctc aactctgtga gaacaccagc aacaggggct gatatttcaa gagaagtctt   1620
gtctgtttca acaatgaaga gcacatcttc tgcagataca gtatctccca ccttttttcat  1680 tacccgaatc ggagcttcta gaatggattc gccaccaaga ttctcagccc taacttctac   1740
agcatcaccc ataaatacaa accagaacta aaacaaaaaa cacagattga aaggcagtgt   1800
aatcaccaaa agacactaat gtcaaaccat agatgaatac cttgttataa gtatccacgc   1860
gataacgcta tgtaattttc agcagatttt tgtaggtata aaatctcctc ttcagtcatc   1920
atacgtagaa attttgcagg cctacctgcc cataactctc cagattttac aatcttaccc   1980
ctagtgagca gtgaacctgc agctaacatg ctgccctctt ccatcactgc acgatccata   2040
acgattgatc ccatacccac aaaggcgtta ttcccaagag tacaagcatg caatatgcag   2100
ctatggccaa tagtaacgaa tttacctatt acagtatcac catgcatgct atctgtatgt   2160
actactgtat tatcttgaat gtttgtacct tcacccactt caattttatc cacatcgccc   2220
ctgagtacgg ttccatacca tatgctggca ttcttaccta tacaaacatc tcctatgata   2280
cgggcataac ctgcgataaa tgcagtgcta tctacagacg gtgatactcc tgcataaggc   2340
accagaactt ccctcataac ttcacaacct ccagtgttct ttaaacggca cagcatgata   2400 gtgttttag cacaccataa cggagtacac caccactctt aacagatttg gctctggcac   2460
actagatgca cacatatctt gtataggact tatatattgt tgttcatgaa acgtgcgtaa   2520
tgctatggga gattactatt cttatgtatg taaattaagc aaatttagca cgtgctactg   2580
cacccagcat gttctcattt tctttaaaag gcagaccttc cttttttcgaa atagccttttt  2640 ctttaggaag cgtaatgatg tctatggcta tagtcatggc tgggaatgat gtcagggctc   2700
atgatgacgt tagcgctttg gagactggtg gtgcgggata tttctatgtt ggtttggatt   2760
acagtccagc gtttagcaag ataagagatt ttagtataag ggagagtaac ggagagacta   2820
aggcagtata tccatactta aaggatggaa agagtgtaaa gctagagtct aacaagtttg   2880
actggaacac tcctgatcct cggattgggt ttaaggacaa catgcttgta gctatggaag   2940
gcagtgttgg ttatggtatt ggtggtgcca gggttgagct tgagattggt tacgagcgct   3000
tcaagaccaa gggtattaga gatagtggta gtaaggaaga tgaagctgat acagtatatc   3060
tactagctaa gga                                                      3073
```

<210> SEQ ID NO 42
<211> LENGTH: 3786

-continued

<212> TYPE: DNA
<213> ORGANISM: Ehrlichia sp.

<400> SEQUENCE: 42

```
aaaagcttaa ggaagatgtg gcttctatgt cggatgaggc tttgctgaag tttgccaata     60
ggctcagaag aggtgttcct atggctgctc cggtgtttga gggtccgaag gatgcgcaga    120
tttcccggct tttggaatta gcggatgttg atccgtctgg gcaggtggat ctttatgatg    180
ggcgttcagg gcagaagttt gatcgcaagg taactgttgg atacatttac atgttgaagc    240
tccatcactt ggtggatgac aagatacatg ctaggtctgt tggtccgtat ggtctggtta    300
ctcagcaacc tcttggagga aagtcgcact ttggtgggca gagatttggg gaaatggaat    360
gctgggcatt gcaggcctat ggtgctgctt atactttgca ggaaatgcta actgtcaaat    420
ctgacgatat cgtaggtagg gtaacaatct atgaatccat aattaagggg gatagcaact    480
tcgagtgtgg tattcctgag tcgtttaatg tcatggtcaa ggagttacgc tcgctgtgcc    540
ttgatgttgt tctaaagcag gataaagagt ttactagtag caaggtggag tagggattta    600
caattatgaa gacgttggat ttgtatggct ataccagtat agcacagtcg ttcgataaca    660
tttgcatatc catatctagt ccacaaagta taagggctat gtcctatgga gaaatcaagg    720
atatctctac tactatctat cgtacccttta aggtggagaa gggggggcta ttctgtccta    780
agatctttgg tccggttaat gatgacgagt gtctttgtgg taagtatagg aaaaagcgct    840
acaggggcat tgtctgtgag aaatgcggag tggaggtaac ttcttctaaa gttagaagag    900
agagaatggg gcacatagag ttggtctcac ctgttgctca tatttggttt cttaaatccc    960
tgccgtcacg tataggtgct ctgctagaca tgcctttaaa ggctatagag aatatactat   1020
atagtggaga ttttgtagta attgatccgg tagctactcc ttttgctaag gggggaagtaa   1080
tcagtgaggt agtttataat caggcgcggg atgcctatgg tgaggatgga ttttttgcgc   1140
tcactggtgt tgaagctata aaggagttgc taactcgcct tgatttggag gctatcaggg   1200
ctactttgag gaatgagctt gagtcaactt cttcggaaat gaagcgtaag aaggttgtta   1260
agaggctcag gcttgttgag aattttatta agtctggtaa taggccggag tggatgatct   1320
tgactgtaat tcctgttctt ccaccggatt tgaggccgtt ggtatcactg gaaaatggta   1380
gacctgcggt atcagattta aatcaccatt acaggactat aataaaccgt aataacagat   1440
tggaaaagct actcaagctg aatcctcctg cgatcatgat acgcaatgaa aagaggatgt   1500
tgcaagaagc ggtagatgct ctgtttgaca gcagtcggcg tagttacgtt tccagtagag   1560
ttggaagcat gggctataag aagtctctta gcgacatgct aaagggtaag cagggtaggt   1620
ttaggcagaa cttgcttggt aaaagggttg actattctgg taggtcagta atagttgtgg   1680
gccctagttt gaagctgcat cagtgtggtt tgcccaagaa gatggctctt gagctgttca   1740
agccgttcat ttgttctaag ctgaagatgt acggtattgc tccgactgtg aagttggcta   1800
acaagatgat tcagagtgag aagcctgatg tttgggatgt tttggatgaa gtgattaaag   1860
agcatcctat tctccttaat agggctccta cactgcatag attgggtctt caggcgtttg   1920
atcctgtatt gatagaaggt aaggcaatac agttgcatcc gttggtatgt agtgcgttta   1980
atgccgattt cgatggtgat cagatggcgg tacacgtgcc attgtctcaa gaggcgcagc   2040
ttgaggcgcg cgtgttgatg atgtctacaa ataacatctt gagtccttct aacggtaggc   2100
caattatagt tccgtctaag gatatcgttc ttgggatata ctatttaacg ttgttggaag   2160
aagatcctga agtgcgtgaa gtgcagactt ttgcggagtt cagccacgtg gagtacgcat   2220
```

-continued

```
tgcatgaggg gattgtgcat acgtgctcaa ggataaagta cagaatgcag aagagtgcag     2280
ctgatggtac tgtatctagc gaaatagttg agactacgcc tggtaggttg atattgtggc     2340
agatattccc gcagcataag gatttgactt ttgacttgat caaccaagtg cttacggtta     2400
aggaaatcac ctccattgtg gatcttgtct atagaagttg tggtcagagg gagacggtag     2460
agttctctga caaactgatg tattgggat tcaagtatgc ttcgcaatca ggtatttctt     2520
ttggttgtaa ggatatgatt attcctgata ctaaggctgc gcacgttgaa gatgctagcg     2580
aaaagatcag ggaattctct atacagtatc aggatggttt gataaccaag agcgagcgct     2640
ataacaaagt ggttgatgag tggtctaagt gtaccgattt gattgctagg gatatgatga     2700
aggctatatc tttatgtgat gagccagcgc gttcaggcgc tcctgatacg taaccttgtc     2760
gccaagtgca acttttccta aactaaagcc tcaaatcttt attatattct gttaatgact     2820
cagtggactt ttggcagaaa gagctagttt cctttggtac aaacactttt atagagggtt     2880
ctgattaatc tatccgatgg tctaaaatca aataacata tgcaatcgtt ggctgaaaaa     2940
gctcacccgt ggtgttataa caataattcc tctccttgtt ttcatatata accttttgga     3000
aacattcctg ttggagccaa aatttctata ttttggaaac ttggcatatg gatggatgat     3060
ggctgaagta tgccatttat tttccttttg gggaggacta gagaaagcag aatagttgtt     3120
acactacttt tgaaagtaaa gtttgtagga caacccagtt aatgtggaa taaagccctg     3180 ttctttagtt ttcatgtcat aacacatatt catttctaaa cattttcct gaccacccaa     3240 tttaaagtag ttgacatccc cagaagtcac tttctctaac agaggtcaac acacttttct     3300
gtgtactgcc agacagtaaa cattttggac tttgtatgtt atatggtctc tttctgttgc     3360
aactactgaa ctcttccatt gtagcacgaa ggcggctgca gacaatatgt aaacagatga     3420
gcatgactct gatccattac agctctattt atggacactg aaatttaaat ttgctaaaat     3480
tttcacatca caaatatta tcctactttt gatattttc taacacttaa aaatgtaaa     3540 aaacaattcc taactcacag accaaacaca accaggcagt agacagaatt tgaccagtga     3600
gctatcattt gagaccctca gttccacatt acttttagag aggttttta aatgtcactt     3660 cttagcatct aaacaaatct atttacatat ttatattact tctatagtgt catgtgctaa     3720
aatttaagct cttgtattag tccgttctca cactgctata aagacatacc tgagactggg     3780
tttcac                                                               3786
```

<210> SEQ ID NO 43
<211> LENGTH: 3735
<212> TYPE: DNA
<213> ORGANISM: Ehrlichia sp.

<400> SEQUENCE: 43

```
aatgcgctcc acataactag cataacgttt tcagcaacgg cagatcttca tatataagca      60
ctgaacacct acgttccaag atcatgctct tcgcgcctgt ttacttggtg gctcagagtc     120
atcatcacta ggagttcgtg gtctgtgaga gctaacttgt gcttcttcca gcgtataact     180
agcacctccc aatcctgatg ctgaaggttg atcccacgaa taaggcataa tcccttgatc     240
ctgaggtggc atagggag cttgtgatct tcccattcca gtactagtac ctcctagccc     300
agatgttgag aattggctag atggataagg aacattctct aggacacgta gtataatatg     360 agggggggg ggaacgagtt gagctccctg tccggcagta cctcccaatc ctgatgttga     420
gggttgatcc catgatgttg agggttgatc ccacgatgtt gaaggttgtg catacgaata     480
gggcatcatc cctggatcat gtggtggaat atgcgaagct tgttgacttc ccattccagc     540
```

```
ggcacttcct aaccctgatg ttgagggttg atcccacgat gttgaaggtt gtgcatacga      600
ataggggcatc atccctggat catgtggtgg aatatgcgaa gcttgttgac ttcccattcc     660
agcggcactt cctaaccctg atgttgaggg ttgatcccac gatgttgaag gttgtgcata     720
cgaatagggc atcatccctg gatcatgtgg tggaatatgc gaagcttgtt gacttcccgt     780
tccagcggca cttcctaacc ctgatgttga gggttgatcc cacaatgttg aaggttgtgc     840
atacgaatag ggcatcatcc ctggatcatg tggtggaata tgcgaagctt gttgacttcc     900
cgttccagca gtaccccca ttcctgatgt tgagggttga tcccacggcg caccataggg       960
tatgggtata cgctcaagaa cacgtagtgg gacactgata gcttgtgctc cttccactcc     1020
agcactagta ctccctaatc ctgatgtcga gggttgacta ggtgcagcac cggtctgctc     1080
aacagcattg aaatatcttc cgtatttctt gtcacaaata ttcatcatta ctgaaagata     1140
ccgcaatgct gtattgcgcc acttgacttc tatctgtgga attaatagcg catcttccgt    1200
aatatgctca ttgatctcct catagacatg gcacatgtct aaaaatgatt tgcgagccct    1260
gtatgccccg agctcccttc ttctgctata taaagcacac aaaatctgga dacaatgccc   1320
aatcctacct gcaacaacat gatctacatt accggtggaa gcgtatactc tatacatcaa   1380
gaacaaacca cctactgcat gcactaaagc accaccccga tacctttctc gcttgagtcg   1440
taaatcaaaa ctgtgaactc ctaaaccttc aacatatgcc tctaaatagt agagaaaatt   1500
tgccatcgct cttctagaga gtcctagacg caggcgtgca cttccattat tacgtaccat   1560
cgcttcacat gcagctgcac tagtctcaat agcatcaata acactgtcca agcaagcctc   1620
tgtacgatga cggaaaaaac gcggtgtatt aggctcaact aactcagcaa ccttactgca   1680
aagctctatg ttatgccgca ctacgcgcaa aatcgccttt atattctctg tttcctcaga   1740
atccaaagaa gaatttaagc atctacttaa ggctgaaaat tttacatagc agtatgcact   1800
taaagctgtc actgtatgag atgcactacc atctctacgc tcactactca ctgcaccagt   1860
aaacctcgtg gcaatagttc tggcacagca gttcactata gcataacat tcactatgat    1920
agcacatgcc ttgcctattt gtaggtgtgc cttacgctta ataaagtctt gatccatgaa   1980
cagcggcact tctttgttgc actgcgccgt gatgcagtcc tgcaacgcgt cgtacaaccg   2040
attgatcaaa ctatacaaca ccccggttc tgcgcttgaa gcaccttctg cagcagttat    2100
acagctgtta atactgtcta tcttatcagc tgccgcaaac acgacatcta caccccggag   2160
cttgacaaac gtatcgcgca attccagcat acattgacgt atagcctgca ggcatgcagc   2220
atatggcctg gaattagtca ttattgaatt acatacagtt tctttatatt ccgcagaaga    2280
gcaaccactg taggcatatc cagacataac tggagtagtg aatatacgag gcatatgcat   2340
ctaattaacc actggaacaa cttcacacct tgaaagtgta gcataccggt gtgacgcagc   2400
tcaatattaa agattatgca cttcgtgatc gtctactagg aggctcaagt tcatcatcac   2460
taggagtttg tgatctagga gagactacct gtgctccttc cagcgtagaa ctagcacctc   2520
ctaatcctga tgttgagggt tgtgcatacg aataatcttg caacgaccaa caaggtgcct   2580
gagcttgcag tgctccctgt ccagcaggat tacctcccaa tcccgatgtt gagggttgac   2640
taggtgaaga gggcatatgc cctggatcat gaggtagcgt ataggaagct tgtgatcctc   2700
ctattccagc cccagcactt cctagtctag atgttgaggg ttgactaggc gaaccctcag   2760
tctgcctaat attattgaaa tatctctcgt acttcttttc ccaaatacca atcattgccg   2820
aaagataccc caacatagca ctacagaacc caacttctgt ctggggattt aatagtagac   2880
```

```
ctcgcgtaac gcattcctga atctcatcat agacagtaca catgtccaaa tataattctt    2940
gtgccgtata ttctgaagct cccgctcttc tgaccttata tttatagaga gtaagcaaca    3000
tttgaagaca atgctcaatt ttactcgcaa caacatgccc tgtattaccc gtggaagcat    3060
atactctgtg cattgagaat aaactaccaa ttgcatacac taaagcttgc acatacttgt    3120
catgcctgaa acttttaaaa gcaacgctca gtcctaaact tttatatgtc ttgaaatggt    3180
gtaaaaaacc tgttctcgct tttttagcga gagctaggcg gttctttgca ctatcgttat    3240
cactcaccat ctcttcgcat tcagccgagg tagacccaac tgcatcaagc atactgttta    3300
agcaactcac cgtacgatca cggaaacaat atggaatctc cggatcaact agctcagcaa    3360
ccttattaca aagctctatg ttatgcctca ccacacgtag aatagccttt ctacgcttag    3420
tttcctcagg acccggagaa taatttaaac atctgcttaa agctgaaaat tttgcattta    3480
cgtatgcact aaagccatg ttggcatgat acgcactatg ctcatcagcc tcacctattg    3540
cactgtcaga cgcctcggtt aaggttgtga caaagcagct tgccatggta atagcattca    3600
ccaggatagc atacccttta gcgatttgta ggtgtacttc acgcctcgtg aagtctggat    3660
ccatgaaccg cggcacttct tgttgcact gcgccgtggc acagtcatgc agcatattat    3720
atgcactatg gatta                                                   3735

<210> SEQ ID NO 44
<211> LENGTH: 2322
<212> TYPE: DNA
<213> ORGANISM: Ehrlichia sp.

<400> SEQUENCE: 44
aatgtataca gtctcagatt cagaatctat aacttctttc gttactccac caatgttaat      60
ggcgaatatc tcatcgacta agcgttcagg atacttgcta tcattgtcgg tagagccatc     120
tgactttttt accgtgacat tcttttaaa agaaactcca tttacaacgg acaattcagt     180
gccattttgt agcttcgagc gcaactccac agcaaattca cgtatttct tcatacgtaa     240
tgcactcttc cattcttcag taagaataga cctgctttct tcaagtgtcc ttggtcttgg     300
aggcactact tcagtaacaa gaacgccgaa ataagcgtca ccattgctaa ccagatgaga     360
cggttttcct acggcagatg aaaacgccaa agtagtaaag gcgtttatac caagctgcaa     420
cggaaagtct ttcactaagt tgccagattt atcgagccca tgcatatcaa aattcgtcaa     480
aacaccactg atccgcgcac caaacatatc ctttagttca ttcagcaatg ccccgcgggct     540
gatcatatcg tttgcttttt tcacattgct aactagcaac tcacctgcct tttgccttct     600
aatatttgaa gatatcttct cttcagctt ttctaggtct tccttagtga tctcatgctt     660
ccttattacc ttcatgatat gccagccgac aacgctacgg aacatttcac tgacttctcc     720
ttcatttagt gcaaacacca catttcgcac acctaccgga agaacatcct tagagatatt     780
attgagtgca atatcctcta tggtgtagcc agcatcacta accaattcct caaaagactt     840
accctcttgg taagctttgt aagctagctc agcttcattt ttgtctgtaa atactaaatt     900
tagaacatct ctttgatcat gtagttcact gttttttaatc tcaacgtcta cctcttgatc     960
cgaaacaatg acatcagcaa gcaagtcgtc ttctgccatg attatataat cagcactgcg    1020
atattcaggg aaatttagag aattcttgta ctgctcctca acaattttt gcaattcatc    1080
atcagatata tcacttcctg aaatgtctac ggcatcagaa gatatttcca ctatgtctgc    1140
cacacgatgc tgcagcaatc ccaacacaac atcttttgct aatgcatcat aataaggaat    1200
atgtaattcc gccctattag ggaataaaca ctccattaga atagtagaag gtaaagcatt    1260
```

-continued

```
gcgaatttta ttcacatagg acgactcagt cattccgctg tcagccaata cggcttcata    1320
tctctcctgg tcgaagacac cattagcatc ctgaaatatt cttatatttt tgatcagact    1380
ccgtaagcta tttgagccaa cacgtatgcc taagtcatga gcaaactttt caacgaccat    1440
gtcggctatc atgttcttga ggacaacttc cttaatacca aactgattaa tttgagcatc    1500
agacaatttg tgttgtaaca tcttctctag ttctgccaac tcgttgcggt acattatacg    1560
gtaatcccgc aatggtagac atttattacc caacattgca acgcactgtc cgttgccaga    1620
attagacaac ttacccattg gtatcatgct tccaaaagtg acaaaagcca tggcacctaa    1680
aaccgttgcc atgaccaccc aaacataaat cttccttgat cgcataacag aacgcccata    1740
gctggtcaga ttcccgaagg aatatagtaa tcagaaaaaa tctgcaagac tttttctagt    1800
tgtttatggg caatattctg aattttgcat agtagccatt acgtaatgta tggatagacc    1860
cgtattaatt tgtttcggta cgatatatga agttctaaaa agctatagaa ccttgccatg    1920
caaagcttaa gagcccttac ccatcccata tacatccgtg ttaatgaaag caccattctg    1980
ctgcttgtgc agaattctac ataagcatct cgtgccgctc gtgccgaatt cggcacgagg    2040
aattagattt aatagcagaa gagcagaggc actgtggtga ctgaagcagc aattaaagta    2100
atgtggccac agctaagtaa tatcagcaga cactgaagtg ggggaaggaa ggaacagatt    2160
gttacctggg catgatcaaa tttctggatt cagaaaagtg tggatgaaat cctggcttta    2220
ttattgatca gtgctgtgtg atacagcacc tagtcctcaa actctttctt cttaagcatc    2280
cacacttgca aaatgtgcaa cttccaatat ccatctctaa gg                        2322
```

<210> SEQ ID NO 45
<211> LENGTH: 2373
<212> TYPE: DNA
<213> ORGANISM: Ehrlichia sp.

<400> SEQUENCE: 45

```
gcaaatattt ttcttggtgc cgccctaaaa gcctgaaaaa tttaaagaaa tgttactgct      60
ctagtcattc ataaaatgca aatagcctac agaaggagta tttactgcta taggcttgaa     120
agtgcaatcg ttatttacta tttttatac atatcgcagt acagagattt tacgcgctac     180
gcctgtgcat catagccgta ttgcatcaat aaattgtcgt tgctacgcgg gaaagctgct     240
tagcgcttga ccattttca tacacattgt accatcatag cgagtgtggt gctcatgaga     300
gtgcgtagtg ttgccgccgg tttctcatgt tataatcttg ctgccgtttt gtgcagaagg     360
aggagtagtc tcgtttttttt ccaaaagaca atgtgctgga gtgtcccggt gagcctcaag    420
gttcttgtgg gatttgtgtg ggctgttgta taaataccac gttcgaagct gtcctagtgt     480
aattcagcat atgttgagga agttgttgct atgaggttga tggtatggcg aaaagattct     540
taaacgacac agaaagaaa ttactatctc tgctcaagtc ggtaatgcag cattataagc      600
ctcgtaccgg ttttgtcagg gctttgctaa gtgccctgcg ttctataagt gtagggaatc     660
cgagacaaac agcacatgat ctatctgtgt tggttacaca ggatttcctt gtcgaggtta     720
ttggctcttt cagtacgcaa gctatcgctc cttccttcct caacatcatg gccctggtag     780
atgaggaggc attaaatcac tacgaccgcc ctgggcgtgc tccaatgttt gcagacatgt     840
tgaggtatgc gcaagagcaa attcgtagag gtaatctgct tcagcataga tggaatgagg     900
agacatttgc atcttttgcg gatagttacc tcaggagaag gcacgagcgt gtcagtgcgg     960
agcatcttcg ccaggcgatg cagatcttgc atgcaccggc tagttatcgc gtcctgtcta    1020
```

-continued

```
caaattggtt tttgctgcgt ttgattgctg cagggtacgt gaggaatgca gttgatgtgg    1080
tcgatgcgga aagtgcaggg cttacttctc ctcggagctc cagtgagcgt actgctattg    1140
aatcgctcct gaaggattat gatgaagagg gtctcagcga gatgctcgag accgaaaaag    1200
gtgtcatgac gagcctcttc ggtactgtgt tactctcgtg ccgaattcgg cacgagttga    1260
aaagcagcct ttttaaggta gacatcctgt atatgattta agtctcacct cccaatggaa    1320
tcatgaaaca gttagaaaaa taatgaacta cgtcttatat aatctttatc gctactttaa    1380
aaatgagtaa tatattcaga tttagtagaa acatccctga ggaacaattt gttttcacaa    1440
attacattgg ttcctcacat gcaagattat taagcattaa ggaggaggat attggacatt    1500
gtataccctg taggaatagt tttttatttt cagaaataag ctcagcttac tgattgatgg    1560
caaagatagt tgatgataaa atagaaaaaa acaaagttac tcttcttaat tttgtactct    1620
tcttacctcc tttcattttt aattggttat aagtaggtga agttaaaac ttggcaatgt     1680 ttgctttagg agttattaca attactcagg ttagtagtat agttatacgg tcatctttag    1740
taaaacatca ttcggagtca tagtcacact tatgaatatc acagaatgga tatgtgactt    1800
tggggttttt ttgtgggata ttttttgaga tatttaaggc agaagtgcca cctttacttc    1860
atttattttt atccgccccc cccccacccc accgtttctc agaaaggata aggttttcac    1920
agtaccagag acatttatct actaaaactt tgaactaatt aaaatatata gggccgggtg    1980
cagtggctca cgcctgtaat cccagcactt tgggaggccg aggcgggcgg atcacgaggt    2040
ccggagatgg agaccatcct ggctaacacg gtgaaacccc gtctctacta aaaacacaaa    2100
aaattagccg ggcgaggtgg cgggcacctg ggtcccagc tactggggag gctgaggcag     2160
aagaatggcg tgaacccagg aggcggatct tgcagtgagc caagatcgcg ccactgcact    2220
ccagcctggg cgacagaaca agactccatc tcaataaata aataaataaa taaaatatta    2280
tttaatttaa gagagttgaa atcattgaat tgattcattt aaacaaggta atttgcaatg    2340
ggtctatttt taggctattt tctttatagt agt                                 2373
```

<210> SEQ ID NO 46
<211> LENGTH: 7091
<212> TYPE: DNA
<213> ORGANISM: Ehrlichia sp.

<400> SEQUENCE: 46

```
cctatggcag ctctaaactc ggcacgactg gtttctacaa gagattggtc gacattaaac      60
catgcgaaat cattgcgatc aattcttcct tcttttttcct gtatagcact acagacttcc    120
tctgcactag aagccactcg tgtcccgatg cgtacgtcac ggatgcaaag ccccaggtct     180
tttacgctgc cgggtgtgtc tatatcttcc acaacataat caacgcaagc gtgaatatgg    240
ataccagaaa cagaggtaac cctgtatact aaatgctctt ccaaaacatg ttgattaaca    300
ggtaagcgcc tagcactatc accattatca gcaacaacgc cttcatgcgc aacgtaatga    360
gcagcgagct caactggcag agatgaccca ctactgttac tcaagatact agataagagt    420
acccggagat ttctgtgtt tacaccagtt ttctccacaa tatttgcagc atgcttcggc     480 tgtgaccttta agatttcacg tatttcatcg gagtgttgta tgaaaatacc acagtccccca  540 cgcacaggta cagagtgaga tgcccagcga tggcgcttcc ccagatcttc ccatagcgaa    600
aggccgtgag ctactatttc ctcagcaaga ttgaaaatgt ggcctccggc aaaatctgta    660
tcttttgcac tgccagcgag gaaatctcta agtgatatac cgcctccaag tgtaagtaca    720
ttgccaaatg tattcacagt taccgccaca tgacggagaa tagtggcgca tgcatcgtgc    780
```

-continued

```
gcctgagagg ccacaaagga catgcagacc cccattttgg atacagcatc cctgccatga      840
gaaacagcgc cctgctgtac tacactagat ttatcgtatc ctaccagacc aacaacgcct      900
cgtacaacta ctcggaatac accgctcgct tcttgactga ttactgtatt acaaaaagaa      960
agctctagga cttctagcgg cataccgcta ataacgctgt aagctcttag gatgcattca     1020
tcaatatcgc ttacatcgta aaaaccccta cgagccatgt aacgtgggtt atgcctctgc     1080
agattacacg cgctgtacaa tacatgagta ggcttctcag ggactctcac atagtgtttt     1140
gccagagctt tgggaatatt gtgccaagaa catacagatc caggctcgcc ttgcctaacg     1200
tcgcggcaat ctctctcagt aagcacgagc tttactttt tcacagctgt acggtaaaca      1260
ccctccgcct ttgtcgatgg agcaatgtca tactctaccc acatcttaac tttggctatg     1320
ggtacaccac tgttgtcctg aatactaaat atgcatgatt cgtgtactgt cagagcaccg     1380
ttcttgtagc tactaggtgc tgaagccaat aaagaatgca ccctggagaa agtagtataa     1440
ctctgaactt caaatgtggt agagtcctct tctctgacta ttgtcatatc ttcagacacc     1500
ccatccaggc atccaagaac aaaattagtt aaatcctctt cctggttttt tcctggcaag     1560
ctgttatagg caagtgcaag ggcatgccac agctggaaag gtacttgttg aaggcagta     1620 ctgttactcg ctgtcttatg cagagctctt gctaataaat ctggggaagt tagattctca     1680
tgtatgagtg caggaggtac cgcactgccc tcacgtagag taaacccctc tgctaagagt     1740
atgaccattc tgcgtcgtgc aggatgactg ttccgatcac gacataaaaa gaaatctatc     1800
gcgctaccaa gcagtgcaac ggacgctttc gatgggtttt gcttaagcag cagagtcatg     1860
ggtgcctcat cttagttact tctagtgaca aagcggtact tttattcctg taaggacaga     1920
aaggcctgtt ttttccaga aatctacgcc ttacatgtat ggaaacctgc gcatccagct      1980
atagatatcg caaggcatag tgtgcagaat acggagctgt agcaggcgct cttaccccc      2040 agcaaagtac gcaaacctag cgacgactcg ttctcacacg ttgtgaacat acgtagtaac     2100
acaccttgac gtacctagcc tacaccacta gacatatagt gtaaaacaaa agtaccaga     2160 tccccgtctc aggggttgta aaagtagcac attggaaacg gactgttaag tatttatatt     2220
actacttagg ttcagaataa acattcgaat tgtaatgcac cataggttag taatgcacta     2280
tgagtgagaa attacgcgaa ttggtactgt gcgatgatct tgaaatttac agttgtagac     2340
acggcgcatg cggaagatat aacctctcaa accctgcaga ggttttacta atcatatgtt     2400
ttgtctaata cctgcccaca aaaacatat gaaagccttc gtagctcagg tcggttctct      2460
ggctgttttc atctctaggt tttaattccc aagaattcga cttttcgcgc tacctaagca     2520 ttttttaatca ccgttgacta ttagagacga tataataagc tacattgatt atctgaaata    2580
tgtgatcctt ctaaaaatct ttaggtgctt tagaagaagt acatattacc ctctatggca     2640
acaacattga taatttaggt gaagtgtcac agcgtttcat tatgaaaaaa agggatactt     2700
atttatgggg aatggcacct tatgcaatat gagccttagg gattgccaca gtgttttggt     2760
ttcacagcat gagtaaggac gtggttttt agcaagtatt tattgtgcta tgtgtgtaaa      2820 agtaacata tgaagatcgc taaagaattc acactagaaa taagttgata cctgatgatg      2880
tagtataaag gttgagcaat agtctttttt tgactgtaaa tcccgcatgc agctttatgt     2940
gtgtttatcg caaaaagtgg gcgtttgttg caataaaaat tgaaatgcca actattattg     3000
cacataccgt gctcataccc ttaatcttgt agatgcgctg taatcacaat tcgcatgtgc     3060
agcaaaactg taatagatag cttagcacag ggacgaataa tccctagatt ctacgctgcg     3120
```

-continued

```
ggctagtgct ttttttagca tctatacggg agtatctttg atatgataaa cacacaacag    3180
catgatgctg tgcttatata gcattggtat atattctgcg atgcggacta atcaatgttg    3240
taatcaagta aaaaatgctt ttttgaaccg tatattgttc gtaaggcatg tattactcag    3300
ttgtcgtact acaaattcct cttcctctag agcatgcaag tatgaataca gcttatgtgt    3360
gcgatgcgta gattactaat gcatgattag tgtagggtat gctgtatttt ttgcatgcgt    3420
tttagatatg ttacgcaaca catgttttc aaggacgctg tggctatcac ggatatgata    3480
gccacaatgc gctgctctta ggtcaactag gatgggctgt gggtttatgc atattaagca    3540
gtggctcctg cattcaaagc tattctttgt tgtggttaac aatcaaaaat agagagtagt    3600
ttgtttataa gaagatatgc aaaaaacctt tttatccaca gtaagcccca ggcgtatcga    3660
tgcacaagga tccaccatgg ctatgtctta aggatgtacc cagaatatga tcgtatctca    3720
ttggctaagc agagcgtcct ccagtttctg attctacaga tagtacatcc tgtaatgaag    3780
aaatggatcc ttcatcaagt gtcgttgatg gagcatcatc cggacagtac tttgtagtag    3840
tgctctcgga gttcagatca tcgcttgtac ttacatcatc atatgacgaa gaaacatcaa    3900
tcgtagcatg ttcgggttga ggctctgcca gatgcacttc ctgagagagg aggtcatgat    3960
ataaatccca cagatagtgc tgttttttaac caggtccctg aaaaactctt ctggagaaac    4020
tggcagagga gccattgcgt actgcagttt ggtaatattc atgcctatgc aagggatgcg    4080
ttgaacgcga acaagtgtag gatctggtac gcgcgtatct tgaggagtaa agactttccg    4140
tttatagaac cgatgcttca atctgagtag aagacgtcct aacggaggac atactctaaa    4200
cagtaatggt ggtgaggtct ttatattgca gtctggtgga gtgatgattg tcaggtttaa    4260
tgaacagtta tcatagagaa ctcgtccctc tccttgtata gagatctcgt atttcagtgc    4320
tgtgtttact ttgaacgcag gagtcttttc tccctctgta gactgcggca ctttcaggag    4380
aaagtccaaa ttctcgcaga ctgcaatacg ctctggtgtt attgcatcta cctgttttat    4440
attgctacac gctgatacat agatgcgatt tagtagattt agcgtggcac ctgcatcgct    4500
aaagaagtat tctttatcca aagcatgttt tataggccaa attacatcga aacataccca    4560
ggctgacagc cctccttgat ggcaatggct tgctatttca tcaagcagtc taatgtctgg    4620
gacgacccca tgacgatcat ctcggaacat tttttgcagc atggctatcg cgagacttct    4680
ttcacgatag cggcgcaaaa ataccctct acttactcca tatgttctct gacatacaag    4740
attaaggtta gtgatgctcg acgattttat gctccttct agtcttgcaa tatgagcact    4800
tacattttgt ctagggtaaa atgttttatt gatgcaccag tcacatctat gcatatcgat    4860
tagaaactga tggccgtaca agttagactt gtttttatac gaatcgcaaa gtgcgctgtg    4920
gaaggaaaac cccgatgcac cttccagcca ttttttcttt tgagaatact ttaaacttac    4980
atctatagaa gggcgatgat ccttatgctt agctttacta tccttacttg cgtcagagct    5040
attgtgtgtg cagatatgta ctgaattagc ctcatcttct gccttagaga cagcactact    5100
agatgttgaa aaaattgaga ttatcctaaa aaacagtgct ctcaaatagt tcaggatacc    5160
actgacagtt cttctagatc cattgtgagt attcttttta cgcaacttaa acctccatgt    5220
tacacaatat gcagctttgc tattttcctt tctcatgtgg atgcgctaat ctgcgtttga    5280
tcagtagtaa cgacgcgcgc tgtagtgtag ttgttccaac aatgaacatg caaaattgct    5340
gcaatactta acttcctcct tctgaaatgc atttcccaca tttcaggctt ttactatttc    5400
atgctttaca tcgtgtagcg cattttttgaa aaaacaagat attagtacag catttctggt    5460
aaaccagtaa ttgttcctat tcaaggtctc tgaatcatga cgaccacttt ctttgcggca    5520
```

```
attgagaaat tcctcacata tttgatatac accgcacttt ttgttttgc tccatgaatg    5580 gattaccgga tccaagggca ttgctatact tcactgtgca acactactgt aagtgtcgtt    5640
agcatatcat gaaattatta ataatatgt agaatatgtt gtgcaaaaga cgcttataac    5700
aacttaatag tgaatttcat gaaatttgtg agtagttttc tatcggaata cgtgttttag    5760
caacgctata gatggggtaa gatcgctttt atgttcagaa attcgcaacc atactatttt    5820
ctctgtatgc gaagacatgt cttagcgtca agccacatat gtggggtact taagcgttgc    5880
cttgcacgca acagctccac attgcctgga ttttttctta catcagctaa ttatatacca    5940
gactcacaga tatactacgc gtaaccagtc atattatgca gcacctgtac atgttctctg    6000
gggagttcct ttatgaaacg agacattttc atggattggc tccagttatt gatttctctc    6060
attgcagcac atgatatgta tagctgctct ctagctcttg ttatgccaac ataggctaag    6120
cgcctctctt cttccagagc gtttccagtt atgtcattca tggattttc gtgtgggaag    6180 actccttcct cccatccggg gaggaaaacc aacgggaact ccaacccctt tgcggcatgt    6240
aatgtcataa cgtgtacgta gttattgtct tcttctaaag aatcattttc tgccactaag    6300
ctaatgtgtt ctaaaaactt cgacacatca tcgaatcctg atacggctga aagagttcc    6360 tttatgttct ctattcttga tagacctgat tccccgtctt tttttagaga ttctatatat    6420
ccagagtcat gagcaatagc ttttagtaca ttgacggatg aatctctact taacatttct    6480
ctccaatcat caaactgctt gagaagatct tgcagaatgt tggatgtatt atcagatagt    6540
aatccatctt ttatcattga gtgtccggct tcagttaggg aaatactgtg ctttctccca    6600
tatgcacgaa gcttattgac agtagaagtt ccgagcttgc gtttgggctt atttataatt    6660
ttctcaaacg ctatgtcgtt attggggttg actactactt tgagatatgc aacaagatcg    6720
cggatttcta ccctatcata gaacttggtt ccgccgataa ttttgtaagg tataccatat    6780
cttacgaaga actcctcgaa gactctagtc tgaaagctgg ctcttactag aacagcagtt    6840
tcactaaatt tataatcgta agagctctta atatgctcac taatgtattg agcttcgagc    6900
cgtccatcga agaacttcat taaaccaact ttttgtcctg cctgattgtg cgtccataat    6960
gtttttttaa ggcgggattt attattatca attatcgctg atgctgaggc taatatgtta    7020
gacgttgacc tataattaca ttccagccct attactttag cgtctgggaa atcatctgaa    7080
aatctgagta t                                                         7091

<210> SEQ ID NO 47
<211> LENGTH: 3947
<212> TYPE: DNA
<213> ORGANISM: Ehrlichia sp.

<400> SEQUENCE: 47
ggtatatcga tagcctacgt agtcactcct tattattaaa aaggaagacc aagggtatta     60
gagatagtgg aagtaaggaa gatgaagcag atacagtata tctactagct aaggagttag    120
cttatgatgt tgttactggg cagactgata accttgccgc tgctcttgcc aaaacctccg    180
gtaaggactt tgttaaattt gccaatgctg ttgttggaat ttctcacccc gatgttaata    240
agaaggtttg tgcgacgagg aaggacagtg gtggtactag atatgcgaag tatgctgcca    300
cgactaataa gagcagcaac cctgaaacct cactgtgtgg agacgaaggt ggctcgagcg    360
gcacgaataa tacacaagag tttcttaagg aatttgtagc caaaacccta gtagaaaatg    420
aaagtaaaaa ctggcctact tcaagcggga ctgggttgaa gactaacgac aacgccaaag    480
```

-continued

| | |
|---|---|
| ccgtagccac ggacctagta gcgcttaatc gtgacgaaaa aaccatagta gctgggctac | 540 |
| tagctaaaac tattgaaggg ggtgaggttg ttgaaataag ggcagtttct tctacttctg | 600 |
| tgatggcgct tgaactccgg gtatgctggt gattttgagg tattgggagt tataccgcaa | 660 |
| gtatataact taaatactgc atcgtaagga tatccttctg tttctgagac actggtaagt | 720 |
| atgcccatta cctatgaatc tctatgtaga tgtaataaga gcatacacag taactcttat | 780 |
| tattaaaaac aagaccaatg gtataaggga tagaagaaga gtattattag agaggatgaa | 840 |
| gtagatacag tatatctact agctaaggag ttagcttatg atgttgttac tggacagact | 900 |
| gataagctta ctgctgctct tgccaaaacc tccggtaaag acatcgttca gtttgctaag | 960 |
| gcggttgggg tttctcatcc cagtattgat gggaaggttt gtaggacgaa gcggaaggct | 1020 |
| ggtgacagta gcggcaccta tgccaagtat ggggaagaaa cggataataa tactagcggt | 1080 |
| caaagtacgg ttgcggtttg tggagagaag gctggcacaca acgccaatgg gtcgggtacc | 1140 |
| gtgcagtctt taaaagactt tgtaagagag acgctaaaag cggatggtaa taggaattgg | 1200 |
| cctacttcaa gggagaaatc gggaaatact aacacaaagc ctcaacctaa cgacaacgcc | 1260 |
| aaagctgtag ctaaagacct agtacaagag cttaatcatg atgaaaaaac catagtagct | 1320 |
| gggttactag ctaaaactat tgaaggtggg gaagtggttg agattagggc ggtttcttct | 1380 |
| acttctgtga tggtcaatgc ttgttatgat cttcttagtg aaggtttagg tgttgttcct | 1440 |
| tatgcttgcg tcgggctcgg tggtaacttc gtgggcgtgg ttgatgggca tatcacaatc | 1500 |
| cgttgggctt cgaccctata tgctcacagc aagtcactag gcaaaattgg agctgcatca | 1560 |
| ctccgaaaca gactacgatc agcgattctc cataccctagt agatcagtac agtggcttta | 1620 |
| tactcttacc cagcatgaaa tacttgctat ctaagaatct cctctaaaac tttccagagg | 1680 |
| ttatctgtac ttcgagagga agctaatctg cgactaatac ggatggtgtt tataatatca | 1740 |
| ctcctaaact tgcttatagg ttaaaagctg ggttgagtta tcagctttct catgaaatct | 1800 |
| cggcttttgc gggtggcttc taccatcgtg ttgttggtga tggtgtttat gatgatcttc | 1860 |
| cggctcaact acctacaaat tgataggtac actaaaagcc cacgtaataa ctctcattat | 1920 |
| taaaatgagg aagatgaagc agatacagta tatctactag ctaaggagtt agcttatgat | 1980 |
| gttgttactg ggcagactga taaccttgct gctgctcttg ccaaaacttc cggtaaagac | 2040 |
| tttgttcagt ttgcgaatgc tgtgaaaatt tctgcccta atactcgtgc cgaattcggc | 2100 |
| acgagcggca cgagctatat ttaacttata agaaatcagc agactatttt tcaaattgat | 2160 |
| tgtacaattt accttacctg ggaatatatg tgagaaccct ggcttctcta ccttttaaca | 2220 |
| atatttgcta ttattatttt taaagtatta gctattgtgg ttatgtggaa ttaaatatca | 2280 |
| acttggtttc aatttgcatt ttcctaatga ggaatgctgt tgactacgtt ttgcatgtgc | 2340 |
| ttgtgggcca tttatgtatc ttcattacat ttgttaaggg atcgtgtgag acattcattc | 2400 |
| attttattt tattgtcatt ccattacttg ttaactcttt ctactagtct tttaaaataa | 2460 |
| tgtttaattt atcaccttt tatttatggc tttctttct tggccttgtt ggacagatat | 2520 |
| ttttcctacc ccacatcatg aagacagtcc cctatgttct tgtttgtttg ataaaatacg | 2580 |
| tagactttaa ctcttgaatg agatgcataa cttacctcaa attaagtttg tgaatgttag | 2640 |
| taggtagagg gcaacataca aattgtatat gaatatattg ttgttccatc atcattggtt | 2700 |
| taaaaaattc ttaattctcc tgatgaaatt acttgggatg tctgtcaaat aaatcttaaa | 2760 |
| atactttttg ttaattttta ttaagtagtg tactgaaatt aaattggaac tggttaaatc | 2820 |
| tatagattgt taaattgaat atataaaggt taaattgaaa ttcattcaat tcatgtactt | 2880 |

-continued

| | | |
|---|---|---|
| cttaaatttc tatcagctaa ctttttataat ttttggtata gaaatcatac acaacataaa | 2940 |
| aaaatactaa gtattttatc tatttttgat acaaatgtaa attaaaattt aatttttac | 3000 |
| tgctaatatt acttatttaa aatttttaact cttaatcatt aaatatctct aatatcacat | 3060 |
| atatatttca atgtatataa ttataaagta acacttcttc cttgtcaatt tgtgtggctt | 3120 |
| gtactaaatt gtattaattt ttctttattt aagatgtctt tatttcctct ttattcttca | 3180 |
| ataatatgtt ctctggaatc aaaatcaaga tttacatttc ttttatttct acacttgaga | 3240 |
| gatatggtgt cagttcttcc tggtttccat gatttccata gttcccactg ttttcatgaa | 3300 |
| atccactgtt aagcaattta tccccttttat ataaagtgtc attttttttgt tgttactttc | 3360 |
| tttgttgtat ttagttttta gaaatttgat tatgatatgt tgtagtgtag atttcccagg | 3420 |
| tgttttcttg tttgatgttc tctagtttgg tggctacctt gttgaatcta taggttttttt | 3480 |
| tatttacact taactaaatt tgagaagttg tcagccatta ttttcttaaa ttacttttga | 3540 |
| cttttttagc ctctactatt tctatttctt tttttgaggc tctgatgaca tggatatgag | 3600 |
| gtcttttgtt ttagttccac aactcgtgcc gctcgtgccg aattcggcac gagaaaagga | 3660 |
| caaatgttgt acagtttcac ttacatgaga tacctagcac aggcctttc ataggggaaag | 3720 |
| tggaatagag gttaccagag ctcagggcat tgggaaatgg ggagtattgt ttaatgggca | 3780 |
| cggagtttct gtttgagatg aggaaaaagt tctggaaatg tgcagtattg tacaagctca | 3840 |
| caaattgtac taagctcatc aatttaatgt taatgccact gaattgtcta cttaaaaatt | 3900 |
| gttaaaatgt taattttcat attgtgtata tttgaccaca gtttaaa | 3947 |

<210> SEQ ID NO 48
<211> LENGTH: 5521
<212> TYPE: DNA
<213> ORGANISM: Ehrlichia sp.

<400> SEQUENCE: 48

| | | |
|---|---|---|
| ttcacctggc caaatcttat tggatcttca ggacaaagac caagaatctg cttctccaag | 60 |
| aagcattctc tgaccccccac ctacctatct gactcttagc ttagattcct aatggtgtga | 120 |
| gtgtgtcaga gcctttactt agtctaagcg taactgtaaa aacatctttt caaaagtctc | 180 |
| tgcatgactg tctaggtctc acctatcaca ctgtaagcat ctggaaaaca aagccactga | 240 |
| gtcttccttt taccaaaaag gcctagcctt gttttttgaca aatggcaaga acacattaga | 300 |
| tgtttgttga gagaacaaaa ggagagaact cattatgaaa ctctggacaa catttatata | 360 |
| cctctctaca ttttttgtgt tggaggttag ttttcttttc taataatttg atttctttgg | 420 |
| atacatcgag gcaatacact taagaagcaa gaagattggg gccagccttc tagactgttc | 480 |
| aaagggttac acccaacaga agggaaatat tcccgagatg accttggtgc ctgttggggt | 540 |
| gatcaagccc aacaccaggc cgtcgggggct acaaagtcca gtggggtcaa aggaatgaga | 600 |
| aaagacaagt taagagtgca taaagtgtat ccaggggggct aacgctagat tggaggctgt | 660 |
| gaaggcccgg agctctggga gcccacacta tttattgctg gagtagaaag gtagcagtgc | 720 |
| atcaagtgta gctgtgacag tttagcatttt tctttgacac atatagaata tgctctgctg | 780 |
| cttgatataa tggagagcat gtttatgagc ctggagagag aaccaacaag tctgtgcaca | 840 |
| ttccagaggc tacgaggggc tttatgccct gagccctgga ttccatccaa gccgcaaggg | 900 |
| gttttatgcc ctgggcttag atttgtggcg tggcagtgca gccttccacc ctttggcaca | 960 |
| gagcttggtg ttccaaaggc cacgagggggt tttagaccct ggaccccgga catcctccaa | 1020 |

```
ggatctttta tattacgaca aacaagccag tcctgcctca gctcttctac caacaggtac   1080
ctttggccaa atgtctgaaa tagggttaca gattctataa ctgatggatc tcctaacagg   1140
ataattgagt gtcttatagg gaagttgaca ttttttggt tactctactc caaggcattg    1200
aattgtttac agtttttatt tgttcatggt ggaaactgtg gctgtatatt atttcttatt   1260
ggtgtaggct agtatgataa actttgctta tcttttagtt tgttatcaac ccatagtagc   1320
acatcaaact gaatctacaa aaaaactat ggaaaccct tatgtatgtg tttcatgagc     1380
aaaattacct ttgcttcaaa ttccaacctt ggaaatgttt cttgagtttc tacaggtagt   1440
ctaataccag attctatgta ccttgttgta acctcgtgcc gaattcggca cgagctcgtg   1500
ccgtgctgag tcattatttc ctctcataga tatagtgctt tctgaaggag gaatatccta   1560
ccaaaattta actgacattg cagtaataat aggccctgga agctttactg ggttaagagt   1620
atctctggca acagcacaag gttttgagct tgcttctagt gttgctgttc atgggatcag   1680
tcttcttgaa ctacaagcat attcaatttt gtgtgcttct gaacaaactg aagaagatat   1740
agttgctgtg atagaatcta caaaagccga ttttgtctat tatcaaatgt tcaataactc   1800
cctcattccc ctaacaggtg tgcatttagt gcctctaaat gaagtgcctc aaggcaaaat   1860
attgaagggc tcccctgcta tagctttgga taccaagtct attgggttgt accttattta   1920
taaactatca aatcgacttc cgaaaactac acttgccccc atttattcgc gcttttacca   1980
ctagagtgtc catgataatt taactgataa catcaatcgg gctagatatg tgtctagctt   2040
ttgtgcgtaa gctcttatgg aaataagtgt gatattttgc gagcacatgg tgatggagag   2100
ctcatctaag gcagcctcag taacatgccc cgcgtctatg aattgtgatt gtaatgcgta   2160
ttaaggattc cacaatttcc tgtgacaacc actaaaagta gtctacaagc tataaactct   2220
taaatctata gattgctagg gctgataaag aacctttagc attagaagcg tagagagaca   2280
ctgatgggtt agaatttgat acaaaaacat gaccttatta ctacaatagt ttacttgtga   2340
gcagtgcaca ccaagaatat aacattaagc ttctgagagg atacactcac tgagactctg   2400
tgagatctga cgtacccta cccaatctac tacactctac ctctggcaac gcattctaca    2460
gagcacgttt tagcgtgaaa atcttcacac gaagataccg ttgtattgtg gctccagtta   2520
gcgtcactaa gtattgagct agcagttcca ccttgattaa aaggtactgc atcttataca   2580
gactttagca gtcccattac atactcacct tgatctagaa acaatgatc tagccgcacc    2640 taacatttct atcttcaaaa aaccacttat agcgttttc tctccaactt ctaaaacata    2700
ctctatatac tttaaaggtt ttattgagga aatcagaaaa gattttcaa gtaacactga    2760 gctttctttt aaacatctgg tgcagagata tgtactacac aaactgaaat ataaacgttt   2820
tggaaaatat ctataaatat gaaacattaa gttttaagca taatatgctt taaaactagc   2880
agaatatatt gcaacacata ttctatacat tcttgcttgc attagaataa aaatagattg   2940
ctcaaggaaa ctgctaggta tacatatacc ttttcaccaa attagcagtg tataccttct   3000
ggaatactca taagcgtctt gtgaatacga tgttttcta cactgcaggt aagatgacgt     3060
ttggcctatt tttcgtatca gcagggctca ggtaaatgat gtatgtgcgg tgttattatc   3120
tatcaacaaa tgcgtatggt gtattttga tgccgaaaat tgtctccatc tcacaggcag    3180
catatcttac tcttgtaagc atataaaatt ttagttcaca gtgttaagaa acactgttat   3240
ttgatccctt gaaggtatgc ttaaacggtt tgaaaatgca cgtcctgcag tgtgtttgta   3300
atacctgttc taacaaccaa gagctttaag catctcgaaa aagcttttaa gaaattgatg   3360
cgtcccctag tagtgccgcg gtaagcatta ttatgaacgc tcaaaggtat agtattttgg   3420
```

```
catattgaat attacagtac agcatcaata tacagtttaa aactcaagta tcacatctcc    3480
tactgctatc atctatgctg aaaaactca tttataccct gtgatgcgct tttaagagtg    3540
ttacactgtt aattctttcc tctgtttaaa tgttatgcag aacatgagta ataaaactaa    3600
tagaagatat gtgagaagag gcattcagcc cattacttac tcatggatta gataagaaac    3660
tagagccacg tttgcttctg tttttcgtga catgcttatg tagaattctg cacaagcagc    3720
agaatggtgc tttcattaac acggatgtat atgggatggg taagggctct taagctttgc    3780
atggcaaggt tctatagctt tttagaactt catatatcgt accgaaacaa attaatacgg    3840
gtctatccat acattacgta atggctacta tgcaaaattc agaatattgc ccataaacaa    3900
ctagaaaaag tcttgcagat tttttctgat tactatattc cttcgggaat ctgaccagct    3960
atgggcgttc tgttatgcga tcaaggaaga tttatgtttg ggtggtcatg gcaacggttt    4020
taggtgccat ggcttttgtc acttttggaa gcatgatacc aatgggtaag ttgtctaatt    4080
ctggcaacgg acagtgcgtt gcaatgttgg gtaataaatg tctaccattg cgggattacc    4140
gtataatgta ccgcaacgag ttggcagaac tagagaagat gttacaacac aaattgtctg    4200
atgctcaaat taatcagttt ggtattaagg aagttgtcct caagaacatg atagccgaca    4260
tggtcgttga aaagtttgct catgacttag gcatacgtgt tggctcaaat agcttacgga    4320
gtctgatcaa aaatataaga atatttcagg atgctaatgg tgtcttcgac caggagagat    4380
atgaagccgt attggctgac agcggaatga ctgagtcgtc ctatgtgaat aaaattcgca    4440
atgctttacc ttctactatt ctaatggagt gtttattccc taatagggcg gaattacata    4500
ttccttatta tgatgcatta gcaaaagatg ttgtgttggg attgctgcag catcgtgtgg    4560
cagacatagt ggaaatatct tctgatgccg tagacatttc aggaagtgat atatctgatg    4620
atgaattgca aaaattgttt gaggagcagt acaagaattc tctaaatttc cctgaatatc    4680
gcagtgctga ttatataatc atggcagaag acgacttgct tgctgatgtc attgtttcgg    4740
atcaagaggt agacgttgag attaaaaaca gtgaactaca tgatcaaaga gatgttctaa    4800
atttagtatt tacagacaaa aatgaagctg agctagctta caaagcttac caagagggta    4860
agtcttttga ggaattggtt agtgatgctg gctacaccat agaggatatt gcactcaata    4920
atatctctaa ggatgttctt ccggtaggtg tgcgaaatgt ggtgtttgca ctaaatgaag    4980
gagaagtcag tgaaatgttc cgtagcgttg tcggctggca tatcatgaag gtaataagga    5040
agcatgagat cactaaggaa gacctagaaa agctgaaaga gaagatatct tcaaatatta    5100
gaaggcaaaa ggcaggtgag ttgctagtta gcaatgtgaa aaaagcaaac gatatgatca    5160
gccgcggggc attgctgaat gaactaaagg atatgtttgg tgcgcggatc agtggtgttt    5220
tgacgaattt tgatatgcat gggctcgata atctggcaa cttagtgaaa gactttccgt    5280
tgcagcttgg tataaacgcc tttactactt ggcgttttc atctgccgta ggaaaaccgt    5340
ctcatctggt tagcaatggt gacgcttatt tcggcgttct tgttactgaa gtagtgcctc    5400
caagaccaag gacacttgaa gaaagcaggt ctattcttac tgaagaatgg aagagtgcat    5460
tacgtatgaa gaaaatacgt gaatttgctg tggagttgcg ctcgaagcta caaaatggca    5520
c                                                                   5521
```

<210> SEQ ID NO 49
<211> LENGTH: 1938
<212> TYPE: DNA
<213> ORGANISM: Ehrlichia sp.

<400> SEQUENCE: 49

```
ttgaggagta ttaagcaagt ctccgaaaga tgagtttgac aaatgctttc gagactcttt      60
aagcatcttt aaaaagcatt tttctgtaac cttatcagaa tataaagcct catgtaacgc     120
tgtatctccc atatgagaaa ggagtgcttg acagctatct gggcatttt tcgcaattta      180
cttatatagc ttaccgtcac cattagcagc tgctatatgt aaagccgtct taccataagc     240
atctctctgc gttgctggag cccctttatc aagagcaac ctagcagtct tctggttgcc      300
agcagctgtt gctaaatgca aggctggagt tccagtgtga tccgtagacg aaagatctgc     360
accctctgt aaaggaaat ttacaatcct attagcctct ttaaggttac ttgcctcatt       420
tgccacttga actgcagcag ctaaagggct catagatccg gtaggagtat ttatatgtgc     480
cccagcttct acaacacgct ttaaatgctt tatagcttta ccccctgaa agcaccctcc      540
ttgtataccc acagaaatag ctggttctgg agacgcattt acatcagcac tgttttaat     600
taacgtcttc actgcagcat attgaccact agttagtgct tcagcggtca agttgtctt     660
ttttccttca ggagttgtaa tttcttcatt tacactaatc acttcagtgg taataagatg    720
cctcaataca tctgctgcac cttttcttac tgcctcgaca gcaacatgct gcgggtaagg    780
ctcatatctc attaacatgt caagtgctgg tagcgatact tttccaccac ttgcttcacg    840
aatcgcatat acacctggag taggaacacc atcctttaca ggaaacttag aataactact    900
cttccttcca agagcctgct gcaatatctc taaatttcca tcctttgctg cgtaatgtat    960
tatagttcca ccatcatgtg accgagcatc tacgtccatg ctattacagc gtaacatagt   1020
cttaacaccc tcagtgttgc cccctttata cgcagctacc acaggcgttt cacctgtcac   1080
tggagatggt acattgattg atggaatatt acgcacattc tcaatcaaca tctgcaattt   1140
aacgcttacg cctttatggc ttggctcatc ctcaactatc atgtgaatag gcgctttgcc   1200
attcggtgct aattgattta caacagactc aggagtgcat cttaccacct gctcaaaaac   1260
ccccactgtt gattttgtg ctgcagcatg tataggtgca ttacctgcaa tatctaaatt    1320
agtaaaaggt tcctctccat acctatgata tgcttcctcc aatacccttt tcgcaagagg    1380
atcaaaattt ggggtcccat tagaagatac aaaatgcacc agcgttgatg cgtcctctgg   1440
attaggacat gtaaagagag attttacttc tgaagaagct gagccataca ctttatctgc   1500
aatgttcatg gccttctcga agatcttctc agcctccggt atagccttct aatagcatac   1560
tgtactgcac tcatcccttt tttatccggg aatattagtg cctctgcaca ctgcgattgc   1620
cctcaatatt tgacgacacc gcttcttgca tcttgtcaat gtatgataaa acatcccgcc   1680
ttggccattg ctttgcaaca atgtggcaaa cggtttcacc agcatcattt gcaacgctaa   1740
tatcacttaa ccttgagaga agatgcttta cttctggtg atccatacgc tccgtagcaa    1800
tatgaagcgg agtgtttcca cccggtccct tagcattaac atctgctata agagctttgt   1860
cgcatagtac atcaagattg cctaaagcat ttttgcctac tgaagatgca gctgtatgta   1920
atggcgtatt accatcta                                                 1938
```

<210> SEQ ID NO 50
<211> LENGTH: 578
<212> TYPE: PRT
<213> ORGANISM: Ehrlichia sp.

<400> SEQUENCE: 50

```
Met Tyr Gly Ile Asp Ile Glu Leu Ser Asp Tyr Arg Ile Gly Ser Glu
  1               5                  10                  15
```

-continued

```
Thr Ile Ser Ser Gly Asp Asp Gly Tyr Tyr Glu Gly Cys Ala Cys Asp
             20                  25                  30

Lys Asp Ala Ser Thr Asn Ala Tyr Ser Tyr Asp Lys Cys Arg Val Val
             35                  40                  45

Arg Gly Thr Trp Arg Pro Ser Glu Leu Val Leu Tyr Val Gly Asp Glu
 50                  55                  60

His Val Ala Cys Arg Asp Val Ala Ser Gly Met His His Gly Asn Leu
 65                  70                  75                  80

Pro Gly Lys Val Tyr Phe Ile Glu Ala Glu Ala Gly Arg Ala Ala Thr
                 85                  90                  95

Ala Glu Gly Gly Val Tyr Thr Thr Val Val Glu Ala Leu Ser Leu Val
                100                 105                 110

Gln Glu Glu Glu Gly Thr Gly Met Tyr Leu Ile Asn Ala Pro Glu Lys
            115                 120                 125

Ala Val Val Arg Phe Phe Lys Ile Glu Lys Ser Ala Ala Glu Glu Pro
            130                 135                 140

Gln Thr Val Asp Pro Ser Val Val Glu Ser Ala Thr Gly Ser Gly Val
145                 150                 155                 160

Asp Thr Gln Glu Glu Gln Glu Ile Asp Gln Glu Ala Pro Ala Ile Glu
                165                 170                 175

Glu Val Glu Thr Glu Glu Gln Glu Val Ile Leu Glu Glu Gly Thr Leu
            180                 185                 190

Ile Asp Leu Glu Gln Pro Val Ala Gln Val Pro Val Val Ala Glu Ala
            195                 200                 205

Glu Leu Pro Gly Val Glu Ala Ala Glu Ala Ile Val Pro Ser Leu Glu
            210                 215                 220

Glu Asn Lys Leu Gln Glu Val Val Val Ala Pro Glu Ala Gln Gln Leu
225                 230                 235                 240

Glu Ser Ala Pro Glu Val Ser Ala Pro Ala Gln Pro Glu Ser Thr Val
                245                 250                 255

Leu Gly Val Ala Glu Gly Asp Leu Lys Ser Glu Val Ser Val Glu Ala
            260                 265                 270

Asn Ala Asp Val Ala Gln Lys Glu Val Ile Ser Gly Gln Gln Glu Gln
275                 280                 285

Glu Ile Ala Glu Ala Leu Glu Gly Thr Glu Ala Pro Val Glu Val Lys
            290                 295                 300

Glu Glu Thr Glu Val Leu Leu Lys Glu Asp Thr Leu Ile Asp Leu Glu
305                 310                 315                 320

Gln Pro Val Ala Gln Val Pro Val Val Ala Glu Ala Glu Leu Pro Gly
                325                 330                 335

Val Glu Ala Ala Glu Ala Ile Val Pro Ser Leu Glu Glu Asn Lys Leu
            340                 345                 350

Gln Glu Val Val Val Ala Pro Glu Ala Gln Gln Leu Glu Ser Ala Pro
            355                 360                 365

Glu Val Ser Ala Pro Ala Gln Pro Glu Ser Thr Val Leu Gly Val Thr
            370                 375                 380

Glu Gly Asp Leu Lys Ser Glu Val Ser Val Glu Ala Asp Ala Gly Met
385                 390                 395                 400

Gln Gln Glu Ala Gly Ile Ser Asp Gln Glu Thr Gln Ala Thr Glu Glu
                405                 410                 415

Val Glu Lys Val Glu Val Ser Val Glu Thr Lys Thr Glu Glu Pro Glu
            420                 425                 430

Val Ile Leu Glu Glu Gly Thr Leu Ile Asp Leu Glu Gln Pro Val Ala
```

```
                 435                 440                 445
Gln Val Pro Val Val Ala Glu Ala Glu Leu Pro Gly Val Glu Ala Ala
            450                 455                 460
Glu Ala Ile Val Pro Ser Leu Glu Glu Asn Lys Leu Gln Glu Val Val
465                 470                 475                 480
Val Ala Pro Glu Ala Gln Gln Leu Glu Ser Ala Pro Glu Val Ser Ala
            485                 490                 495
Pro Val Gln Pro Glu Ser Thr Val Leu Gly Val Thr Glu Gly Asp Leu
            500                 505                 510
Lys Ser Glu Val Ser Val Glu Ala Asp Ala Gly Met Gln Gln Glu Ala
            515                 520                 525
Gly Ile Ser Asp Gln Glu Thr Gln Ala Thr Glu Val Glu Lys Val
            530                 535                 540
Glu Val Ser Val Glu Ala Asp Ala Gly Met Gln Gln Glu Leu Val Asp
545                 550                 555                 560
Val Pro Thr Ala Leu Pro Leu Lys Asp Pro Asp Asp Glu Asp Val Leu
            565                 570                 575
Ser Tyr
```

```
<210> SEQ ID NO 51
<211> LENGTH: 125
<212> TYPE: PRT
<213> ORGANISM: Ehrlichia sp.
<220> FEATURE:
<221> NAME/KEY: VARIANT
<222> LOCATION: (1)...(1)
<223> OTHER INFORMATION: Xaa = Threonine or Lysine
<220> FEATURE:
<221> NAME/KEY: VARIANT
<222> LOCATION: (4)...(4)
<223> OTHER INFORMATION: Xaa = Glutamine, Threonine or Proline
<220> FEATURE:
<221> NAME/KEY: VARIANT
<222> LOCATION: (7)...(7)
<223> OTHER INFORMATION: Xaa = Isoleucine or Leucine
<220> FEATURE:
<221> NAME/KEY: VARIANT
<222> LOCATION: (9)...(9)
<223> OTHER INFORMATION: Xaa = Glutamic Acid or Lysine
<220> FEATURE:
<221> NAME/KEY: VARIANT
<222> LOCATION: (11)...(11)
<223> OTHER INFORMATION: Xaa = Glycine or Aspartic Acid
<220> FEATURE:
<221> NAME/KEY: VARIANT
<222> LOCATION: (71)...(71)
<223> OTHER INFORMATION: Xaa = Alanine or Valine
<220> FEATURE:
<221> NAME/KEY: VARIANT
<222> LOCATION: (81)...(81)
<223> OTHER INFORMATION: Xaa = Alanine or Threonine
<220> FEATURE:
<221> NAME/KEY: VARIANT
<222> LOCATION: (94)...(94)
<223> OTHER INFORMATION: Xaa = Asparigine or Aspartic Acid
<220> FEATURE:
<221> NAME/KEY: VARIANT
<222> LOCATION: (96)...(96)
<223> OTHER INFORMATION: Xaa = Aspartic Acid or Glycine
<220> FEATURE:
<221> NAME/KEY: VARIANT
<222> LOCATION: (97)...(97)
<223> OTHER INFORMATION: Xaa = Valine or Methionine
<220> FEATURE:
<221> NAME/KEY: VARIANT
<222> LOCATION: (98)...(98)
<223> OTHER INFORMATION: Xaa = Alanine or Glutamine
<220> FEATURE:
<221> NAME/KEY: VARIANT
```

```
<222> LOCATION: (100)...(100)
<223> OTHER INFORMATION: Xaa = Lysine or Glutamine
<220> FEATURE:
<221> NAME/KEY: VARIANT
<222> LOCATION: (101)...(101)
<223> OTHER INFORMATION: Xaa = Glutamic Acid or Alanine
<220> FEATURE:
<221> NAME/KEY: VARIANT
<222> LOCATION: (102)...(102)
<223> OTHER INFORMATION: Xaa = Valine or Glycine
<220> FEATURE:
<221> NAME/KEY: VARIANT
<222> LOCATION: (105)...(105)
<223> OTHER INFORMATION: Xaa = Glycine or Aspartic Acid
<220> FEATURE:
<221> NAME/KEY: VARIANT
<222> LOCATION: (107)...(107)
<223> OTHER INFORMATION: Xaa = Glutamine or Glutamic Acid
<220> FEATURE:
<221> NAME/KEY: VARIANT
<222> LOCATION: (108)...(108)
<223> OTHER INFORMATION: Xaa = Glutamic Acid or Threonine
<220> FEATURE:
<221> NAME/KEY: VARIANT
<222> LOCATION: (110)...(110)
<223> OTHER INFORMATION: Xaa = Glutamic Acid or Alanine
<220> FEATURE:
<221> NAME/KEY: VARIANT
<222> LOCATION: (112)...(112)
<223> OTHER INFORMATION: Xaa = Alanine or Threonine
<220> FEATURE:
<221> NAME/KEY: VARIANT
<222> LOCATION: (114)...(114)
<223> OTHER INFORMATION: Xaa = Alanine or Glutamic Acid
<220> FEATURE:
<221> NAME/KEY: VARIANT
<222> LOCATION: (115)...(115)
<223> OTHER INFORMATION: Xaa = Leucine or Valine
<220> FEATURE:
<221> NAME/KEY: VARIANT
<222> LOCATION: (117)...(117)
<223> OTHER INFORMATION: Xaa = Glycine or Lysine
<220> FEATURE:
<221> NAME/KEY: VARIANT
<222> LOCATION: (118)...(118)
<223> OTHER INFORMATION: Xaa = Threonine or Valine
<220> FEATURE:
<221> NAME/KEY: VARIANT
<222> LOCATION: (120)...(120)
<223> OTHER INFORMATION: Xaa = Alanine or Valine
<220> FEATURE:
<221> NAME/KEY: VARIANT
<222> LOCATION: (121)...(121)
<223> OTHER INFORMATION: Xaa = Proline or Serine
<220> FEATURE:
<221> NAME/KEY: VARIANT
<222> LOCATION: (124)...(124)
<223> OTHER INFORMATION: Xaa = Valine, Threonine or Alanine

<400> SEQUENCE: 51

Xaa Glu Glu Xaa Glu Val Xaa Leu Xaa Glu Xaa Thr Leu Ile Asp Leu
 1               5                  10                  15

Glu Gln Pro Val Ala Gln Val Pro Val Val Ala Glu Ala Glu Leu Pro
            20                  25                  30

Gly Val Glu Ala Ala Glu Ala Ile Val Pro Ser Leu Glu Glu Asn Lys
         35                  40                  45

Leu Gln Glu Val Val Ala Pro Glu Ala Gln Gln Leu Glu Ser Ala
     50                  55                  60

Pro Glu Val Ser Ala Pro Xaa Gln Pro Glu Ser Thr Val Leu Gly Val
65                  70                  75                  80

Xaa Glu Gly Asp Leu Lys Ser Gly Val Ser Val Glu Ala Xaa Ala Xaa
             85                  90                  95
```

-continued

```
Xaa Xaa Gln Xaa Xaa Xaa Ile Ser Xaa Xaa Gln Glu Xaa Xaa Xaa Xaa
            100                 105                 110

Glu Xaa Xaa Glu Xaa Xaa Glu Xaa Xaa Val Glu Xaa Xaa
        115                 120                 125

<210> SEQ ID NO 52
<211> LENGTH: 253
<212> TYPE: PRT
<213> ORGANISM: Ehrlichia sp.

<400> SEQUENCE: 52

Ala Val Lys Ile Thr Asn Ser Thr Ile Asp Gly Lys Val Cys Asn Gly
 1               5                  10                  15

Ser Arg Glu Lys Gly Asn Ser Ala Gly Asn Asn Asn Ser Ala Val Ala
            20                  25                  30

Thr Tyr Ala Gln Thr His Thr Ala Asn Thr Ser Thr Ser Gln Cys Ser
        35                  40                  45

Gly Leu Gly Thr Thr Val Val Lys Gln Gly Tyr Gly Ser Leu Asn Lys
    50                  55                  60

Phe Val Ser Leu Thr Gly Val Gly Glu Gly Lys Asn Trp Pro Thr Gly
65                  70                  75                  80

Lys Ile His Asp Gly Ser Ser Gly Val Lys Asp Gly Glu Gln Asn Gly
                85                  90                  95

Asn Ala Lys Ala Val Ala Lys Asp Leu Val Asp Leu Asn Arg Asp Glu
            100                 105                 110

Lys Thr Ile Val Ala Gly Leu Leu Ala Lys Thr Ile Glu Gly Gly Glu
        115                 120                 125

Val Val Glu Ile Arg Ala Val Ser Ser Thr Ser Val Met Val Asn Ala
    130                 135                 140

Cys Tyr Asp Leu Leu Ser Glu Gly Leu Gly Val Val Pro Tyr Ala Cys
145                 150                 155                 160

Val Gly Leu Gly Gly Asn Phe Val Gly Val Val Asp Gly His Ile Thr
                165                 170                 175

Pro Lys Leu Ala Tyr Arg Leu Lys Ala Gly Leu Ser Tyr Gln Leu Ser
            180                 185                 190

Pro Glu Ile Ser Ala Phe Ala Gly Gly Phe Tyr His Arg Val Val Gly
        195                 200                 205

Asp Gly Val Tyr Asp Asp Leu Pro Ala Gln Arg Leu Val Asp Asp Thr
    210                 215                 220

Ser Pro Ala Gly Arg Thr Lys Asp Thr Ala Val Ala Asn Phe Ser Met
225                 230                 235                 240

Ala Tyr Val Gly Gly Glu Phe Gly Val Arg Phe Ala Phe
                245                 250

<210> SEQ ID NO 53
<211> LENGTH: 366
<212> TYPE: PRT
<213> ORGANISM: Ehrlichia sp.

<400> SEQUENCE: 53

Tyr Met Arg Ser Arg Ser Lys Leu Leu Leu Gly Ser Val Met Met Ser
 1               5                  10                  15

Met Ala Ile Val Met Ala Gly Asn Asp Val Arg Ala His Asp Asp Val
            20                  25                  30

Ser Ala Leu Glu Thr Gly Gly Ala Gly Tyr Phe Tyr Val Gly Leu Asp
        35                  40                  45
```

Tyr Ser Pro Ala Phe Ser Lys Ile Arg Asp Phe Ser Ile Arg Glu Ser
        50                  55                  60

Asn Gly Glu Thr Lys Ala Val Tyr Pro Tyr Leu Lys Asp Gly Lys Ser
 65                  70                  75                  80

Val Lys Leu Glu Ser His Lys Phe Asp Trp Asn Thr Pro Asp Pro Arg
                 85                  90                  95

Ile Gly Phe Lys Asp Asn Met Leu Val Ala Met Glu Gly Ser Val Gly
                100                 105                 110

Tyr Gly Ile Gly Gly Ala Arg Val Glu Leu Glu Ile Gly Tyr Glu Arg
            115                 120                 125

Phe Lys Thr Lys Gly Ile Arg Asp Ser Gly Ser Lys Glu Asp Glu Ala
        130                 135                 140

Asp Thr Val Tyr Leu Leu Ala Lys Glu Leu Ala Tyr Asp Val Val Thr
145                 150                 155                 160

Gly Gln Thr Asp Asn Leu Ala Ala Ala Leu Ala Lys Thr Ser Gly Lys
                165                 170                 175

Asp Ile Val Gln Phe Ala Asn Ala Val Lys Ile Thr Asn Ser Ala Ile
            180                 185                 190

Asp Gly Lys Ile Cys Asn Arg Gly Lys Ala Ser Gly Gly Ser Lys Gly
        195                 200                 205

Leu Ser Ser Lys Ala Gly Ser Cys Asp Ser Ile Asp Lys Gln Ser
        210                 215                 220

Gly Ser Leu Glu Gln Ser Leu Thr Ala Ala Leu Gly Asp Lys Gly Ala
225                 230                 235                 240

Glu Lys Trp Pro Lys Ile Asn Asn Gly Thr Ser Asp Thr Thr Leu Asn
                245                 250                 255

Gly Asn Asp Thr Ser Ser Thr Pro Tyr Thr Lys Asp Ala Ser Ala Thr
                260                 265                 270

Val Ala Lys Asp Leu Val Ala Leu Asn His Asp Glu Lys Thr Ile Val
            275                 280                 285

Ala Gly Leu Leu Ala Lys Thr Ile Glu Gly Gly Glu Val Val Glu Ile
        290                 295                 300

Arg Ala Val Ser Ser Thr Ser Val Met Val Asn Ala Cys Tyr Asp Leu
305                 310                 315                 320

Leu Ser Glu Gly Leu Gly Val Val Pro Tyr Ala Cys Val Gly Leu Gly
                325                 330                 335

Gly Asn Phe Val Gly Val Val Asp Gly His Ile Thr Pro Lys Leu Ala
                340                 345                 350

Tyr Arg Leu Lys Ala Gly Leu Ser Tyr Gln Leu Ser Pro Glu
            355                 360                 365

<210> SEQ ID NO 54
<211> LENGTH: 340
<212> TYPE: PRT
<213> ORGANISM: Ehrlichia sp.

<400> SEQUENCE: 54

Arg Ser Asp Tyr Gln Gly Gln Val Leu Ala Ile Ile Arg Pro Gln Gly
 1               5                  10                  15

Glu Ala Thr Ala Glu Gly Val Asn Lys Glu Pro Glu Ser Lys Glu Glu
                20                  25                  30

Val Leu Ala Gln Pro Val Ala Gln Ala Val Ser Thr Gln Lys Pro
            35                  40                  45

Gln Glu Lys Thr Ile Ile Glu Gly Lys Gly Leu Val Thr Pro Thr Val
 50                  55                  60

-continued

Glu Asp Phe Val Ala Gly Ile Asn Thr Thr Pro Thr Ser Arg Ala Leu
65                  70                  75                  80

Gly Met Ser Ala Lys Ser Glu Gln Asp Lys Lys Ile Val Ala Ser Gln
                85                  90                  95

Pro Ser Lys Asp Leu Met Ser Cys His Gly Asp Val Val Gly Glu Arg
            100                 105                 110

Arg Val Lys Met Ser Lys Ile Arg Gln Val Ile Ala Ala Arg Leu Lys
        115                 120                 125

Glu Ser Gln Asn Thr Ser Ala Thr Leu Ser Thr Phe Asn Glu Val Asp
    130                 135                 140

Met Ser Lys Val Met Glu Leu Arg Ala Lys Tyr Lys Asp Ala Phe Val
145                 150                 155                 160

Lys Arg Tyr Asp Val Lys Leu Gly Phe Met Ser Phe Ile Arg Ala
                165                 170                 175

Val Val Leu Val Leu Ser Glu Ile Pro Val Leu Asn Ala Glu Ile Ser
                180                 185                 190

Gly Asp Asp Ile Val Tyr Arg Asp Tyr Cys Asn Ile Gly Val Ala Val
                195                 200                 205

Gly Thr Asp Lys Gly Leu Val Val Pro Val Ile Arg Arg Ala Glu Thr
    210                 215                 220

Met Ser Leu Ala Glu Met Glu Gln Ala Leu Val Asp Leu Ser Thr Lys
225                 230                 235                 240

Ala Arg Ser Gly Lys Leu Ser Val Ser Asp Met Ser Gly Ala Thr Phe
                245                 250                 255

Thr Ile Thr Asn Gly Val Tyr Gly Ser Leu Leu Ser Thr Pro Ile
                260                 265                 270

Ile Asn Pro Pro Gln Ser Gly Ile Leu Gly Met His Ala Ile Gln Gln
            275                 280                 285

Arg Pro Val Ala Val Asp Gly Lys Val Glu Ile Arg Pro Met Met Tyr
    290                 295                 300

Leu Ala Leu Ser Tyr Asp His Arg Ile Val Asp Gly Gln Gly Ala Val
305                 310                 315                 320

Thr Phe Leu Val Arg Val Lys Gln Tyr Ile Glu Asp Pro Asn Arg Leu
                325                 330                 335

Ala Leu Gly Ile
            340

<210> SEQ ID NO 55
<211> LENGTH: 177
<212> TYPE: PRT
<213> ORGANISM: Ehrlichia sp.

<400> SEQUENCE: 55

Gly Val Phe Met Gly Arg Gly Thr Ile Thr Ile His Ser Lys Glu Asp
1               5                   10                  15

Phe Ala Cys Met Arg Arg Ala Gly Met Leu Ala Ala Lys Val Leu Asp
                20                  25                  30

Phe Ile Thr Pro His Val Val Pro Gly Val Thr Thr Asn Ala Leu Asn
            35                  40                  45

Asp Leu Cys His Asp Phe Ile Ile Ser Ala Gly Ala Ile Pro Ala Pro
        50                  55                  60

Leu Gly Tyr Arg Gly Tyr Pro Lys Ser Ile Cys Thr Ser Lys Asn Phe
65                  70                  75                  80

Val Val Cys His Gly Ile Pro Asp Asp Ile Ala Leu Lys Asn Gly Asp

```
                       85                  90                  95
Ile Val Asn Ile Asp Val Thr Val Ile Leu Asp Gly Trp His Gly Asp
                100                 105                 110
Thr Asn Arg Met Tyr Trp Val Gly Asp Asn Val Ser Ile Lys Ala Lys
            115                 120                 125
Arg Ile Cys Glu Ala Ser Tyr Lys Ala Leu Met Ala Ala Ile Gly Val
        130                 135                 140
Ile Gln Pro Gly Lys Lys Leu Asn Ser Ile Gly Leu Ala Ile Glu Glu
145                 150                 155                 160
Glu Ile Arg Gly Tyr Gly Tyr Ser Ile Val Arg Asp Tyr Cys Gly His
                165                 170                 175
Gly

<210> SEQ ID NO 56
<211> LENGTH: 197
<212> TYPE: PRT
<213> ORGANISM: Ehrlichia sp.

<400> SEQUENCE: 56

Glu Trp Trp Cys Thr Pro Leu Trp Cys Ala Lys Asn Thr Ile Met Leu
1               5                   10                  15
Cys Arg Leu Lys Asn Thr Gly Gly Cys Glu Val Met Arg Glu Val Leu
            20                  25                  30
Val Pro Tyr Ala Gly Val Ser Pro Ser Val Asp Ser Thr Ala Phe Ile
        35                  40                  45
Ala Gly Tyr Ala Arg Ile Ile Gly Asp Val Cys Ile Gly Lys Asn Ala
    50                  55                  60
Ser Ile Trp Tyr Gly Thr Val Leu Arg Gly Asp Val Asp Lys Ile Glu
65                  70                  75                  80
Val Gly Glu Gly Thr Asn Ile Gln Asp Asn Thr Val Val His Thr Asp
                85                  90                  95
Ser Met His Gly Asp Thr Val Ile Gly Lys Phe Val Thr Ile Gly His
                100                 105                 110
Ser Cys Ile Leu His Ala Cys Thr Leu Gly Asn Asn Ala Phe Val Gly
            115                 120                 125
Met Gly Ser Ile Val Met Asp Arg Ala Val Met Glu Glu Gly Ser Met
        130                 135                 140
Leu Ala Ala Gly Ser Leu Leu Thr Arg Gly Lys Ile Val Lys Ser Gly
145                 150                 155                 160
Glu Leu Trp Ala Gly Arg Pro Ala Lys Phe Leu Arg Met Met Thr Glu
                165                 170                 175
Glu Glu Ile Leu Tyr Leu Gln Lys Ser Ala Glu Asn Tyr Ile Ala Leu
                180                 185                 190
Ser Arg Gly Tyr Leu
        195

<210> SEQ ID NO 57
<211> LENGTH: 172
<212> TYPE: PRT
<213> ORGANISM: Ehrlichia sp.

<400> SEQUENCE: 57

Ala Asn Leu Ala Arg Ala Thr Ala Pro Ser Met Phe Ser Phe Ser Leu
1               5                   10                  15
Lys Gly Arg Pro Ser Phe Phe Glu Ile Ala Phe Ser Leu Gly Ser Val
            20                  25                  30
```

-continued

```
Met Met Ser Met Ala Ile Val Met Ala Gly Asn Asp Val Arg Ala His
        35                  40                  45

Asp Asp Val Ser Ala Leu Glu Thr Gly Ala Gly Tyr Phe Tyr Val
    50                  55                  60

Gly Leu Asp Tyr Ser Pro Ala Phe Ser Lys Ile Arg Asp Phe Ser Ile
65                  70                  75                  80

Arg Glu Ser Asn Gly Glu Thr Lys Ala Val Tyr Pro Tyr Leu Lys Asp
                85                  90                  95

Gly Lys Ser Val Lys Leu Glu Ser Asn Lys Phe Asp Trp Asn Thr Pro
            100                 105                 110

Asp Pro Arg Ile Gly Phe Lys Asp Asn Met Leu Val Ala Met Glu Gly
            115                 120                 125

Ser Val Gly Tyr Gly Ile Gly Gly Ala Arg Val Glu Leu Glu Ile Gly
            130                 135                 140

Tyr Glu Arg Phe Lys Thr Lys Gly Ile Arg Asp Ser Gly Ser Lys Glu
145                 150                 155                 160

Asp Glu Ala Asp Thr Val Tyr Leu Leu Ala Lys Glu
                165                 170
```

<210> SEQ ID NO 58
<211> LENGTH: 196
<212> TYPE: PRT
<213> ORGANISM: Ehrlichia sp.

<400> SEQUENCE: 58

```
Lys Leu Lys Glu Asp Val Ala Ser Met Ser Asp Glu Ala Leu Leu Lys
1               5                   10                  15

Phe Ala Asn Arg Leu Arg Arg Gly Val Pro Met Ala Ala Pro Val Phe
                20                  25                  30

Glu Gly Pro Lys Asp Ala Gln Ile Ser Arg Leu Leu Glu Leu Ala Asp
            35                  40                  45

Val Asp Pro Ser Gly Gln Val Asp Leu Tyr Asp Gly Arg Ser Gly Gln
    50                  55                  60

Lys Phe Asp Arg Lys Val Thr Val Gly Tyr Ile Tyr Met Leu Lys Leu
65                  70                  75                  80

His His Leu Val Asp Asp Lys Ile His Ala Arg Ser Val Gly Pro Tyr
                85                  90                  95

Gly Leu Val Thr Gln Gln Pro Leu Gly Gly Lys Ser His Phe Gly Gly
            100                 105                 110

Gln Arg Phe Gly Glu Met Glu Cys Trp Ala Leu Gln Ala Tyr Gly Ala
            115                 120                 125

Ala Tyr Thr Leu Gln Glu Met Leu Thr Val Lys Ser Asp Asp Ile Val
    130                 135                 140

Gly Arg Val Thr Ile Tyr Glu Ser Ile Ile Lys Gly Asp Ser Asn Phe
145                 150                 155                 160

Glu Cys Gly Ile Pro Glu Ser Phe Asn Val Met Val Lys Glu Leu Arg
                165                 170                 175

Ser Leu Cys Leu Asp Val Val Leu Lys Gln Asp Lys Glu Phe Thr Ser
            180                 185                 190

Ser Lys Val Glu
        195
```

<210> SEQ ID NO 59
<211> LENGTH: 719
<212> TYPE: PRT

-continued

<213> ORGANISM: Ehrlichia sp.

<400> SEQUENCE: 59

| Gly | Phe | Thr | Ile | Met | Lys | Thr | Leu | Asp | Leu | Tyr | Gly | Tyr | Thr | Ser | Ile |
|---|---|---|---|---|---|---|---|---|---|---|---|---|---|---|---|
| 1 | | | | 5 | | | | | 10 | | | | | 15 | |

| Ala | Gln | Ser | Phe | Asp | Asn | Ile | Cys | Ile | Ser | Ile | Ser | Ser | Pro | Gln | Ser |
| | | | 20 | | | | 25 | | | | | 30 | | | |

| Ile | Arg | Ala | Met | Ser | Tyr | Gly | Glu | Ile | Lys | Asp | Ile | Ser | Thr | Thr | Ile |
| | | 35 | | | | 40 | | | | | 45 | | | | |

| Tyr | Arg | Thr | Phe | Lys | Val | Glu | Lys | Gly | Gly | Leu | Phe | Cys | Pro | Lys | Ile |
| | 50 | | | | | 55 | | | | | 60 | | | | |

| Phe | Gly | Pro | Val | Asn | Asp | Asp | Glu | Cys | Leu | Cys | Gly | Lys | Tyr | Arg | Lys |
| 65 | | | | | 70 | | | | 75 | | | | | | 80 |

| Lys | Arg | Tyr | Arg | Gly | Ile | Val | Cys | Glu | Lys | Cys | Gly | Val | Glu | Val | Thr |
| | | | | 85 | | | | | 90 | | | | | 95 | |

| Ser | Ser | Lys | Val | Arg | Arg | Glu | Arg | Met | Gly | His | Ile | Glu | Leu | Val | Ser |
| | | | | 100 | | | | | 105 | | | | | 110 | |

| Pro | Val | Ala | His | Ile | Trp | Phe | Leu | Lys | Ser | Leu | Pro | Ser | Arg | Ile | Gly |
| | | | 115 | | | | | 120 | | | | | 125 | | |

| Ala | Leu | Leu | Asp | Met | Pro | Leu | Lys | Ala | Ile | Glu | Asn | Ile | Leu | Tyr | Ser |
| | 130 | | | | | 135 | | | | | 140 | | | | |

| Gly | Asp | Phe | Val | Val | Ile | Asp | Pro | Val | Ala | Thr | Pro | Phe | Ala | Lys | Gly |
| 145 | | | | | 150 | | | | | 155 | | | | | 160 |

| Glu | Val | Ile | Ser | Glu | Val | Val | Tyr | Asn | Gln | Ala | Arg | Asp | Ala | Tyr | Gly |
| | | | | 165 | | | | | 170 | | | | | 175 | |

| Glu | Asp | Gly | Phe | Phe | Ala | Leu | Thr | Gly | Val | Glu | Ala | Ile | Lys | Glu | Leu |
| | | | 180 | | | | | 185 | | | | | 190 | | |

| Leu | Thr | Arg | Leu | Asp | Leu | Glu | Ala | Ile | Arg | Ala | Thr | Leu | Arg | Asn | Glu |
| | | 195 | | | | | 200 | | | | | 205 | | | |

| Leu | Glu | Ser | Thr | Ser | Ser | Glu | Met | Lys | Arg | Lys | Lys | Val | Val | Lys | Arg |
| | 210 | | | | | 215 | | | | | 220 | | | | |

| Leu | Arg | Leu | Val | Glu | Asn | Phe | Ile | Lys | Ser | Gly | Asn | Arg | Pro | Glu | Trp |
| 225 | | | | | 230 | | | | | 235 | | | | | 240 |

| Met | Ile | Leu | Thr | Val | Ile | Pro | Val | Leu | Pro | Pro | Asp | Leu | Arg | Pro | Leu |
| | | | | 245 | | | | | 250 | | | | | 255 | |

| Val | Ser | Leu | Glu | Asn | Gly | Arg | Pro | Ala | Val | Ser | Asp | Leu | Asn | His | His |
| | | | | 260 | | | | | 265 | | | | | 270 | |

| Tyr | Arg | Thr | Ile | Ile | Asn | Arg | Asn | Asn | Arg | Leu | Glu | Lys | Leu | Leu | Lys |
| | | | 275 | | | | | 280 | | | | | 285 | | |

| Leu | Asn | Pro | Pro | Ala | Ile | Met | Ile | Arg | Asn | Glu | Lys | Arg | Met | Leu | Gln |
| | | 290 | | | | | 295 | | | | | 300 | | | |

| Glu | Ala | Val | Asp | Ala | Leu | Phe | Asp | Ser | Ser | Arg | Arg | Ser | Tyr | Val | Ser |
| 305 | | | | | 310 | | | | | 315 | | | | | 320 |

| Ser | Arg | Val | Gly | Ser | Met | Gly | Tyr | Lys | Lys | Ser | Leu | Ser | Asp | Met | Leu |
| | | | | 325 | | | | | 330 | | | | | 335 | |

| Lys | Gly | Lys | Gln | Gly | Arg | Phe | Arg | Gln | Asn | Leu | Leu | Gly | Lys | Arg | Val |
| | | | 340 | | | | | 345 | | | | | 350 | | |

| Asp | Tyr | Ser | Gly | Arg | Ser | Val | Ile | Val | Val | Gly | Pro | Ser | Leu | Lys | Leu |
| | | 355 | | | | | 360 | | | | | 365 | | | |

| His | Gln | Cys | Gly | Leu | Pro | Lys | Lys | Met | Ala | Leu | Glu | Leu | Phe | Lys | Pro |
| | 370 | | | | | 375 | | | | | 380 | | | | |

| Phe | Ile | Cys | Ser | Lys | Leu | Lys | Met | Tyr | Gly | Ile | Ala | Pro | Thr | Val | Lys |
| 385 | | | | | 390 | | | | | 395 | | | | | 400 |

```
Leu Ala Asn Lys Met Ile Gln Ser Glu Lys Pro Asp Val Trp Asp Val
                405                 410                 415

Leu Asp Glu Val Ile Lys Glu His Pro Ile Leu Leu Asn Arg Ala Pro
            420                 425                 430

Thr Leu His Arg Leu Gly Leu Gln Ala Phe Asp Pro Val Leu Ile Glu
        435                 440                 445

Gly Lys Ala Ile Gln Leu His Pro Leu Val Cys Ser Ala Phe Asn Ala
450                 455                 460

Asp Phe Asp Gly Asp Gln Met Ala Val His Val Pro Leu Ser Gln Glu
465                 470                 475                 480

Ala Gln Leu Glu Ala Arg Val Leu Met Met Ser Thr Asn Asn Ile Leu
                485                 490                 495

Ser Pro Ser Asn Gly Arg Pro Ile Ile Val Pro Ser Lys Asp Ile Val
            500                 505                 510

Leu Gly Ile Tyr Tyr Leu Thr Leu Leu Glu Glu Asp Pro Glu Val Arg
        515                 520                 525

Glu Val Gln Thr Phe Ala Glu Phe Ser His Val Glu Tyr Ala Leu His
530                 535                 540

Glu Gly Ile Val His Thr Cys Ser Arg Ile Lys Tyr Arg Met Gln Lys
545                 550                 555                 560

Ser Ala Ala Asp Gly Thr Val Ser Ser Glu Ile Val Glu Thr Thr Pro
                565                 570                 575

Gly Arg Leu Ile Leu Trp Gln Ile Phe Pro Gln His Lys Asp Leu Thr
            580                 585                 590

Phe Asp Leu Ile Asn Gln Val Leu Thr Val Lys Glu Ile Thr Ser Ile
        595                 600                 605

Val Asp Leu Val Tyr Arg Ser Cys Gly Gln Arg Glu Thr Val Glu Phe
610                 615                 620

Ser Asp Lys Leu Met Tyr Trp Gly Phe Lys Tyr Ala Ser Gln Ser Gly
625                 630                 635                 640

Ile Ser Phe Gly Cys Lys Asp Met Ile Ile Pro Asp Thr Lys Ala Ala
                645                 650                 655

His Val Glu Asp Ala Ser Glu Lys Ile Arg Glu Phe Ser Ile Gln Tyr
            660                 665                 670

Gln Asp Gly Leu Ile Thr Lys Ser Glu Arg Tyr Asn Lys Val Val Asp
        675                 680                 685

Glu Trp Ser Lys Cys Thr Asp Leu Ile Ala Arg Asp Met Met Lys Ala
690                 695                 700

Ile Ser Leu Cys Asp Glu Pro Ala Arg Ser Gly Ala Pro Asp Thr
705                 710                 715

<210> SEQ ID NO 60
<211> LENGTH: 439
<212> TYPE: PRT
<213> ORGANISM: Ehrlichia sp.

<400> SEQUENCE: 60

Ile His Ser Ala Tyr Asn Met Leu His Asp Cys Ala Thr Ala Gln Cys
 1               5                  10                  15

Asn Lys Glu Val Pro Arg Phe Met Asp Pro Asp Phe Thr Arg Arg Glu
                20                  25                  30

Val His Leu Gln Ile Ala Lys Val Cys Ala Ile Leu Val Asn Ala Ile
            35                  40                  45

Thr Met Ala Ser Cys Phe Val Thr Thr Leu Thr Glu Ala Ser Asp Ser
        50                  55                  60
```

```
Ala Ile Gly Glu Ala Asp Glu His Ser Ala Tyr His Ala Asn Met Ala
 65                  70                  75                  80

Leu Ser Ala Tyr Val Asn Ala Lys Phe Ser Ala Leu Ser Arg Cys Leu
                 85                  90                  95

Asn Tyr Ser Pro Gly Pro Glu Thr Lys Arg Arg Lys Ala Ile Leu
            100                 105                 110

Arg Val Val Arg His Asn Ile Glu Leu Cys Asn Lys Val Ala Glu Leu
            115                 120                 125

Val Asp Pro Glu Ile Pro Tyr Cys Phe Arg Asp Arg Thr Val Ser Cys
130                 135                 140

Leu Asn Ser Met Leu Asp Ala Val Gly Ser Thr Ser Ala Glu Cys Glu
145                 150                 155                 160

Glu Met Val Ser Asp Asn Asp Ser Ala Lys Asn Arg Leu Ala Leu Ala
                165                 170                 175

Lys Lys Ala Arg Thr Gly Phe Leu His His Phe Lys Thr Tyr Lys Ser
            180                 185                 190

Leu Gly Leu Ser Val Ala Phe Lys Ser Phe Arg His Asp Lys Tyr Val
            195                 200                 205

Gln Ala Leu Val Tyr Ala Ile Gly Ser Leu Phe Ser Met His Arg Val
210                 215                 220

Tyr Ala Ser Thr Gly Asn Thr Gly His Val Val Ala Ser Lys Ile Glu
225                 230                 235                 240

His Cys Leu Gln Met Leu Leu Thr Leu Tyr Lys Tyr Lys Val Arg Arg
                245                 250                 255

Ala Gly Ala Ser Glu Tyr Thr Ala Gln Glu Leu Tyr Leu Asp Met Cys
            260                 265                 270

Thr Val Tyr Asp Glu Ile Gln Glu Cys Val Thr Arg Gly Leu Leu Leu
            275                 280                 285

Asn Pro Gln Thr Glu Val Gly Phe Cys Ser Ala Met Leu Gly Tyr Leu
            290                 295                 300

Ser Ala Met Ile Gly Ile Trp Glu Lys Lys Tyr Glu Arg Tyr Phe Asn
305                 310                 315                 320

Asn Ile Arg Gln Thr Glu Gly Ser Pro Ser Gln Pro Ser Thr Ser Arg
                325                 330                 335

Leu Gly Ser Ala Gly Ala Gly Ile Gly Gly Ser Gln Ala Ser Tyr Thr
            340                 345                 350

Leu Pro His Asp Pro Gly His Met Pro Ser Ser Pro Ser Gln Pro Ser
            355                 360                 365

Thr Ser Gly Leu Gly Gly Asn Pro Ala Gly Gln Gly Ala Leu Gln Ala
    370                 375                 380

Gln Ala Pro Cys Gly Pro Leu Gln Asp Tyr Ser Tyr Ala Gln Pro Ser
385                 390                 395                 400

Thr Ser Gly Leu Gly Gly Ala Ser Ser Thr Leu Glu Gly Ala Gln Val
                405                 410                 415

Val Ser Pro Arg Ser Gln Thr Pro Ser Asp Asp Glu Leu Glu Pro Pro
            420                 425                 430

Ser Arg Arg Ser Arg Ser Ala
            435
```

<210> SEQ ID NO 61
<211> LENGTH: 752
<212> TYPE: PRT
<213> ORGANISM: Ehrlichia sp.

-continued

```
<400> SEQUENCE: 61

Met His Met Pro Arg Ile Phe Thr Thr Pro Val Met Ser Gly Tyr Ala
1               5                   10                  15

Tyr Ser Gly Cys Ser Ser Ala Glu Tyr Lys Glu Thr Val Cys Asn Ser
            20                  25                  30

Ile Met Thr Asn Ser Arg Pro Tyr Ala Ala Cys Leu Gln Ala Ile Arg
        35                  40                  45

Gln Cys Met Leu Glu Leu Arg Asp Thr Phe Val Lys Leu Arg Gly Val
50                  55                  60

Asp Val Val Phe Ala Ala Asp Lys Ile Asp Ser Ile Asn Ser Cys
65                  70                  75                  80

Ile Thr Ala Ala Glu Gly Ala Ser Ser Ala Glu Pro Gly Val Leu Tyr
                85                  90                  95

Ser Leu Ile Asn Arg Leu Tyr Asp Ala Leu Gln Asp Cys Ile Thr Ala
            100                 105                 110

Gln Cys Asn Lys Glu Val Pro Leu Phe Met Asp Gln Asp Phe Ile Lys
        115                 120                 125

Arg Lys Ala His Leu Gln Ile Gly Lys Ala Cys Ala Ile Ile Val Asn
130                 135                 140

Val Ile Ala Ile Val Asn Cys Cys Ala Arg Thr Ile Ala Thr Arg Phe
145                 150                 155                 160

Thr Gly Ala Val Ser Ser Glu Arg Arg Asp Gly Ser Ala Ser His Thr
                165                 170                 175

Val Thr Ala Leu Ser Ala Tyr Cys Tyr Val Lys Phe Ser Ala Leu Ser
            180                 185                 190

Arg Cys Leu Asn Ser Ser Leu Asp Ser Glu Thr Glu Asn Ile Lys
            195                 200                 205

Ala Ile Leu Arg Val Val Arg His Asn Ile Glu Leu Cys Ser Lys Val
210                 215                 220

Ala Glu Leu Val Glu Pro Asn Thr Pro Arg Phe Phe Arg His Arg Thr
225                 230                 235                 240

Glu Ala Cys Leu Asp Ser Val Ile Asp Ala Ile Glu Thr Ser Ala Ala
                245                 250                 255

Ala Cys Glu Ala Met Val Arg Asn Asn Glu Ser Ala Arg Leu Arg Leu
            260                 265                 270

Gly Leu Ser Arg Arg Ala Met Ala Asn Phe Leu Tyr Tyr Leu Glu Ala
        275                 280                 285

Tyr Val Glu Gly Leu Gly Val His Ser Phe Asp Leu Arg Leu Lys Arg
    290                 295                 300

Glu Arg Tyr Arg Gly Gly Ala Leu Val His Ala Val Gly Gly Leu Phe
305                 310                 315                 320

Leu Met Tyr Arg Val Tyr Ala Ser Thr Gly Asn Val Asp His Val Val
                325                 330                 335

Ala Gly Arg Ile Gly His Cys Leu Gln Ile Leu Cys Ala Leu Tyr Ser
            340                 345                 350

Arg Arg Arg Glu Leu Gly Ala Tyr Arg Ala Arg Lys Ser Phe Leu Asp
        355                 360                 365

Met Cys His Val Tyr Glu Glu Ile Asn Glu His Ile Thr Glu Asp Ala
    370                 375                 380

Leu Leu Ile Pro Gln Ile Glu Val Lys Trp Arg Asn Thr Ala Leu Arg
385                 390                 395                 400

Tyr Leu Ser Val Met Met Asn Ile Cys Asp Lys Lys Tyr Gly Arg Tyr
                405                 410                 415
```

```
Phe Asn Ala Val Glu Gln Thr Gly Ala Ala Pro Ser Gln Pro Ser Thr
                420                 425                 430
Ser Gly Leu Gly Ser Thr Ser Ala Gly Val Glu Gly Ala Gln Ala Ile
            435                 440                 445
Ser Val Pro Leu Arg Val Leu Glu Arg Ile Pro Ile Pro Tyr Gly Ala
        450                 455                 460
Pro Trp Asp Gln Pro Ser Thr Ser Gly Met Gly Thr Ala Gly Thr
465                 470                 475                 480
Gly Ser Gln Gln Ala Ser His Ile Pro␣␣His Asp Pro Gly Met Met
                485                 490                 495
Pro Tyr Ser Tyr Ala Gln Pro Ser Thr Leu Trp Asp Gln Pro Ser Thr
                500                 505                 510
Ser Gly Leu Gly Ser Ala Ala Gly Thr Gly Ser Gln Gln Ala Ser His
            515                 520                 525
Ile Pro Pro His Asp Pro Gly Met Met Pro Tyr Ser Tyr Ala Gln Pro
        530                 535                 540
Ser Thr Ser Trp Asp Gln Pro Ser Thr Ser Gly Leu Gly Ser Ala Ala
545                 550                 555                 560
Gly Met Gly Ser Gln Gln Ala Ser His Ile Pro Pro His Asp Pro Gly
                565                 570                 575
Met Met Pro Tyr Ser Tyr Ala Gln Pro Ser Thr Ser Trp Asp Gln Pro
                580                 585                 590
Ser Thr Ser Gly Leu Gly Ser Ala Ala Gly Met Gly Ser Gln Gln Ala
            595                 600                 605
Ser His Ile Pro Pro His Asp Pro Gly Met Met Pro Tyr Ser Tyr Ala
        610                 615                 620
Gln Pro Ser Thr Ser Trp Asp Gln Pro Ser Thr Ser Trp Asp Gln Pro
625                 630                 635                 640
Ser Thr Ser Gly Leu Gly Gly Thr Ala Gly Gln Gly Ala Gln Leu Val
                645                 650                 655
Pro Pro Pro Pro His Ile Ile Leu Arg Val Leu Glu Asn Val Pro Tyr
                660                 665                 670
Pro Ser Ser Gln Phe Ser Thr Ser Gly Leu Gly Gly Thr Ser Thr Gly
            675                 680                 685
Met Gly Arg Ser Gln Ala Pro Tyr Val Pro Pro Gln Asp Gln Gly Ile
        690                 695                 700
Met Pro Tyr Ser Trp Asp Gln Pro Ser Ala Ser Gly Leu Gly Gly Ala
705                 710                 715                 720
Ser Tyr Thr Leu Glu Glu Ala Gln Val Ser Ser His Arg Pro Arg Thr
                725                 730                 735
Pro Ser Asp Asp Asp Ser Glu Pro Pro Ser Lys Gln Ala Arg Arg Ala
                740                 745                 750

<210> SEQ ID NO 62
<211> LENGTH: 110
<212> TYPE: PRT
<213> ORGANISM: Ehrlichia sp.

<400> SEQUENCE: 62

Met Tyr Thr Val Ser Asp Ser Glu Ser Ile Thr Ser Phe Val Thr Pro
  1               5                  10                  15
Pro Met Leu Met Ala Asn Ile Ser Ser Thr Lys Arg Ser Gly Tyr Leu
                20                  25                  30
Leu Ser Leu Ser Val Glu Pro Ser Asp Phe Phe Thr Val Thr Phe Phe
```

-continued

```
        35                  40                  45

Leu Lys Glu Thr Pro Phe Thr Thr Asp Asn Ser Val Pro Phe Cys Ser
    50                  55                  60

Phe Glu Arg Asn Ser Thr Ala Asn Ser Arg Ile Phe Phe Ile Arg Asn
65                  70                  75                  80

Ala Leu Phe His Ser Ser Val Arg Ile Asp Leu Leu Ser Ser Ser Val
                85                  90                  95
Leu Gly Leu Gly Gly Thr Thr Ser Val Thr Arg Thr Pro Lys
            100                 105                 110

<210> SEQ ID NO 63
<211> LENGTH: 149
<212> TYPE: PRT
<213> ORGANISM: Ehrlichia sp.

<400> SEQUENCE: 63

Asp Gly Phe Pro Thr Ala Asp Glu Asn Ala Lys Val Val Lys Ala Phe
 1               5                  10                  15

Ile Pro Ser Cys Asn Gly Lys Ser Phe Thr Lys Leu Pro Asp Leu Ser
            20                  25                  30

Ser Pro Cys Ile Ser Lys Phe Val Lys Thr Pro Leu Ile Arg Ala Pro
        35                  40                  45

Asn Ile Ser Phe Ser Ser Phe Ser Asn Ala Pro Arg Leu Ile Ile Ser
    50                  55                  60

Phe Ala Phe Phe Thr Leu Leu Thr Ser Asn Ser Pro Ala Phe Cys Leu
65                  70                  75                  80

Leu Ile Phe Glu Asp Ile Phe Ser Phe Ser Phe Ser Arg Ser Ser Leu
                85                  90                  95
Val Ile Ser Cys Phe Leu Ile Thr Phe Met Ile Cys Gln Pro Thr Thr
            100                 105                 110
Leu Arg Asn Ile Ser Leu Thr Ser Pro Ser Phe Ser Ala Asn Thr Thr
        115                 120                 125
Phe Arg Thr Pro Thr Gly Arg Thr Ser Leu Glu Ile Leu Leu Ser Ala
    130                 135                 140

Ile Ser Ser Met Val
145

<210> SEQ ID NO 64
<211> LENGTH: 590
<212> TYPE: PRT
<213> ORGANISM: Ehrlichia sp.

<400> SEQUENCE: 64

Leu Leu Tyr Ser Phe Gly Asn Leu Thr Ser Tyr Gly Arg Ser Val Met
 1               5                  10                  15

Arg Ser Arg Lys Ile Tyr Val Trp Val Val Met Ala Thr Val Leu Gly
            20                  25                  30

Ala Met Ala Phe Val Thr Phe Gly Ser Met Ile Pro Met Gly Lys Leu
        35                  40                  45

Ser Asn Ser Gly Asn Gly Gln Cys Val Ala Met Leu Gly Asn Lys Cys
    50                  55                  60

Leu Pro Leu Arg Asp Tyr Arg Ile Met Tyr Arg Asn Glu Leu Ala Glu
65                  70                  75                  80

Leu Glu Lys Met Leu Gln His Lys Leu Ser Asp Ala Gln Ile Asn Gln
                85                  90                  95

Phe Gly Ile Lys Glu Val Val Leu Lys Asn Met Ile Ala Asp Met Val
```

-continued

```
                100                 105                 110
Val Glu Lys Phe Ala His Asp Leu Gly Ile Arg Val Gly Ser Asn Ser
            115                 120                 125

Leu Arg Ser Leu Ile Lys Asn Ile Arg Ile Phe Gln Asp Ala Asn Gly
            130                 135                 140

Val Phe Asp Gln Glu Arg Tyr Glu Ala Val Leu Ala Asp Ser Gly Met
145                 150                 155                 160

Thr Glu Ser Ser Tyr Val Asn Lys Ile Arg Asn Ala Leu Pro Ser Thr
                165                 170                 175

Ile Leu Met Glu Cys Leu Phe Pro Asn Arg Ala Glu Leu His Ile Pro
                180                 185                 190

Tyr Tyr Asp Ala Leu Ala Lys Asp Val Val Leu Gly Leu Leu Gln His
            195                 200                 205

Arg Val Ala Asp Ile Val Glu Ile Ser Ser Asp Ala Val Asp Ile Ser
            210                 215                 220

Gly Ser Asp Ile Ser Asp Asp Glu Leu Gln Lys Leu Phe Glu Glu Gln
225                 230                 235                 240

Tyr Lys Asn Ser Leu Asn Phe Pro Glu Tyr Arg Ser Ala Asp Tyr Ile
                245                 250                 255

Ile Met Ala Glu Asp Asp Leu Leu Ala Asp Val Ile Val Ser Asp Gln
                260                 265                 270

Glu Val Asp Val Glu Ile Lys Asn Ser Glu Leu His Asp Gln Arg Asp
            275                 280                 285

Val Leu Asn Leu Val Phe Thr Asp Lys Asn Glu Ala Glu Leu Ala Tyr
            290                 295                 300

Lys Ala Tyr Gln Glu Gly Lys Ser Phe Glu Glu Leu Val Ser Asp Ala
305                 310                 315                 320

Gly Tyr Thr Ile Glu Asp Ile Ala Leu Asn Asn Ile Ser Lys Asp Val
                325                 330                 335

Leu Pro Val Gly Val Arg Asn Val Val Phe Ala Leu Asn Glu Gly Glu
                340                 345                 350

Val Ser Glu Met Phe Arg Ser Val Gly Trp His Ile Met Lys Val
            355                 360                 365

Ile Arg Lys His Glu Ile Thr Lys Glu Asp Leu Glu Lys Leu Lys Glu
            370                 375                 380

Lys Ile Ser Ser Asn Ile Arg Arg Gln Lys Ala Gly Glu Leu Leu Val
385                 390                 395                 400

Ser Asn Val Lys Lys Ala Asn Asp Met Ile Ser Arg Gly Ala Leu Leu
                405                 410                 415

Asn Glu Leu Lys Asp Met Phe Gly Ala Arg Ile Ser Gly Val Leu Thr
                420                 425                 430

Asn Phe Asp Met His Gly Leu Asp Lys Ser Gly Asn Leu Val Lys Asp
            435                 440                 445

Phe Pro Leu Gln Leu Gly Ile Asn Ala Phe Thr Thr Leu Ala Phe Ser
450                 455                 460

Ser Ala Val Gly Lys Pro Ser His Leu Val Ser Asn Gly Asp Ala Tyr
465                 470                 475                 480

Phe Gly Val Leu Val Thr Glu Val Val Pro Pro Arg Pro Arg Thr Leu
                485                 490                 495

Glu Glu Ser Arg Ser Ile Leu Thr Glu Glu Trp Lys Ser Ala Leu Arg
                500                 505                 510

Met Lys Lys Ile Arg Glu Phe Ala Val Glu Leu Arg Ser Lys Leu Gln
            515                 520                 525
```

```
Asn Gly Thr Glu Leu Ser Val Val Asn Gly Val Ser Phe Lys Lys Asn
        530                 535                 540

Val Thr Val Lys Lys Ser Asp Gly Ser Thr Asp Asn Asp Ser Lys Tyr
545                 550                 555                 560

Pro Glu Arg Leu Val Asp Glu Ile Phe Ala Ile Asn Ile Gly Gly Val
                565                 570                 575

Thr Lys Glu Val Ile Asp Ser Glu Ser Glu Thr Val Tyr Ile
                580                 585                 590

<210> SEQ ID NO 65
<211> LENGTH: 245
<212> TYPE: PRT
<213> ORGANISM: Ehrlichia sp.

<400> SEQUENCE: 65

Gly Ser Cys Cys Tyr Glu Val Asp Gly Met Ala Lys Arg Phe Leu Asn
1               5                   10                  15

Asp Thr Glu Lys Lys Leu Leu Ser Leu Leu Lys Ser Val Met Gln His
            20                  25                  30

Tyr Lys Pro Arg Thr Gly Phe Val Arg Ala Leu Leu Ser Ala Leu Arg
        35                  40                  45

Ser Ile Ser Val Gly Asn Pro Arg Gln Thr Ala His Asp Leu Ser Val
    50                  55                  60

Leu Val Thr Gln Asp Phe Leu Val Glu Val Ile Gly Ser Phe Ser Thr
65                  70                  75                  80

Gln Ala Ile Ala Pro Ser Phe Leu Asn Ile Met Ala Leu Val Asp Glu
                85                  90                  95

Glu Ala Leu Asn His Tyr Asp Arg Pro Gly Arg Ala Pro Met Phe Ala
            100                 105                 110

Asp Met Leu Arg Tyr Ala Gln Glu Gln Ile Arg Arg Gly Asn Leu Leu
        115                 120                 125

Gln His Arg Trp Asn Glu Glu Thr Phe Ala Ser Phe Ala Asp Ser Tyr
    130                 135                 140

Leu Arg Arg Arg His Glu Arg Val Ser Ala Glu His Leu Arg Gln Ala
145                 150                 155                 160

Met Gln Ile Leu His Ala Pro Ala Ser Tyr Arg Val Leu Ser Thr Asn
                165                 170                 175

Trp Phe Leu Leu Arg Leu Ile Ala Ala Gly Tyr Val Arg Asn Ala Val
            180                 185                 190

Asp Val Val Asp Ala Glu Ser Ala Gly Leu Thr Ser Pro Arg Ser Ser
        195                 200                 205

Ser Glu Arg Thr Ala Ile Glu Ser Leu Leu Lys Asp Tyr Asp Glu Glu
    210                 215                 220

Gly Leu Ser Glu Met Leu Glu Thr Glu Lys Gly Val Met Thr Ser Leu
225                 230                 235                 240

Phe Gly Thr Val Leu
                245

<210> SEQ ID NO 66
<211> LENGTH: 456
<212> TYPE: PRT
<213> ORGANISM: Ehrlichia sp.

<400> SEQUENCE: 66

Lys Ala Ile Pro Glu Ala Glu Lys Ile Phe Glu Lys Ala Met Asn Ile
1               5                   10                  15
```

-continued

```
Ala Asp Lys Val Tyr Gly Ser Ala Ser Ser Glu Val Lys Ser Leu Phe
            20                  25                  30

Thr Cys Pro Asn Pro Glu Asp Ala Ser Thr Leu Val His Phe Val Ser
            35                  40                  45

Ser Asn Gly Thr Pro Asn Phe Asp Pro Leu Ala Lys Arg Val Leu Glu
 50                      55                  60

Glu Ala Tyr His Arg Tyr Gly Glu Glu Pro Phe Thr Asn Leu Asp Ile
 65                  70                  75                  80

Ala Gly Asn Ala Pro Ile His Ala Ala Gln Lys Ser Thr Val Gly
                 85                  90                  95

Val Phe Glu Gln Val Val Arg Cys Thr Pro Glu Ser Val Val Asn Gln
                100                 105                 110

Leu Ala Pro Asn Gly Lys Ala Pro Ile His Met Ile Val Glu Asp Glu
                115                 120                 125

Pro Ser His Lys Gly Val Ser Val Lys Leu Gln Met Leu Ile Glu Asn
            130                 135                 140

Val Arg Asn Ile Pro Ser Ile Asn Val Pro Ser Pro Val Thr Gly Glu
145                 150                 155                 160

Thr Pro Val Val Ala Ala Tyr Lys Gly Gly Asn Thr Glu Gly Val Lys
                165                 170                 175

Thr Met Leu Arg Cys Asn Ser Met Asp Val Asp Ala Arg Ser His Asp
                180                 185                 190

Gly Gly Thr Ile Ile His Tyr Ala Ala Lys Asp Gly Asn Leu Glu Ile
            195                 200                 205

Leu Gln Gln Ala Leu Gly Arg Lys Ser Ser Tyr Ser Lys Phe Pro Val
    210                 215                 220

Lys Asp Gly Val Pro Thr Pro Gly Val Tyr Ala Ile Arg Glu Ala Ser
225                 230                 235                 240

Gly Gly Lys Val Ser Leu Pro Ala Leu Asp Met Leu Met Arg Tyr Glu
                245                 250                 255

Pro Tyr Pro Gln His Val Ala Val Glu Ala Val Arg Lys Gly Ala Ala
                260                 265                 270

Asp Val Leu Arg His Leu Ile Thr Thr Glu Val Ile Ser Val Asn Glu
            275                 280                 285

Glu Ile Thr Thr Pro Glu Gly Lys Lys Thr Thr Leu Thr Ala Glu Ala
    290                 295                 300

Leu Thr Ser Gly Gln Tyr Ala Ala Val Lys Thr Leu Ile Lys Asn Ser
305                 310                 315                 320

Ala Asp Val Asn Ala Ser Pro Glu Pro Ala Ile Ser Val Gly Ile Gln
                325                 330                 335

Gly Gly Cys Phe Gln Gly Gly Lys Ala Ile Lys His Leu Lys Arg Val
            340                 345                 350

Val Glu Ala Gly Ala His Ile Asn Thr Pro Thr Gly Ser Met Ser Pro
            355                 360                 365

Leu Ala Ala Ala Val Gln Val Ala Asn Glu Ala Ser Asn Leu Lys Glu
    370                 375                 380

Ala Asn Arg Ile Val Asn Phe Leu Leu Gln Arg Gly Ala Asp Leu Ser
385                 390                 395                 400

Ser Thr Asp His Thr Gly Thr Pro Ala Leu His Leu Ala Thr Ala Ala
                405                 410                 415

Gly Asn Gln Lys Thr Ala Arg Leu Leu Leu Asp Lys Gly Ala Pro Ala
            420                 425                 430
```

-continued

```
Thr Gln Arg Asp Ala Tyr Gly Lys Thr Ala Leu His Ile Ala Ala Ala
            435                 440                 445

Asn Gly Asp Gly Lys Leu Tyr Lys
    450                 455

<210> SEQ ID NO 67
<211> LENGTH: 113
<212> TYPE: PRT
<213> ORGANISM: Ehrlichia sp.

<400> SEQUENCE: 67

Asp Gly Asn Thr Pro Leu His Thr Ala Ala Ser Ser Val Gly Lys Asn
  1               5                  10                  15

Ala Leu Gly Asn Leu Asp Val Leu Cys Asp Lys Ala Leu Ile Ala Asp
             20                  25                  30

Val Asn Ala Lys Gly Pro Gly Gly Asn Thr Pro Leu His Ile Ala Thr
         35                  40                  45

Glu Arg Met Asp His Gln Lys Val Lys His Leu Leu Ser Arg Leu Ser
     50                  55                  60

Asp Ile Ser Val Ala Asn Asp Ala Gly Glu Thr Val Cys His Ile Val
 65                  70                  75                  80

Ala Lys Gln Trp Pro Arg Arg Asp Val Leu Ser Tyr Ile Asp Lys Met
                 85                  90                  95

Gln Glu Ala Val Ser Ser Asn Ile Glu Gly Asn Arg Ser Val Gln Arg
                100                 105                 110

His

<210> SEQ ID NO 68
<211> LENGTH: 623
<212> TYPE: PRT
<213> ORGANISM: Ehrlichia sp.

<400> SEQUENCE: 68

Asp Glu Ala Pro Met Thr Leu Leu Lys Gln Asn Pro Ser Lys Ala
  1               5                  10                  15

Ser Val Ala Leu Leu Gly Ser Ala Ile Asp Phe Phe Leu Cys Arg Asp
             20                  25                  30

Arg Asn Ser His Pro Ala Arg Arg Met Val Ile Leu Leu Ala Glu
             35                  40                  45

Gly Phe Thr Leu Arg Glu Gly Ser Ala Val Pro Pro Ala Leu Ile His
     50                  55                  60

Glu Asn Leu Thr Ser Pro Asp Leu Leu Ala Arg Ala Leu His Lys Thr
 65                  70                  75                  80

Ala Ser Asn Ser Thr Ala Phe Gln Gln Val Pro Phe Gln Leu Trp His
                 85                  90                  95

Ala Leu Ala Leu Ala Tyr Asn Ser Leu Pro Gly Lys Asn Gln Glu Glu
                100                 105                 110

Asp Leu Thr Asn Phe Val Leu Gly Cys Leu Asp Gly Val Ser Glu Asp
            115                 120                 125

Met Thr Ile Val Arg Glu Glu Asp Ser Thr Phe Glu Val Gln Ser
    130                 135                 140

Tyr Thr Thr Phe Ser Arg Val His Ser Leu Leu Ala Ser Ala Pro Ser
145                 150                 155                 160

Ser Tyr Lys Asn Gly Ala Leu Thr Val His Glu Ser Cys Ile Phe Ser
                165                 170                 175

Ile Gln Asp Asn Ser Gly Val Pro Ile Ala Lys Val Lys Met Trp Val
```

```
                  180              185              190
Glu Tyr Asp Ile Ala Pro Ser Thr Lys Ala Glu Gly Val Tyr Arg Thr
        195              200              205
Ala Val Lys Lys Val Lys Leu Val Leu Thr Glu Arg Asp Cys Arg Asp
        210              215              220
Val Arg Gln Gly Glu Pro Gly Ser Val Cys Ser Trp His Asn Ile Pro
225              230              235              240
Lys Ala Leu Ala Lys His Tyr Val Arg Val Pro Glu Lys Pro Thr His
                245              250              255
Val Leu Tyr Ser Ala Cys Asn Leu Gln Arg His Asn Pro Arg Tyr Met
                260              265              270
Ala Arg Arg Val Phe Tyr Asp Val Ser Asp Ile Asp Glu Cys Ile Leu
        275              280              285
Arg Ala Tyr Ser Val Ile Ser Gly Met Pro Leu Glu Val Leu Glu Leu
        290              295              300
Ser Phe Cys Asn Thr Val Ile Ser Gln Glu Ala Ser Gly Val Phe Arg
305              310              315              320
Val Val Val Arg Gly Val Gly Leu Val Gly Tyr Asp Lys Ser Ser
                325              330              335
Val Val Gln Gln Gly Ala Val Ser His Gly Arg Asp Ala Val Ser Lys
                340              345              350
Met Gly Val Cys Met Ser Phe Val Ala Ser Gln Ala His Asp Ala Cys
        355              360              365
Ala Thr Ile Leu Arg His Val Ala Val Thr Val Asn Thr Phe Gly Asn
        370              375              380
Val Leu Thr Leu Gly Gly Gly Ile Ser Leu Arg Asp Phe Leu Ala Gly
385              390              395              400
Ser Ala Lys Asp Thr Asp Phe Ala Gly Gly His Ile Phe Asn Leu Ala
                405              410              415
Glu Glu Ile Val Ala His Gly Leu Ser Leu Trp Glu Asp Leu Gly Lys
                420              425              430
Arg His Arg Trp Ala Ser His Ser Val Pro Val Arg Gly Asp Cys Gly
        435              440              445
Ile Phe Ile Gln His Ser Asp Glu Ile Arg Glu Ile Leu Arg Ser Gln
        450              455              460
Pro Lys His Ala Ala Asn Ile Val Glu Lys Thr Gly Val Asn Thr Glu
465              470              475              480
Asn Leu Arg Val Leu Leu Ser Ser Ile Leu Ser Asn Ser Ser Gly Ser
                485              490              495
Ser Leu Pro Val Glu Leu Ala Ala His Tyr Val Ala His Glu Gly Val
                500              505              510
Val Ala Asp Asn Gly Asp Ser Ala Arg Arg Leu Pro Val Asn Gln His
                515              520              525
Val Leu Glu Glu His Leu Val Tyr Arg Val Thr Ser Val Ser Gly Ile
                530              535              540
His Ile His Ala Cys Val Asp Tyr Val Val Glu Asp Ile Asp Thr Pro
545              550              555              560
Gly Ser Val Lys Asp Leu Gly Leu Cys Ile Arg Asp Val Arg Ile Gly
                565              570              575
Thr Arg Val Ala Ser Ser Ala Glu Glu Val Cys Ser Ala Ile Gln Glu
                580              585              590
Lys Glu Gly Arg Ile Asp Arg Asn Asp Phe Ala Trp Phe Asn Val Asp
        595              600              605
```

```
Gln Ser Leu Val Glu Thr Ser Arg Ala Glu Phe Arg Ala Ala Ile
    610                 615                 620

<210> SEQ ID NO 69
<211> LENGTH: 464
<212> TYPE: PRT
<213> ORGANISM: Ehrlichia sp.

<400> SEQUENCE: 69

Arg Ile His Met Arg Lys Glu Asn Ser Lys Ala Ala Tyr Cys Val Thr
  1               5                  10                  15

Trp Arg Phe Lys Leu Arg Lys Lys Asn Thr His Asn Gly Ser Arg Arg
             20                  25                  30

Thr Val Ser Gly Ile Leu Asn Tyr Leu Arg Ala Leu Phe Phe Arg Ile
         35                  40                  45

Ile Ser Ile Phe Ser Thr Ser Ser Ala Val Ser Lys Ala Glu Asp
 50                  55                  60

Glu Ala Asn Ser Val His Ile Cys Thr His Asn Ser Ser Asp Ala Ser
 65                  70                  75                  80

Lys Asp Ser Lys Ala Lys His Lys Asp His Arg Pro Ser Ile Asp Val
                 85                  90                  95

Ser Leu Lys Tyr Ser Gln Lys Lys Trp Leu Glu Gly Ala Ser Gly
             100                 105                 110

Phe Ser Phe His Ser Ala Leu Cys Asp Ser Tyr Lys Asn Lys Ser Asn
         115                 120                 125

Leu Tyr Gly His Gln Phe Leu Ile Asp Met His Arg Cys Asp Trp Cys
     130                 135                 140

Ile Asn Lys Thr Phe Tyr Pro Arg Gln Asn Val Ser Ala His Ile Ala
145                 150                 155                 160

Arg Leu Glu Arg Ser Ile Lys Ser Ser Ser Ile Thr Asn Leu Asn Leu
                165                 170                 175

Val Cys Gln Arg Thr Tyr Gly Val Ser Arg Gly Val Phe Leu Arg Arg
            180                 185                 190

Tyr Arg Glu Arg Ser Leu Ala Ile Ala Met Leu Gln Lys Met Phe Arg
        195                 200                 205

Asp Asp Arg His Gly Val Val Pro Asp Ile Arg Leu Leu Asp Glu Ile
    210                 215                 220

Ala Ser His Cys His Gln Gly Gly Leu Ser Ala Trp Val Cys Phe Asp
225                 230                 235                 240

Val Ile Trp Pro Ile Lys His Ala Leu Asp Lys Glu Tyr Phe Phe Ser
                245                 250                 255

Asp Ala Gly Ala Thr Leu Asn Leu Leu Asn Arg Ile Tyr Val Ser Ala
            260                 265                 270

Cys Ser Asn Ile Lys Gln Val Asp Ala Ile Thr Pro Glu Arg Ile Ala
        275                 280                 285

Val Cys Glu Asn Leu Asp Phe Leu Leu Lys Val Pro Gln Ser Thr Glu
    290                 295                 300

Gly Glu Lys Thr Pro Ala Phe Lys Val Asn Thr Ala Leu Lys Tyr Glu
305                 310                 315                 320

Ile Ser Ile Gln Gly Glu Gly Arg Val Leu Tyr Asp Asn Cys Ser Leu
                325                 330                 335

Asn Leu Thr Ile Ile Thr Pro Pro Asp Cys Asn Ile Lys Thr Ser Pro
            340                 345                 350

Pro Leu Leu Phe Arg Val Cys Pro Pro Leu Gly Arg Leu Leu Leu Arg
```

-continued

```
                355                 360                 365
Leu Lys His Arg Phe Tyr Lys Arg Lys Val Phe Thr Pro Gln Asp Thr
        370                 375                 380

Arg Val Pro Asp Pro Thr Leu Val Arg Val Gln Arg Ile Pro Cys Ile
385                 390                 395                 400

Gly Met Asn Ile Thr Lys Leu Gln Tyr Ala Met Ala Pro Leu Pro Val
                    405                 410                 415

Ser Pro Glu Glu Phe Phe Arg Asp Leu Val Lys Asn Ser Thr Ile Cys
                420                 425                 430

Gly Ile Tyr Ile Met Thr Ser Leu Arg Lys Cys Ile Trp Gln Ser
                    435                 440                 445

Leu Asn Pro Asn Met Leu Arg Leu Met Phe Leu Arg His Met Met Met
        450                 455                 460
```

<210> SEQ ID NO 70
<211> LENGTH: 378
<212> TYPE: PRT
<213> ORGANISM: Ehrlichia sp.

<400> SEQUENCE: 70

```
Ile Leu Arg Phe Ser Asp Asp Phe Pro Asp Ala Lys Val Ile Arg Leu
1               5                   10                  15

Glu Cys Asn Tyr Arg Ser Thr Ser Asn Ile Leu Ala Ser Ala Ser Ala
                20                  25                  30

Ile Ile Asp Asn Asn Lys Ser Arg Leu Lys Lys Thr Leu Trp Thr His
            35                  40                  45

Asn Gln Ala Gly Gln Lys Val Gly Leu Met Lys Phe Phe Asp Gly Arg
        50                  55                  60

Leu Glu Ala Gln Tyr Ile Ser Glu His Ile Lys Ser Ser Tyr Asp Tyr
65                  70                  75                  80

Lys Phe Ser Glu Thr Ala Val Leu Val Arg Ala Ser Phe Gln Thr Arg
                85                  90                  95

Val Phe Glu Glu Phe Phe Val Arg Tyr Gly Ile Pro Tyr Lys Ile Ile
                100                 105                 110

Gly Gly Thr Lys Phe Tyr Asp Arg Val Glu Ile Arg Asp Leu Val Ala
            115                 120                 125

Tyr Leu Lys Val Val Val Asn Pro Asn Asn Asp Ile Ala Phe Glu Lys
        130                 135                 140

Ile Ile Asn Lys Pro Lys Arg Lys Leu Gly Thr Ser Thr Val Asn Lys
145                 150                 155                 160

Leu Arg Ala Tyr Gly Arg Lys His Ser Ile Ser Leu Thr Glu Ala Gly
                165                 170                 175

His Ser Met Ile Lys Asp Gly Leu Leu Ser Asp Asn Thr Ser Asn Ile
                180                 185                 190

Leu Gln Asp Leu Leu Lys Gln Phe Asp Asp Trp Arg Glu Met Leu Ser
        195                 200                 205

Arg Asp Ser Ser Val Asn Val Leu Lys Ala Ile Ala His Asp Ser Gly
        210                 215                 220

Tyr Ile Glu Ser Leu Lys Lys Asp Gly Glu Ser Gly Leu Ser Arg Ile
225                 230                 235                 240

Glu Asn Ile Lys Glu Leu Phe Ser Ala Val Ser Gly Phe Asp Val
                245                 250                 255

Ser Lys Phe Leu Glu His Ile Ser Leu Val Ala Glu Asn Asp Ser Leu
            260                 265                 270
```

```
Glu Glu Asp Asn Asn Tyr Val His Val Met Thr Leu His Ala Ala Lys
            275                 280                 285

Gly Leu Glu Phe Pro Leu Val Phe Leu Pro Gly Trp Glu Glu Gly Val
        290                 295                 300

Phe Pro His Glu Lys Ser Met Asn Asp Ile Thr Gly Asn Ala Leu Glu
305                 310                 315                 320

Glu Glu Arg Arg Leu Ala Tyr Val Gly Ile Thr Arg Ala Arg Glu Gln
                325                 330                 335

Leu Tyr Ile Ser Cys Ala Ala Met Arg Glu Ile Asn Asn Trp Ser Gln
            340                 345                 350

Ser Met Lys Met Ser Arg Phe Ile Lys Glu Leu Pro Arg Glu His Val
        355                 360                 365

Gln Val Leu His Asn Met Thr Gly Tyr Ala
    370                 375

<210> SEQ ID NO 71
<211> LENGTH: 209
<212> TYPE: PRT
<213> ORGANISM: Ehrlichia sp.

<400> SEQUENCE: 71

Tyr Ile Asp Ser Leu Arg Ser His Ser Leu Leu Lys Arg Lys Thr
1               5                   10                  15

Lys Gly Ile Arg Asp Ser Gly Ser Lys Glu Asp Glu Ala Asp Thr Val
            20                  25                  30

Tyr Leu Leu Ala Lys Glu Leu Ala Tyr Asp Val Val Thr Gly Gln Thr
        35                  40                  45

Asp Asn Leu Ala Ala Ala Leu Ala Lys Thr Ser Gly Lys Asp Phe Val
    50                  55                  60

Lys Phe Ala Asn Ala Val Val Gly Ile Ser His Pro Asp Val Asn Lys
65                  70                  75                  80

Lys Val Cys Ala Thr Arg Lys Asp Ser Gly Gly Thr Arg Tyr Ala Lys
                85                  90                  95

Tyr Ala Ala Thr Thr Asn Lys Ser Ser Asn Pro Glu Thr Ser Leu Cys
            100                 105                 110

Gly Asp Glu Gly Gly Ser Ser Gly Thr Asn Asn Thr Gln Glu Phe Leu
        115                 120                 125

Lys Glu Phe Val Ala Lys Thr Leu Val Glu Asn Glu Ser Lys Asn Trp
130                 135                 140

Pro Thr Ser Ser Gly Thr Gly Leu Lys Thr Asn Asp Asn Ala Lys Ala
145                 150                 155                 160

Val Ala Thr Asp Leu Val Ala Leu Asn Arg Asp Glu Lys Thr Ile Val
                165                 170                 175

Ala Gly Leu Leu Ala Lys Thr Ile Glu Gly Gly Glu Val Val Glu Ile
            180                 185                 190

Arg Ala Val Ser Ser Thr Ser Val Met Ala Leu Glu Leu Arg Val Cys
        195                 200                 205

Trp

<210> SEQ ID NO 72
<211> LENGTH: 261
<212> TYPE: PRT
<213> ORGANISM: Ehrlichia sp.

<400> SEQUENCE: 72

Lys Lys Ser Ile Ile Arg Glu Asp Glu Val Asp Thr Val Tyr Leu Leu
```

```
            1               5                  10                 15
          Ala Lys Glu Leu Ala Tyr Asp Val Val Thr Gly Gln Thr Asp Lys Leu
                       20                  25                 30
          Thr Ala Ala Leu Ala Lys Thr Ser Gly Lys Asp Ile Val Gln Phe Ala
                       35                  40                 45
          Lys Ala Val Gly Val Ser His Pro Ser Ile Asp Gly Lys Val Cys Arg
                50                  55                 60
          Thr Lys Arg Lys Ala Gly Asp Ser Ser Gly Thr Tyr Ala Lys Tyr Gly
           65                  70                  75                 80
          Glu Glu Thr Asp Asn Asn Thr Ser Gly Gln Ser Thr Val Ala Val Cys
                            85                  90                 95
          Gly Glu Lys Ala Gly His Asn Ala Asn Gly Ser Gly Val Gln Ser
                       100                 105                110
          Leu Lys Asp Phe Val Arg Glu Thr Leu Lys Ala Asp Gly Asn Arg Asn
                       115                 120                125
          Trp Pro Thr Ser Arg Glu Lys Ser Gly Asn Thr Asn Thr Lys Pro Gln
                       130                 135                140
          Pro Asn Asp Asn Ala Lys Ala Val Ala Lys Asp Leu Val Gln Glu Leu
           145                 150                 155                160
          Asn His Asp Glu Lys Thr Ile Val Ala Gly Leu Leu Ala Lys Thr Ile
                            165                 170                175
          Glu Gly Gly Glu Val Val Glu Ile Arg Ala Val Ser Ser Thr Ser Val
                       180                 185                190
          Met Val Asn Ala Cys Tyr Asp Leu Leu Ser Glu Gly Leu Gly Val Val
                       195                 200                205
          Pro Tyr Ala Cys Val Gly Leu Gly Gly Asn Phe Val Gly Val Val Asp
                       210                 215                220
          Gly His Ile Thr Ile Arg Trp Ala Ser Thr Leu Tyr Ala His Ser Lys
           225                 230                 235                240
          Ser Leu Gly Lys Ile Gly Ala Ala Ser Leu Arg Asn Arg Leu Arg Ser
                            245                 250                255
          Ala Ile Leu His Thr
                       260

<210> SEQ ID NO 73
<211> LENGTH: 530
<212> TYPE: PRT
<213> ORGANISM: Ehrlichia sp.

<400> SEQUENCE: 73

Leu Leu Tyr Ser Phe Gly Asn Leu Thr Ser Tyr Gly Arg Ser Val Met
           1               5                  10                 15
          Arg Ser Arg Lys Ile Tyr Val Trp Val Val Met Ala Thr Val Leu Gly
                       20                  25                 30
          Ala Met Ala Phe Val Thr Phe Gly Ser Met Ile Pro Met Gly Lys Leu
                       35                  40                 45
          Ser Asn Ser Gly Asn Gly Gln Cys Val Ala Met Leu Gly Asn Lys Cys
                50                  55                 60
          Leu Pro Leu Arg Asp Tyr Arg Ile Met Tyr Arg Asn Glu Leu Ala Glu
           65                  70                  75                 80
          Leu Glu Lys Met Leu Gln His Lys Leu Ser Asp Ala Gln Ile Asn Gln
                            85                  90                 95
          Phe Gly Ile Lys Glu Val Val Leu Lys Asn Met Ile Ala Asp Met Val
                       100                 105                110
```

```
Val Glu Lys Phe Ala His Asp Leu Gly Ile Arg Val Gly Ser Asn Ser
        115                 120                 125

Leu Arg Ser Leu Ile Lys Asn Ile Arg Ile Phe Gln Asp Ala Asn Gly
130                 135                 140

Val Phe Asp Gln Glu Arg Tyr Glu Ala Val Leu Ala Asp Ser Gly Met
145                 150                 155                 160

Thr Glu Ser Ser Tyr Val Asn Lys Ile Arg Asn Ala Leu Pro Ser Thr
                165                 170                 175

Ile Leu Met Glu Cys Leu Phe Pro Asn Arg Ala Glu Leu His Ile Pro
                180                 185                 190

Tyr Tyr Asp Ala Leu Ala Lys Asp Val Val Leu Gly Leu Leu Gln His
        195                 200                 205

Arg Val Ala Asp Ile Val Glu Ile Ser Ser Asp Ala Val Asp Ile Ser
210                 215                 220

Gly Ser Asp Ile Ser Asp Asp Glu Leu Gln Lys Leu Phe Glu Glu Gln
225                 230                 235                 240

Tyr Lys Asn Ser Leu Asn Phe Pro Glu Tyr Arg Ser Ala Asp Tyr Ile
                245                 250                 255

Ile Met Ala Glu Asp Asp Leu Leu Ala Asp Val Ile Val Ser Asp Gln
                260                 265                 270

Glu Val Asp Val Glu Ile Lys Asn Ser Glu Leu His Asp Gln Arg Asp
        275                 280                 285

Val Leu Asn Leu Val Phe Thr Asp Lys Asn Glu Ala Glu Leu Ala Tyr
        290                 295                 300

Lys Ala Tyr Gln Glu Gly Lys Ser Phe Glu Glu Leu Val Ser Asp Ala
305                 310                 315                 320

Gly Tyr Thr Ile Glu Asp Ile Ala Leu Asn Asn Ile Ser Lys Asp Val
                325                 330                 335

Leu Pro Val Gly Val Arg Asn Val Val Phe Ala Leu Asn Glu Gly Glu
                340                 345                 350

Val Ser Glu Met Phe Arg Ser Val Val Gly Trp His Ile Met Lys Val
        355                 360                 365

Ile Arg Lys His Glu Ile Thr Lys Glu Asp Leu Glu Lys Leu Lys Glu
370                 375                 380

Lys Ile Ser Ser Asn Ile Arg Arg Gln Lys Ala Gly Glu Leu Leu Val
385                 390                 395                 400

Ser Asn Val Lys Lys Ala Asn Asp Met Ile Ser Arg Gly Ala Leu Leu
                405                 410                 415

Asn Glu Leu Lys Asp Met Phe Gly Ala Arg Ile Ser Gly Val Leu Thr
                420                 425                 430

Asn Phe Asp Met His Gly Leu Asp Lys Ser Gly Asn Leu Val Lys Asp
        435                 440                 445

Phe Pro Leu Gln Leu Gly Ile Asn Ala Phe Thr Thr Leu Ala Phe Ser
        450                 455                 460

Ser Ala Val Gly Lys Pro Ser His Leu Val Ser Asn Gly Asp Ala Tyr
465                 470                 475                 480

Phe Gly Val Leu Val Thr Glu Val Val Pro Pro Arg Pro Arg Thr Leu
                485                 490                 495

Glu Glu Ser Arg Ser Ile Leu Thr Glu Glu Trp Lys Ser Ala Leu Arg
                500                 505                 510

Met Lys Lys Ile Arg Glu Phe Ala Val Glu Leu Arg Ser Lys Leu Gln
        515                 520                 525

Asn Gly
```

<210> SEQ ID NO 74
<211> LENGTH: 25
<212> TYPE: DNA
<213> ORGANISM: Artificial Sequence
<220> FEATURE:
<223> OTHER INFORMATION: PCR primer used to prepare DNA for fusion
      construct

<400> SEQUENCE: 74 aaagggctc cagcaacgca gagag                                              25

<210> SEQ ID NO 75
<211> LENGTH: 32
<212> TYPE: DNA
<213> ORGANISM: Artificial Sequence
<220> FEATURE:
<223> OTHER INFORMATION: PCR primer used to prepare DNA for fusion
      construct

<400> SEQUENCE: 75
catagaattc gatcgatcga gtagctggaa cc                                     32

<210> SEQ ID NO 76
<211> LENGTH: 28
<212> TYPE: DNA
<213> ORGANISM: Artificial Sequence
<220> FEATURE:
<223> OTHER INFORMATION: PCR primer used to prepare DNA for fusion
      construct

<400> SEQUENCE: 76
caccgtcgat cgttctatat tggtttgg                                          28

<210> SEQ ID NO 77
<211> LENGTH: 32
<212> TYPE: DNA
<213> ORGANISM: Artificial Sequence
<220> FEATURE:
<223> OTHER INFORMATION: PCR primer used to prepare DNA for fusion
      construct

<400> SEQUENCE: 77
cttgactcga gttaaagatg gtttgtgtaa tg                                     32

<210> SEQ ID NO 78
<211> LENGTH: 29
<212> TYPE: DNA
<213> ORGANISM: Artificial Sequence
<220> FEATURE:
<223> OTHER INFORMATION: PCR primer used to prepare DNA for fusion
      construct

<400> SEQUENCE: 78
cttatcgatc ggagcttgag attggttac                                         29

<210> SEQ ID NO 79
<211> LENGTH: 31
<212> TYPE: DNA
<213> ORGANISM: Artificial Sequence
<220> FEATURE:
<223> OTHER INFORMATION: PCR primer used to prepare DNA for fusion
      construct

<400> SEQUENCE: 79
caatgcgaat tcattaaaaa gcgagcctaa c                                      31

```
<210> SEQ ID NO 80
<211> LENGTH: 33
<212> TYPE: DNA
<213> ORGANISM: Artificial Sequence
<220> FEATURE:
<223> OTHER INFORMATION: PCR primer used to prepare DNA for fusion
      construct

<400> SEQUENCE: 80
ctacatcacg tgttctatat tggtttggat tac                                   33

<210> SEQ ID NO 81
<211> LENGTH: 34
<212> TYPE: DNA
<213> ORGANISM: Artificial Sequence
<220> FEATURE:
<223> OTHER INFORMATION: PCR primer used to prepare DNA for fusion
      construct

<400> SEQUENCE: 81
ggttaactcg agtactaaga tggtttgtgt aatg                                  34

<210> SEQ ID NO 82
<211> LENGTH: 27
<212> TYPE: DNA
<213> ORGANISM: Artificial Sequence
<220> FEATURE:
<223> OTHER INFORMATION: PCR primer used to prepare DNA for fusion
      construct

<400> SEQUENCE: 82
gagcttgaga ttggttacga gcgcttc                                          27

<210> SEQ ID NO 83
<211> LENGTH: 32
<212> TYPE: DNA
<213> ORGANISM: Artificial Sequence
<220> FEATURE:
<223> OTHER INFORMATION: PCR primer used to prepare DNA for fusion
      construct

<400> SEQUENCE: 83
caattactcg agaattcatt aaaaagcgag cc                                    32

<210> SEQ ID NO 84
<211> LENGTH: 1980
<212> TYPE: DNA
<213> ORGANISM: Artificial Sequence
<220> FEATURE:
<223> OTHER INFORMATION: DNA fusion construct containing HGE-3 and HGE-1
      antigens

<400> SEQUENCE: 84
atgcagcatc accaccatca ccacgtgttc tatattggtt tggattacag tccagcgttt      60
agcaagataa gagattttag tataagggag agtaacggag agacaaaggc agtatatcca     120
tacttaaagg atggaaagag tgtaaagcta gagtcacaca gtttgactg gaacacacct      180 gatcctcgga ttgggtttaa ggacaacatg cttgtagcta tggaaggtag tgttggttat     240
ggtattggtg gtgccagggt tgagcttgag attggttacg agcgcttcaa gaccaagggt     300
attagagata gtggtagtaa ggaagatgaa gctgatacag tatatctact agctaaggag     360
ttagcttatg atgttgttac tggacagact gataaccttg ctgctgctct tgctaagacc     420
tcggggaaag acatcgttca gtttgctaag gcggttgggg tttctcatcc tagtattgat     480
```

```
gggaaggttt gtaagacgaa ggcggatagc tcgaagaaat ttccgttata tagtgacgaa    540
acgcacacga aggggggcaaa tgaggggaga acgtctttgt gcggtgacaa tggtagttct    600
acgataacaa ccagtggtac gaatgtaagt gaaactgggc aggttttag  ggattttatc    660 agggcaacgc tgaaagagga tggtagtaaa aactggccaa cttcaagcgg cacgggaact    720
ccaaaacctg tcacgaacga caacgccaaa gccgtagcta aagacctagt acaggagcta    780 accccctgaag aaaaaaccat agtagcaggg ttactagcta agactattga aggggggtgaa   840 gttgttgaga tcagggcggt ttcttctact tccgtaatgg tcaatgcttg ttatgatctt    900
cttagtgaag gtttaggtgt tgttccttat gcttgtgttg gtctcggtgg taacttcgtg    960
ggcgtggttg atggaattca ttacacaaac catcttagtg agcttgagat tggttacgag   1020
cgcttcaaga ccaagggtat tagagatagt ggtagtaagg aagatgaagc tgatacagta   1080
tatctactag ctaaggagtt agcttatgat gttgttactg gtcagactga taaccttgcc   1140
gctgctcttg ccaaaacctc cggtaaggat attgttcagt ttgctaaggc ggtggagatt   1200
tctcattccg agattgatgg caaggtttgt aagacgaagt cggcgggaac tggaaaaaat   1260
ccgtgtgatc atagccaaaa gccgtgtagt acgaatgcgt attatgcgag gagaacgcag   1320
aagagtagga gttcgggaaa aacgtcttta tgcggggaca gtgggtatag cgggcaggag   1380
ctaataacgg gtgggcatta tagcagtcca agcgtattcc ggaattttgt caaagacaca   1440
ctacaaggaa atggtagtga aactggcct  acatctactg gagaaggaag tgagagtaac   1500
gacaacgcca tagccgttgc taaggaccta gtaaatgaac ttactcctga agaacgaacc   1560
atagtggctg ggttacttgc taaaattatt gaaggaagcg aggttattga gattagggcc   1620
atctcttcga cttcagttac aatgaatatt tgctcagata tcacgataag taatatctta   1680
atgccgtatg tttgtgttgg tccagggatg agctttgtta gtgttgttga tggtcacact   1740
gctgcaaagt ttgcatatcg gttaaaggca ggtctgagtt ataaattttc gaaagaagtt   1800
acagcttttg caggtggttt ttaccatcac gttataggag atggtgttta tgatgatctg   1860
ccattgcggc atttatctga tgatattagt cctgtgaaac atgctaagga aaccgccatt   1920
gctagattcg tcatgaggta ctttggcggg gaatttggtg ttaggctcgc ttttaatga    1980
```

<210> SEQ ID NO 85
<211> LENGTH: 658
<212> TYPE: PRT
<213> ORGANISM: Artificial Sequence
<220> FEATURE:
<223> OTHER INFORMATION: Amino acid sequence of fusion protein containing HGE-3 and HGE-1 antigens

<400> SEQUENCE: 85

```
Met Gln His His His His His Val Phe Tyr Ile Gly Leu Asp Tyr
 1               5                  10                  15

Ser Pro Ala Phe Ser Lys Ile Arg Asp Phe Ser Ile Arg Glu Ser Asn
                20                  25                  30

Gly Glu Thr Lys Ala Val Tyr Pro Tyr Leu Lys Asp Gly Lys Ser Val
            35                  40                  45

Lys Leu Glu Ser His Lys Phe Asp Trp Asn Thr Pro Asp Pro Arg Ile
    50                  55                  60

Gly Phe Lys Asp Asn Met Leu Val Ala Met Glu Gly Ser Val Gly Tyr
65                  70                  75                  80

Gly Ile Gly Gly Ala Arg Val Glu Leu Glu Ile Gly Tyr Glu Arg Phe
                85                  90                  95
```

```
Lys Thr Lys Gly Ile Arg Asp Ser Gly Ser Lys Glu Asp Glu Ala Asp
            100                 105                 110

Thr Val Tyr Leu Leu Ala Lys Glu Leu Ala Tyr Asp Val Val Thr Gly
        115                 120                 125

Gln Thr Asp Asn Leu Ala Ala Leu Ala Lys Thr Ser Gly Lys Asp
    130                 135                 140

Ile Val Gln Phe Ala Lys Ala Val Gly Val Ser His Pro Ser Ile Asp
145                 150                 155                 160

Gly Lys Val Cys Lys Thr Lys Ala Asp Ser Ser Lys Lys Phe Pro Leu
                165                 170                 175

Tyr Ser Asp Glu Thr His Thr Lys Gly Ala Asn Glu Gly Arg Thr Ser
            180                 185                 190

Leu Cys Gly Asp Asn Gly Ser Ser Thr Ile Thr Thr Ser Gly Thr Asn
        195                 200                 205

Val Ser Glu Thr Gly Gln Val Phe Arg Asp Phe Ile Arg Ala Thr Leu
        210                 215                 220

Lys Glu Asp Gly Ser Lys Asn Trp Pro Thr Ser Ser Gly Thr Gly Thr
225                 230                 235                 240

Pro Lys Pro Val Thr Asn Asp Asn Ala Lys Ala Val Ala Lys Asp Leu
                245                 250                 255

Val Gln Glu Leu Thr Pro Glu Glu Lys Thr Ile Val Ala Gly Leu Leu
            260                 265                 270

Ala Lys Thr Ile Glu Gly Gly Glu Val Val Glu Ile Arg Ala Val Ser
        275                 280                 285

Ser Thr Ser Val Met Val Asn Ala Cys Tyr Asp Leu Leu Ser Glu Gly
    290                 295                 300

Leu Gly Val Val Pro Tyr Ala Cys Val Gly Leu Gly Gly Asn Phe Val
305                 310                 315                 320

Gly Val Val Asp Gly Ile His Tyr Thr Asn His Leu Ser Glu Leu Glu
                325                 330                 335

Ile Gly Tyr Glu Arg Phe Lys Thr Lys Gly Ile Arg Asp Ser Gly Ser
            340                 345                 350

Lys Glu Asp Glu Ala Asp Thr Val Tyr Leu Leu Ala Lys Glu Leu Ala
        355                 360                 365

Tyr Asp Val Val Thr Gly Gln Thr Asp Asn Leu Ala Ala Leu Ala
    370                 375                 380

Lys Thr Ser Gly Lys Asp Ile Val Gln Phe Ala Lys Ala Val Glu Ile
385                 390                 395                 400

Ser His Ser Glu Ile Asp Gly Lys Val Cys Lys Thr Lys Ser Ala Gly
                405                 410                 415

Thr Gly Lys Asn Pro Cys Asp His Ser Gln Lys Pro Cys Ser Thr Asn
            420                 425                 430

Ala Tyr Tyr Ala Arg Arg Thr Gln Lys Ser Arg Ser Ser Gly Lys Thr
        435                 440                 445

Ser Leu Cys Gly Asp Ser Gly Tyr Ser Gly Gln Glu Leu Ile Thr Gly
    450                 455                 460

Gly His Tyr Ser Ser Pro Ser Val Phe Arg Asn Phe Val Lys Asp Thr
465                 470                 475                 480

Leu Gln Gly Asn Gly Ser Glu Asn Trp Pro Thr Ser Thr Gly Glu Gly
                485                 490                 495

Ser Glu Ser Asn Asp Asn Ala Ile Ala Val Ala Lys Asp Leu Val Asn
            500                 505                 510
```

-continued

```
Glu Leu Thr Pro Glu Glu Arg Thr Ile Val Ala Gly Leu Leu Ala Lys
        515                 520                 525

Ile Ile Glu Gly Ser Glu Val Ile Glu Ile Arg Ala Ile Ser Ser Thr
        530                 535                 540

Ser Val Thr Met Asn Ile Cys Ser Asp Ile Thr Ile Ser Asn Ile Leu
545                     550                 555                 560

Met Pro Tyr Val Cys Val Gly Pro Gly Met Ser Phe Val Ser Val Val
                565                 570                 575

Asp Gly His Thr Ala Ala Lys Phe Ala Tyr Arg Leu Lys Ala Gly Leu
            580                 585                 590

Ser Tyr Lys Phe Ser Lys Glu Val Thr Ala Phe Ala Gly Gly Phe Tyr
        595                 600                 605

His His Val Ile Gly Asp Gly Val Tyr Asp Asp Leu Pro Leu Arg His
        610                 615                 620

Leu Ser Asp Asp Ile Ser Pro Val Lys His Ala Lys Glu Thr Ala Ile
625                     630                 635                 640

Ala Arg Phe Val Met Arg Tyr Phe Gly Gly Glu Phe Gly Val Arg Leu
                645                 650                 655

Ala Phe
```

COMPOUNDS AND METHODS FOR THE DIAGNOSIS AND TREATMENT OF *EHRLICHIA* INFECTION

CROSS-REFERENCE TO RELATED APPLICATIONS

Figure 1:
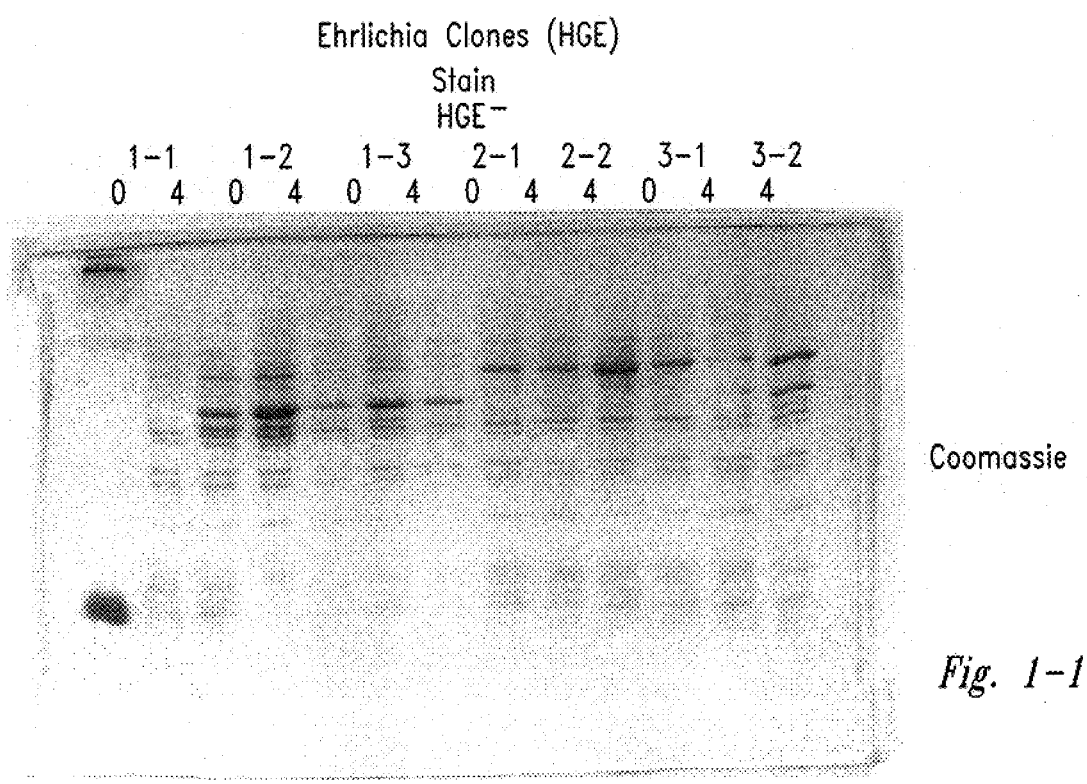
Figures 1, 2:
Figures 1, 2, 3:
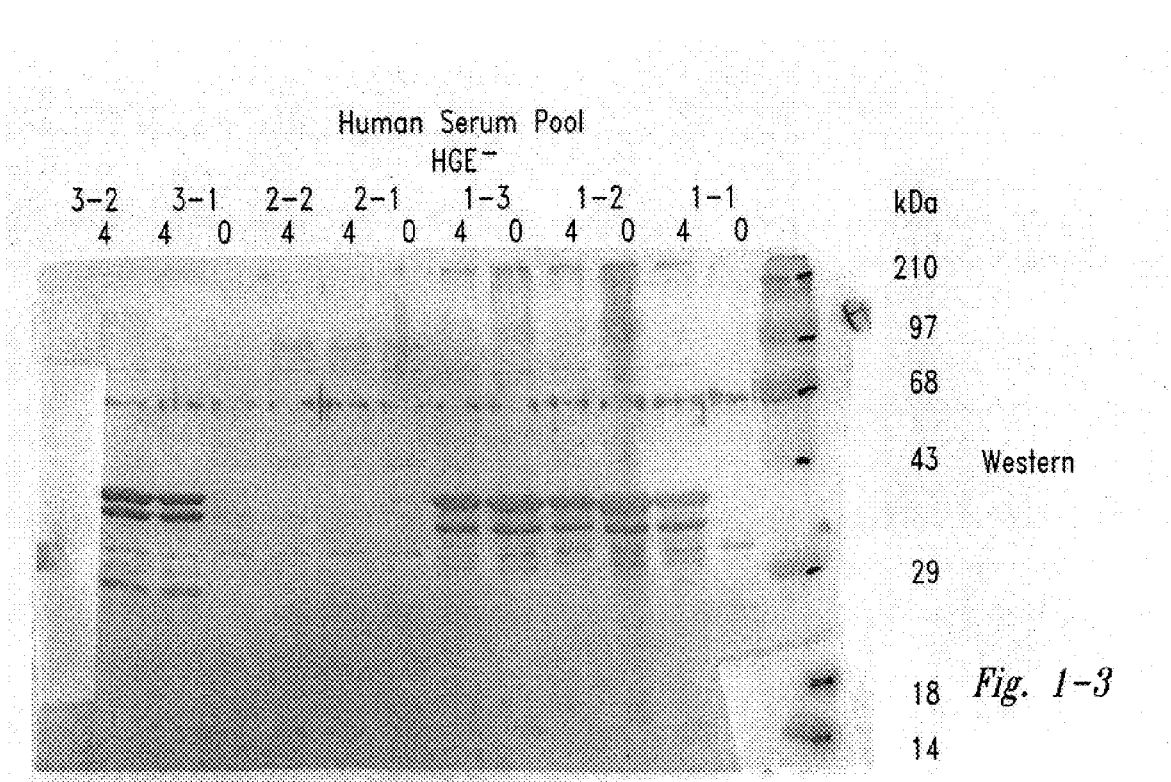

This application is a continuation in part of U.S. patent application Ser. No. 09/159,469, filed Sep. 23, 1998, which is a continuation in part of U.S. patent application Ser. No. 09/106,582, filed Jun. 29, 1998. which is a continuation-in-part of U.S. patent application Ser. No. 08/975,762, filed Nov. 20. 1997, which is a continuation-in-part of U.S. patent application Ser. No. 08/821,324, filed Mar. 21, 1997.

TECHNICAL FIELD

The present invention relates generally to the detection and treatment of Ehrlichia infection. In particular, the invention is related to polypeptides comprising an Ehrlichia antigen and the use of such polypeptide for the serodiagnosis and treatment of Human granulocytic ehrlichiosis (HGE).

BACKGROUND OF THE INVENTION

Human granulocytic ehrlichiosis (HGE) is an illness caused by a rodent bacterium which is generally transmitted to humans by the same tick that is responsible for the transmission of Lyme disease and babesiosis, thereby leading to the possibility of co-infection with Lyme disease, babesiosis and HGE from a single tick bite. The bacterium that causes HGE is believed to be quite widespread in parts of the northeastern United States and has been detected in parts of Europe. While the number of reported cases of HGE infection is increasing rapidly, infection with Ehrlichia, including co-infection with Lyme disease, often remains undetected for extended periods of time. HGE is a potentially fatal disease, with the risk of death increasing if appropriate treatment is delayed beyond the first few days after symptoms occur. In contrast, deaths from Lyme disease and babesiosis are relatively rare.

The preferred treatments for HGE, Lyme disease and babesiosis are different, with penicillins, such as doxycycline and amoxicillin, being most effective in treating Lyme disease, anti-malarial drugs being preferred for the treatment of babesiosis and tetracycline being preferred for the treatment of ehrlichiosis. Accurate and early diagnosis of Ehrlichia infection is thus critical but methods currently employed for diagnosis are problematic.

All three tick-borne illnesses share the same flu-like symptoms of muscle aches, fever, headaches and fatigue, thus making clinical diagnosis difficult. Microscopic analysis of blood samples may provide false-negative results when patients are first seen in the clinic. The only tests currently available for the diagnosis of HGE infection are indirect fluorescent antibody staining methods for total immunoglobulins to Ehrlichia causative agents and polymerase chain reaction (PCR) amplification tests. Such methods are time-consuming, labor-intensive and expensive. There thus remains a need in the art for improved methods for the detection of Ehrlichia infection, particularly as related to HGE. The present invention fulfills this need and further provides other related advantages.

SUMMARY OF THE INVENTION

The present invention provides compositions and methods for the diagnosis and treatment of Ehrlichia infection and, in particular, for the diagnosis and treatment of HGE.

In one aspect, polypeptides are provided comprising an immunogenic portion of an Ehrlichia antigen, particularly one associated with HGE or a variant of such an antigen that differs only in conservative substitutions and/or modifications. In one embodiment, the antigen comprises an amino acid sequence encoded by a DNA sequence selected from the group consisting of (a) sequences recited in SEQ ID NO: 1–3, 5, 7, 16, 20, 34, 39–49; (b) the complements of said sequences; and (c) sequences that hybridize to a sequence of (a) or (b) under moderately stringent conditions.

In another aspect, the present invention provides an antigenic epitope of an Ehrlichia antigen comprising an amino acid sequence selected from the group consisting of sequences recited in SEQ ID NO: 30 and 51, together with polypeptides comprising at least two such antigenic epitopes, the epitopes being contiguous.

In a related aspect, DNA sequences encoding the above polypeptides, recombinant expression vectors comprising one or more of these DNA sequences and host cells transformed or transfected with such expression vectors are also provided.

In another aspect, the present invention provides fusion proteins comprising either a first and a second inventive polypeptide, a first and a second inventive antigenic epitope, or, alternatively an inventive polypeptide and an inventive antigenic epitope. In one specific embodiment, a fusion protein comprising an amino acid sequence provided in SEQ ID NO: 85 is provided.

In further aspects of the subject invention, methods and diagnostic kits are provided for detecting Ehrlichia infection in a patient. In one embodiment, the method comprises: (a) contacting a biological sample with at least one of the above polypeptides, antigenic epitopes or fusion proteins; and (b) detecting in the sample the presence of antibodies that bind to the polypeptide, antigenic epitope or fusion protein, thereby detecting Ehrlichia infection in the biological sample. Suitable biological samples include whole blood, sputum, serum, plasma, saliva, cerebrospinal fluid and urine. The diagnostic kits comprise one or more of the above polypeptides, antigenic epitopes or fusion proteins in combination with a detection reagent.

The present invention also provides methods for detecting Ehrlichia infection comprising: (a) obtaining a biological sample from a patient; (b) contacting the sample with at least two oligonucleotide primers in a polymerase chain reaction, at least one of the oligonucleotide primers being specific for a DNA sequence encoding the above polypeptides; and (c) detecting in the sample a DNA sequence that amplifies in the presence of the oligonucleotide primers. In one embodiment, the oligonucleotide primer comprises at least about 10 contiguous nucleotides of a DNA sequence encoding the above polypeptides.

In a further aspect, the present invention provides a method for detecting Ehrlichia infection in a patient comprising: (a) obtaining a biological sample from the patient; (b) contacting the sample with an oligonucleotide probe specific for a DNA sequence encoding the above polypeptides; and (c) detecting in the sample a DNA sequence that hybridizes to the oligonucleotide probe. In one embodiment, the oligonucleotide probe comprises at least about 15 contiguous nucleotides of a DNA sequence encoding the above polypeptides.

In yet another aspect, the present invention provides antibodies, both polyclonal and monoclonal, that bind to the polypeptides described above, as well as methods for their use in the detection of Ehrlichia infection.

In further aspects, the present invention provides methods for detecting either Ehrlichia infection, Lyme disease or *B. microti* infection in a patient. Such inventive methods comprise (a) obtaining a biological sample from the patient; (b) contacting the sample with (i) at least one of the inventive polypeptides, antigenic epitopes or fusion proteins, (ii) a known Lyme disease antigen and (iii) a known *B. microti* antigen, and (b) detecting in the sample the presence of antibodies that bind to the inventive polypeptide, antigenic epitope or fusion protein the known Lyme disease antigen or the known *B. microti* antigen, thereby detecting either Ehrlichia infection, Lyme disease or *B. microti* infection in the patient.

Within other aspects, the present invention provides pharmaceutical compositions that comprise one or more of the above polypeptides or antigenic epitopes, or a DNA molecule encoding such polypeptides, and a physiologically acceptable carrier. The invention also provides vaccines comprising one or more of the inventive polypeptides or antigenic epitopes and a non-specific immune response enhancer, together with vaccines comprising one or more DNA sequences encoding such polypeptides and a non-specific immune response enhancer.

In yet another aspect, methods are provided for inducing protective immunity in a patient, comprising administering to a patient an effective amount of one or more of the above pharmaceutical compositions or vaccines.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS AND SEQUENCE IDENTIFIERS

FIG. 1 shows the results of Western blot analysis of representative Ehrlichia antigens of the present invention.

Figure 2A:
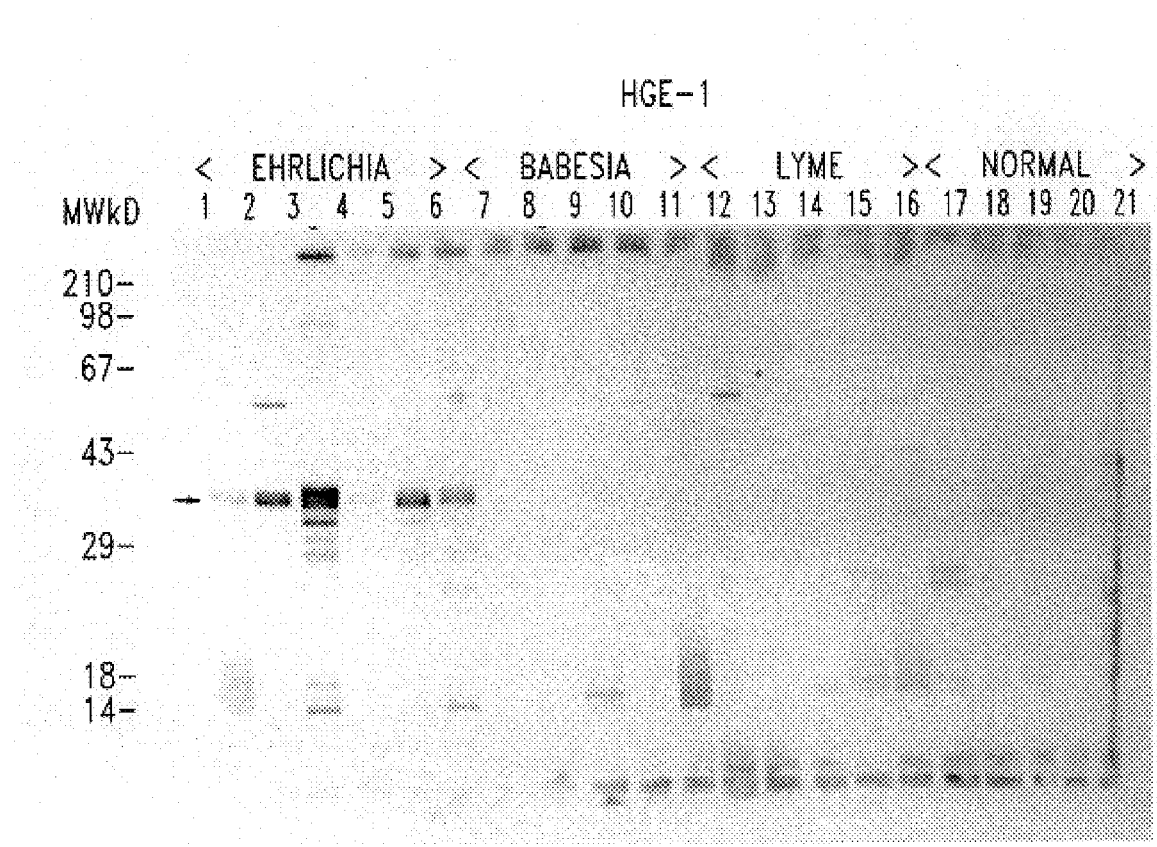

FIGS. 2A and B show the reactivity of purified recombinant Ehrlichia antigens HGE-1 and HGE-3, respectively, with sera from HGE-infected patients, abesiosis-infected patients, Lyme-disease infected patients and normal donors as determined by Western blot analysis.

SEQ ID NO: 1 is the determined DNA sequence of HGE-1.

SEQ ID NO: 2 is the determined DNA sequence of HGE-3.

SEQ ID NO: 3 is the determined DNA sequence of HGE-6.

SEQ ID NO: 4 is the determined 5' DNA sequence of HGE-7.

SEQ ID NO: 5 is the determined DNA sequence of HGE-12.

SEQ ID NO: 6 is the determined DNA sequence of HGF-23.

SEQ ID NO: 7 is the determined DNA sequence of HGE-24.

SEQ ID NO: 8 is the predicted protein sequence of HGE-1.

SEQ ID NO: 9 is the predicted protein sequence of HGE-3.

SEQ ID NO: 10 is the predicted protein sequence of HGE-6.

SEQ ID NO: 11 is the predicted protein sequence of HGE-7.

SEQ ID NO: 12 is the predicted protein sequence of HGE-12.

SEQ ID NO: 13 is the predicted protein sequence of HGE-23.

SEQ ID NO: 14 is the predicted protein sequence of HGE-24.

SEQ ID NO: 15 is the determined 5' DNA sequence of HGE-2.

SEQ ID NO: 16 is the determined DNA sequence of HGE-9.

SEQ ID NO: 17 is the determined DNA sequence of HGE-14.

SEQ ID NO: 18 is the determined 5' DNA sequence of HGE-15.

SEQ ID NO: 19 is the determined 5' DNA sequence of HGE-16.

SEQ ID NO: 20 is the determined 5' DNA sequence of HGE- 17.

SEQ ID NO: 21 is the determined 5' DNA sequence of HGE-18.

SEQ ID NO: 22 is the determined 5' DNA sequence of HGE-25.

SEQ ID NO: 23 is the predicted protein sequence of HGE-2.

SEQ ID NO: 24 is the predicted protein sequence of HGE-9.

SEQ ID NO: 25 is the predicted protein sequence of HGE-14.

SEQ ID NO: 26 is the predicted protein sequence of HGE-18.

SEQ ID NO: 27 is the predicted protein sequence from the reverse complement of HGE-14.

SEQ ID NO: 28 is the predicted protein sequence from the reverse complement of HGE- 15.

SEQ ID NO: 29 is the predicted protein sequence from the reverse complement of HGE-18.

SEQ ID NO: 30 is a 41 amino acid repeat sequence from HGE-14.

SEQ ID NO: 31 is the determined DNA sequence of HGE-11.

SEQ ID NO: 32 is the predicted protein sequence of HGE-11.

SEQ ID NO: 33 is the predicted protein sequence from the reverse complement of HGE- 11.

SEQ ID NO: 34 is the determined DNA sequence of HGE-13.

SEQ ID NO: 35 is the predicted protein sequence of HGE-13.

SEQ ID NO: 36 is the determined DNA sequence of HGE-8.

SEQ ID NO: 37 is the predicted protein sequence of HGE-8.

SEQ ID NO: 38 is the predicted protein sequence from the reverse complement of HGE-8.

SEQ ID NO: 39 is the extended DNA sequence of HGE-2.

SEQ ID NO: 40 is the extended DNA sequence of HGE-7.

SEQ ID NO: 41 is the extended DNA sequence of HGE-8.

SEQ ID NO: 42 is the extended DNA sequence of HGE-11.

SEQ ID NO: 43 is the extended DNA sequence of HGE-14.

SEQ ID NO: 44 is the extended DNA sequence of HGE-15.

SEQ ID NO: 45 is the extended DNA sequence of HGE-16.

SEQ ID NO: 46 is the extended DNA sequence of HGE-18.

SEQ ID NO: 47 is the extended DNA sequence of HGE-23.

SEQ ID NO: 48 is the extended DNA sequence of HGE-25.

SEQ ID NO: 49 is the determined 3' DNA sequence of HGE-17.

SEQ ID NO: 50 is the extended predicted protein sequence of HGE-2.

SEQ ID NO: 51 is the amino acid repeat sequence of HGE-2.

SEQ ID NO: 52 is a second predicted protein sequence of HGE-7.

SEQ ID NO: 53 is a third predicted protein sequence of HGE-7.

SEQ ID NO: 54 is a second predicted protein sequence of HGE-8.

SEQ ID NO: 55 is a third predicted protein sequence of HGE-8.

SEQ ID NO: 56 is a fourth predicted protein sequence of HGE-8.

SEQ ID NO: 57 is a fifth predicted protein sequence of HGE-8.

SEQ ID NO: 58 is a second predicted protein sequence of HGE-11.

SEQ ID NO: 59 is a third predicted protein sequence of HGE-11.

SEQ ID NO: 60 is a second predicted protein sequence from the reverse complement of HGE- 14.

SEQ ID NO: 61 is a third predicted protein sequence from the reverse complement of HGE- 14.

SEQ ID NO: 62 is a first predicted protein sequence of HGE-15.

SEQ ID NO: 63 is a second predicted protein sequence of HGE-15.

SEQ ID NO: 64 is a second predicted protein sequence from the reverse complement of HGE- 15.

SEQ ID NO: 65 is the predicted protein sequence of HGE-16.

SEQ ID NO: 66 is a first predicted protein sequence from the reverse complement of HGE-17.

SEQ ID NO: 67 is a second predicted protein sequence from the reverse complement of HGE-17.

SEQ ID NO: 68 is a second predicted protein sequence from the reverse complement of HGE-18.

SEQ ID NO: 69 is a third predicted protein sequence from the reverse complement of HGE-18.

SEQ ID NO: 70 is a fourth predicted protein sequence from the reverse complement of HGE-18.

SEQ ID NO: 71 is a second predicted protein sequence of LIGE-23.

SEQ ID NO: 72 is a third predicted protein sequence of HGE-23.

SEQ ID NO: 73 is the predicted protein sequence of HGE-25.

SEQ ID NO: 74–79 are primers used in the preparation of a fusion protein containing HGE-9, HGE-3 and HGE-1.

SEQ ID NO: 80–83 are primers used in the preparation of a fusion protein containing HGE-3 and HGE-1 (referred to as ErF-1).

SEQ ID NO: 84 is the DNA sequence of the fusion ErF-1.

SEQ ID NO: 85 is the amino acid sequence of the fusion protein ErF-1.

DETAILED DESCRIPTION OF THE INVENTION

As noted above, the present invention is generally directed to compositions and methods for the diagnosis and treatment of Ehrlichia infection, in particular HGE. In one aspect, the compositions of the subject invention include polypeptides that comprise at least one immunogenic portion of an Ehrlichia antigen, or a variant of such an antigen that differs only in conservative substitutions and/or modifications.

As used herein, the term "polypeptide" encompasses amino acid chains of any length, including full length proteins (i.e., antigens), wherein the amino acid residues are linked by covalent peptide bonds. Thus, a polypeptide comprising an immunogenic portion of one of the above antigens may consist entirely of the immunogenic portion, or may contain additional sequences. The additional sequences may be derived from the native Ehrlichia antigen or may be heterologous, and such sequences may (but need not) be immunogenic.

An "immunogenic portion" of an antigen is a portion that is capable of reacting with sera obtained from an Ehrlichia-infected individual (i.e., generates an absorbance reading with sera from infected individuals that is at least three standard deviations above the absorbance obtained with sera from uninfected individuals, in a representative ELISA assay described herein). Such immunogenic portions generally comprise at least about 5 amino acid residues, more preferably at least about 10, and most preferably at least about 20 amino acid residues. Methods for preparing and identifying immunogenic portions of antigens of known sequence are well known in the art and include those summarized in Paul, *Fundamental Immunology*, 3$^{rd}$ ed., Raven Press, 1993, pp. 243–247. Polypeptides comprising at least an immunogenic portion of one or more Ehrlichia antigens as described herein may generally be used, alone or in combination, to detect HGE in a patient.

The compositions and methods of the present invention also encompass variants of the above polypeptides and DNA molecules. Such variants include, but are not limited to, naturally occurring allelic variants of the inventive sequences.

A polypeptide "variant," as used herein, is a polypeptide that differs from the recited polypeptide only in conservative substitutions and/or modifications, such that the antigenic properties of the polypeptide are retained. In a preferred embodiment, variant polypeptides differ from an identified sequence by substitution, deletion or addition of five amino acids or fewer. Such variants may generally be identified by modifying one of the above polypeptide sequences, and evaluating the antigenic properties of the modified polypeptide using, for example, the representative procedures described herein. Polypeptide variants preferably exhibit at least about 70%, more preferably at least about 90% and most preferably at least about 95% identity (determined as described below) to the identified polypeptides.

As used herein, a "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gin, asn, ser, thr; (2) cys, ser, tyr, thr; (3) val, ile, leu, met, ala, phe; (4) lys, arg, his; and (5) phe, tyr, trp, his.

Variants may also, or alternatively, contain other modifications, including the deletion or addition of amino acids that have minimal influence on the antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

A nucleotide "variant" is a sequence that differs from the recited nucleotide sequence in having one or more nucleotide deletions, substitutions or additions. Such modifications may be readily introduced using standard mutagenesis techniques, such as oligonucleotide-directed site-specific mutagenesis as taught, for example, by Adelman et al. (*DNA*, 2:183, 1983). Nucleotide variants may be naturally occurring allelic variants, or non-naturally occurring variants. Variant nucleotide sequences preferably exhibit at least about 70%, more preferably at least about 80% and most preferably at least about 90% identity (determined as described below) to the recited sequence.

Two nucleotide or polypeptide sequences are said to be "identical" if the sequence of nucleotides or amino acid residues in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Resarch Foundaiton, Washington D.C. Vol. 5, Suppl. 3, pp. 345–358; Hein J. (1990) Unified Approach to Alignment and Phylogenes pp. 626–645*Methods in Enzymology* vol. 183, Academic Press, Inc., San Diego, Calif.; Higgins, D. G. and Sharp, P. M. (1989) Fast and sensitive multiple sequence alignments on a microcomputer *CABIOS* 5:151–153; Myers, E. W. and Muller W. (1988) Optimal alignments in linear space *CABIOS* 4:11–17; Robinson, E. D. (1971) *Comb. Theor* 11:1 05; Santou, N. Nes, M. (1987) The neighbor joining method. A new method for reconstructing phylogenetic trees *Mol. Biol. Evol.* 4:406–425; Sneath, P. H. A. and Sokal, R. R. (1973) *Numerical Taxonomy—the Principles and Practice of Numerical Taxonomy*, Freeman Press, San Francisco, Calif.; Wilbur, W. J. and lipman, D. J. (1983) Rapid similarity searches of nucleic acid and protein data banks *Proc. Natl. Acad, Sci. USA* 80:726–730.

Preferably, the "percentage of sequence identity" is determined by comparing two optimally aligned sequences over a window of comparison of at least 20 positions, wherein the portion of the polynucleotide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

In specific embodiments, the subject invention discloses polypeptides comprising at least an immunogenic portion of an Ehrlichia antigen (or a variant of such an antigen), that comprises one or more of the amino acid sequences encoded by (a) a DNA sequence selected from the group consisting of SEQ ID NO: 1–3, 5, 7, 16, 20, 34. 39–49, (b) the complements of such DNA sequences or (c) DNA sequences substantially homologous to a sequence in (a) or (b).

The Ehrlichia antigens provided by the present invention include variants that are encoded by DNA sequences which are substantially homologous to one or more of the DNA sequences specifically recited herein. "Substantial homology," as used herein, refers to DNA sequences that are capable of hybridizing under moderately stringent conditions. Suitable moderately stringent conditions include prewashing in a solution of 5×SSC, 0.5% SDS. 1.0 mM EDTA (pH 8.0); hybridizing at 50° C.–65° C., 5×SSC, overnight or, in the event of cross-species homology, at 45° C. with 0.5×SSC; followed by washing twice at 65° C. for 20 minutes with each of 2×, 0.5× and 0.2×SSC containing 0.1% SDS. Such hybridizing DNA sequences are also within the scope of this invention, as are nucleotide sequences that, due to code degeneracy, encode an immunogenic polypeptide that is encoded by a hybridizing DNA sequence.

In general, Ehrlichia antigens, and DNA sequences encoding such antigens, may be prepared using any of a variety of procedures. For example, DNA molecules encoding Ehrlichia antigens may be isolated from an Ehrlichia genomic or cDNA expression library by screening with sera from HGE-infected individuals as described below in Example 1, and sequenced using techniques well known to those of skill in the art. DNA molecules encoding Ehrlichia antigens may also be isolated by screening an appropriate Ehrlichia expression library with anti-sera (e.g., rabbit) raised specifically against Ehrlichia antigens.

Antigens may be induced from such clones and evaluated for a desired property, such as the ability to react with sera obtained from an HGE-infected individual as described herein. Alternatively, antigens may be produced recombinantly, as described below, by inserting a DNA sequence that encodes the antigen into an expression vector and expressing the antigen in an appropriate host. Antigens may be partially sequenced using, for example, traditional Edman chemistry. See Edman and Berg, *Eur. J Biochem.* 80:116–132, 1967.

DNA sequences encoding antigens may also be obtained by screening an appropriate Ehrlichia cDNA or genomic DNA library for DNA sequences that hybridize to degenerate oligonucleotides derived from partial amino acid sequences of isolated antigens. Degenerate oligonucleotide sequences for use in such a screen may be designed and synthesized, and the screen may be performed, as described (for example) in Sambrook et al., *Molecular Cloning: A Laboratory Manual*, Cold Spring Harbor Laboratories, Cold Spring Harbor, N.Y. (and references cited therein). Polymerase chain reaction (PCR) may also be employed, using the above oligonucleotides in methods well known in the art, to isolate a nucleic acid probe from a cDNA or genomic library. The library screen may then be performed using the isolated probe.

Synthetic polypeptides having fewer than about 100 amino acids, and generally fewer than about 50 amino acids, may be generated using techniques well known in the art. For example, such polypeptides may be synthesized using any of the commercially available solid-phase techniques, such as the Merrifield solid-phase synthesis method, where amino acids are sequentially added to a growing amino acid chain. See Merrifield, *J Am. Chem. Soc.* 85:2149–2146, 1963. Equipment for automated synthesis of polypeptides is commercially available from suppliers such as Perkin Elmer/Applied BioSystems Division, Foster City, Calif., and may be operated according to the manufacturer's instructions.

Immunogenic portions of Ehrlichia antigens may be prepared and identified using well known techniques, such as those summarized in Paul, *Fundamental Immunology*, 3d ed., Raven Press, 1993, pp. 243–247 and references cited therein. Such techniques include screening polypeptide portions of the native antigen for immunogenic properties. The representative ELISAs described herein may generally be employed in these screens. An immunogenic portion of a polypeptide is a portion that, within such representative assays, generates a signal in such assays that is substantially similar to that generated by the full length antigen. In other words, an immunogenic portion of an Ehrlichia antigen generates at least about 20%, and preferably about 100%, of the signal induced by the full length antigen in a model ELISA as described herein.

Portions and other variants of Ehrlichia antigens may be generated by synthetic or recombinant means. Variants of a native antigen may generally be prepared using standard mutagenesis techniques, such as oligonucleotide-directed site-specific mutagenesis. Sections of the DNA sequence may also be removed using standard techniques to permit preparation of truncated polypeptides.

Recombinant polypeptides containing portions and/or variants of a native antigen may be readily prepared from a DNA sequence encoding the polypeptide using a variety of techniques well known to those of ordinary skill in the art. For example, supernatants from suitable host/vector systems which secrete recombinant protein into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant protein.

Any of a variety of expression vectors known to those of ordinary skill in the art may be employed to express recombinant polypeptides as described herein. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, yeast or a mammalian cell line, such as COS or CHO. The DNA sequences expressed in this manner may encode naturally occurring antigens, portions of naturally occurring antigens, or other variants thereof.

In another aspect, the present invention provides antigenic epitopes of an Ehrlichia antigen or epitope repeat sequences, as well as polypeptides comprising at least two such contiguous antigenic epitopes. As used herein, an "epitope" is a portion of an antigen that reacts with sera from Ehrlichia-infected individuals (i.e. an epitope is specifically bound by one or more antibodies present in such sera). As discussed above, epitopes of the antigens described in the present application may be generally identified using techniques well known to those of skill in the art.

In specific embodiments, antigenic epitopes of the present invention comprise an amino acid sequence selected from the group consisting of sequence recited in SEQ ID NO: 30 and 51. As discussed in more detail below, antigenic epitopes provided herein may be employed in the diagnosis and treatment of Ehrlichia infection, either alone or in combination with other Ehrlichia antigens or antigenic epitopes. Antigenic epitopes and polypeptides comprising such epitopes may be prepared by synthetic means, as described generally above and in detail in Example 3.

In general, regardless of the method of preparation, the polypeptides and antigenic epitopes disclosed herein are prepared in an isolated, substantially pure, form. Preferably, the polypeptides and antigenic epitopes are at least about 80% pure, more preferably at least about 90% pure and most preferably at least about 99% pure.

In a further aspect, the present invention provides fusion proteins comprising either a first and a second inventive polypeptide. a first and a second inventive antigenic epitope, or an inventive polypeptide and an antigenic epitope of the present invention, together with variants of such fusion proteins. The fusion proteins of the present invention may also include a linker peptide between the polypeptides or antigenic epitopes.

A DNA sequence encoding a fusion protein of the present invention may be constructed using known recombinant DNA techniques to assemble separate DNA sequences encoding, for example, the first and second polypeptides, into an appropriate expression vector. The 3' end of a DNA sequence encoding the first polypeptide is ligated, with or without a peptide linker, to the 5' end of a DNA sequence encoding the second polypeptide so that the reading frames of the sequences are in phase to permit mRNA translation of the two DNA sequences into a single fusion protein that retains the biological activity of both the first and the second polypeptides.

A peptide linker sequence may be employed to separate the first and the second polypeptides by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., Gene 40:39–46, 1985; Murphy et al., *Proc.*

*Natl. Acad. Sci. USA* 83:8258–8562, 1986; U.S. Pat. No. 4,935,233 and U.S. Pat. No. 4,751,180. The linker sequence may be from 1 to about 50 amino acids in length. As an alternative to the use of a peptide linker sequence (when desired), one can utilize non-essential N-terminal amino acid regions (when present) on the first and second polypeptides to separate the functional domains and prevent steric hindrance.

In another aspect, the present invention provides methods for using the polypeptides, fusion proteins and antigenic epitopes described above to diagnose Ehrlichia infection, in particular HGE. In this aspect, methods are provided for detecting Ehrlichia infection in a biological sample, using one or more of the above polypeptides, fusion proteins and antigenic epitopes, either alone or in combination. For clarity, the term "polypeptide" will be used when describing specific embodiments of the inventive diagnostic methods. However, it will be clear to one of skill in the art that the antigenic epitopes and fusion proteins of the present invention may also be employed in such methods.

As used herein, a "biological sample" is any antibody-containing sample obtained from a patient. Preferably, the sample is whole blood, sputum, serum, plasma, saliva, cerebrospinal fluid or urine. More preferably, the sample is a blood, serum or plasma sample obtained from a patient. The polypeptides are used in an assay, as described below, to determine the presence or absence of antibodies to the polypeptide(s) in the sample, relative to a predetermined cut-off value. The presence of such antibodies indicates previous sensitization to Ehrlichia antigens which may be indicative of HGE.

In embodiments in which more than one polypeptide is employed, the polypeptides used are preferably complementary (i.e., one component polypeptide will tend to detect infection in samples where the infection would not be detected by another component polypeptide). Complementary polypeptides may generally be identified by using each polypeptide individually to evaluate serum samples obtained from a series of patients known to be infected with HGE. After determining which samples test positive (as described below) with each polypeptide, combinations of two or more polypeptides may be formulated that are capable of detecting infection in most, or all, of the samples tested.

A variety of assay formats are known to those of ordinary skill in the art for using one or more polypeptides to detect antibodies in a sample. See, e.g., Harlow and Lane, *Antibodies: A Laboratory Manual*, Cold Spring Harbor Laboratory, 1988, which is incorporated herein by reference. In a preferred embodiment, the assay involves the use of polypeptide immobilized on a solid support to bind to and remove the antibody from the sample. The bound antibody may then be detected using a detection reagent that contains a reporter group. Suitable detection reagents include antibodies that bind to the antibody/polypeptide complex and free polypeptide labeled with a reporter group (e.g., in a semi-competitive assay). Alternatively, a competitive assay may be utilized, in which an antibody that binds to the polypeptide is labeled with a reporter group and allowed to bind to the immobilized antigen after incubation of the antigen with the sample. The extent to which components of the sample inhibit the binding of the labeled antibody to the polypeptide is indicative of the reactivity of the sample with the immobilized polypeptide.

The solid support may be any solid material known to those of ordinary skill in the art to which the antigen may be attached. For example, the solid support may be a test well in a microtiter plate, or a nitrocellulose or other suitable membrane. Alternatively, the support may be a bead or disc, such as glass. fiberglass, latex or a plastic material such as polystyrene or polyvinylchloride. The support may also be a magnetic particle or a fiber optic sensor, such as those disclosed, for example, in U.S. Pat. No. 5,359,681.

The polypeptides may be bound to the solid support using a variety of techniques known to those of ordinary skill in the art. In the context of the present invention, the term "bound" refers to both noncovalent association, such as adsorption, and covalent attachment (which may be a direct linkage between the antigen and functional groups on the support or may be a linkage by way of a cross-linking agent). Binding by adsorption to a well in a microtiter plate or to a membrane is preferred. In such cases, adsorption may be achieved by contacting the polypeptide, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of polypeptide ranging from about 10 ng to about 1 $\mu$g. and preferably about 100 ng, is sufficient to bind an adequate amount of antigen.

Covalent attachment of polypeptide to a solid support may generally be achieved by first reacting the support with a bifunctional reagent that will react with both the support and a functional group, such as a hydroxyl or amino group, on the polypeptide. For example, the polypeptide may be bound to supports having an appropriate polymer coating using benzoquinone or by condensation of an aldehyde group on the support with an amine and an active hydrogen on the polypeptide (see, e.g., Pierce Immunotechnology Catalog and Handbook, 1991, at A12–A13).

In certain embodiments, the assay is an enzyme linked immunosorbent assay (ELISA). This assay may be performed by first contacting a polypeptide antigen that has been immobilized on a solid support, commonly the well of a microtiter plate, with the sample, such that antibodies to the polypeptide within the sample are allowed to bind to the immobilized polypeptide. Unbound sample is then removed from the immobilized polypeptide and a detection reagent capable of binding to the immobilized antibody-polypeptide complex is added. The amount of detection reagent that remains bound to the solid support is then determined using a method appropriate for the specific detection reagent.

More specifically, once the polypeptide is immobilized on the support as described above, the remaining protein binding sites on the support are typically blocked. Any suitable blocking agent known to those of ordinary skill in the art, such as bovine serum albumin (BSA) or Tween 20™ (Sigma Chemical Co., St. Louis. Mo.) may be employed. The immobilized polypeptide is then incubated with the sample, and antibody is allowed to bind to the antigen. The sample may be diluted with a suitable dilutent, such as phosphate-buffered saline (PBS) prior to incubation. In general, an appropriate contact time (i.e., incubation time) is that period of time that is sufficient to detect the presence of antibody within an HGE-infected sample. Preferably, the contact time is sufficient to achieve a level of binding that is at least 95% of that achieved at equilibrium between bound and unbound antibody. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. Detection reagent may then be added to the solid support. An appropriate detection reagent is any compound that binds to the immobilized antibody-polypeptide complex and that can be detected by any of a variety of means known to those in the art. Preferably, the detection reagent contains a binding agent (such as, for example, Protein A. Protein G, immunoglobulin, lectin or free antigen) conjugated to a reporter group. Preferred reporter groups include enzymes (such as horseradish peroxidase), substrates, cofactors, inhibitors, dyes, radionuclides, luminescent groups, fluorescent groups and biotin. The conjugation of binding agent to reporter group may be achieved using standard methods known to those of ordinary skill in the art. Common binding agents may also be purchased conjugated to a variety of reporter groups from many commercial sources (e.g., Zymed Laboratories, San Francisco, Calif., and Pierce, Rockford, Ill.).

The detection reagent is then incubated with the immobilized antibody-polypeptide complex for an amount of time sufficient to detect the bound antibody. An appropriate amount of time may generally be determined from the manufacturer's instructions or by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of anti-Ehrlichia antibodies in the sample, the signal detected from the reporter group that remains bound to the solid support is generally compared to a signal that corresponds to a predetermined cut-off value. In one preferred embodiment, the cut-off value is the average mean signal obtained when the immobilized antigen is incubated with samples from an uninfected patient. In general, a sample generating a signal that is three standard deviations above the predetermined cut-off value is considered positive for HGE. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, pp. 106–107. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for HGE.

In a related embodiment, the assay is performed in a rapid flow-through or strip test format, wherein the antigen is immobilized on a membrane, such as nitrocellulose. In the flow-through test, antibodies within the sample bind to the immobilized polypeptide as the sample passes through the membrane. A detection reagent (e.g., protein A-colloidal gold) then binds to the antibody-polypeptide complex as the solution containing the detection reagent flows through the membrane. The detection of bound detection reagent may then be performed as described above. In the strip test format, one end of the membrane to which polypeptide is bound is immersed in a solution containing the sample. The sample migrates along the membrane through a region containing detection reagent and to the area of immobilized polypeptide. Concentration of detection reagent at the polypeptide indicates the presence of anti-Ehrlichia antibodies in the sample. Typically, the concentration of detection reagent at that site generates a pattern, such as a line, that can be read visually. The absence of such a pattern indicates a negative result. In general, the amount of polypeptide immobilized on the membrane is selected to generate a visually discernible pattern when the biological sample contains a level of antibodies that would be sufficient to generate a positive signal in an ELISA, as discussed above. Preferably, the amount of polypeptide immobilized on the membrane ranges from about 25 ng to about 1 $\mu$g, and more preferably from about 50 ng to about 500 ng. Such tests can typically be performed with a very small amount (e.g., one drop) of patient serum or blood.

Of course, numerous other assay protocols exist that are suitable for use with the polypeptides and antigenic epitopes of the present invention. The above descriptions are intended to be exemplary only.

The inventive polypeptides may be employed in combination with known Lyme disease and/or *B. microti* antigens to diagnose the presence of either Ehrlichia infection, Lyme disease and/or *B. microti* infection, using either the assay formats described herein or other assay protocols. One example of an alternative assay protocol which may be usefully employed in such methods is a Western blot, wherein the proteins present in a biological sample are separated on a gel, prior to exposure to a binding agent. Such techniques are well known to those of skill in the art. Lyme disease antigens which may be usefully employed in such methods are well known to those of skill in the art and include, for example, those described by Magnarelli. L. et al. (J. Clin. Microbiol., 1996 34:237–240), Magnarelli, L,. (Rheum. Dis. Clin. North Am., 1989, 15:735–745) and Cutler, S. J. (J. Clin. Pathol., 1989, 42:869–871). *B. microti* antigens which may be usefully employed in the inventive methods include those described in U.S. patent application Ser. No. 08/845,258, filed Apr. 24, 1997, the disclosure of which is hereby incorporated by reference.

In yet another aspect, the present invention provides antibodies to the polypeptides and antigenic epitopes of the present invention. Antibodies may be prepared by any of a variety of techniques known to those of ordinary skill in the art. See, e.g., Harlow and Lane, *Antibodies. A Laboratory Manual*, Cold Spring Harbor Laboratory, Cold Spring Harbor, N.Y., 1988. In one such technique, an immunogen comprising the antigenic polypeptide or epitope is initially injected into any of a wide variety of mammals (e.g., mice, rats, rabbits, sheep and goats). The polypeptides and antigenic epitopes of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide or antigenic epitope may then be purified from such antisera by, for example, affinity chromatography using the polypeptide coupled to a suitable solid support.

Monoclonal antibodies specific for the antigenic polypeptide or epitope of interest may be prepared, for example, using the technique of Kohler and Milstein, Eur. *J Immunol.* 6:511–519, 1976, and improvements thereto. Briefly, these methods involve the preparation of immortal cell lines capable of producing antibodies having the desired specificity (i.e., reactivity with the polypeptide or antigenic epitope of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide or antigenic epitope. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides or antigenic epitopes of this invention may be used in the purification process in, for example, an affinity chromatography step.

Antibodies may be used in diagnostic tests to detect the presence of Ehrlichia antigens using assays similar to those detailed above and other techniques well known to those of skill in the art, thereby providing a method for detecting Ehrlichia infection in a patient.

Diagnostic reagents of the present invention may also comprise DNA sequences encoding one or more of the above polypeptides, or one or more portions thereof. For example, at least two oligonucleotide primers may be employed in a polymerase chain reaction (PCR) based assay to amplify Ehrlichia-specific cDNA derived from a biological sample, wherein at least one of the oligonucleotide primers is specific for a DNA molecule encoding a polypeptide of the present invention. The presence of the amplified cDNA is then detected using techniques well known in the art, such as gel electrophoresis. Similarly, oligonucleotide probes specific for a DNA molecule encoding a polypeptide of the present invention may be used in a hybridization assay to detect the presence of an inventive polypeptide in a biological sample.

As used herein, the term "oligonucleotide primer/probe specific for a DNA molecule" means an oligonucleotide sequence that has at least about 80%, preferably at least about 90% and more preferably at least about 95%, identity to the DNA molecule in question. Oligonucleotide primers and/or probes which may be usefully employed in the inventive diagnostic methods preferably have at least about 10–40 nucleotides. In a preferred embodiment, the oligonucleotide primers comprise at least about 10 contiguous nucleotides of a DNA molecule encoding one of the polypeptides disclosed herein. Preferably, oligonucleotide probes for use in the inventive diagnostic methods comprise at least about 15 contiguous oligonucleotides of a DNA molecule encoding one of the polypeptides disclosed herein. Techniques for both PCR based assays and hybridization assays are well known in the art (see, for example, Mullis el al. Ibid; Ehrlich, Ibid). Primers or probes may thus be used to detect Ehrlichia-specific sequences in biological samples. DNA probes or primers comprising oligonucleotide sequences described above may be used alone or in combination with each other.

In another aspect, the present invention provides methods for using one or more of the above polypeptides, antigenic epitopes or fusion proteins (or DNA molecules encoding such polypeptides) to induce protective immunity against Ehrlichia infection in a patient. As used herein, a "patient" refers to any warm-blooded animal, preferably a human. A patient may be afflicted with a disease, or may be free of detectable disease and/or infection. In other words, protective immunity may be induced to prevent or treat Ehrlichia infection, specifically HGE.

In this aspect, the polypeptide, antigenic epitope, fusion protein or DNA molecule is generally present within a pharmaceutical composition or a vaccine. Pharmaceutical compositions may comprise one or more polypeptides, each of which may contain one or more of the above sequences (or variants thereof), and a physiologically acceptable carrier. Vaccines may comprise one or more of the above polypeptides and a non-specific immune response enhancer, such as an adjuvant or a liposome (into which the polypeptide is incorporated). Such pharmaceutical compositions and vaccines may also contain other Ehrlichia antigens, either incorporated into a combination polypeptide or present within a separate polypeptide.

Alternatively, a vaccine may contain DNA encoding one or more polypeptides, antigenic epitopes or fusion proteins as described above, such that the polypeptide is generated in situ. In such vaccines, the DNA may be present within any of a variety of delivery systems known to those of ordinary skill in the art, including nucleic acid expression systems, bacterial and viral expression systems. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface. In a preferred embodiment, the DNA may be introduced using a viral expression system (e.g., vaccinia or other pox virus, retrovirus, or adenovirus), which may involve the use of a non-pathogenic (defective), virus. Techniques for incorporating DNA into such expression systems are well known to those of ordinary skill in the art. The DNA may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells.

In a related aspect, a DNA vaccine as described above may be administered simultaneously with or sequentially to either a polypeptide of the present invention or a known Ehrlichia antigen. For example, administration of DNA encoding a polypeptide of the present invention, either "naked" or in a delivery system as described above, may be followed by administration of an antigen in order to enhance the protective immune effect of the vaccine.

Routes and frequency of administration, as well as dosage, will vary from individual to individual. In general, the pharmaceutical compositions and vaccines may be administered by injection (e.g., intracutaneous, intramuscular, intravenous or subcutaneous), intranasally (e.g. by aspiration) or orally. Between 1 and 3 doses may be administered for a 1–36 week period. Preferably, 3 doses are administered, at intervals of 3–4 months, and booster vaccinations mav be given periodically thereafter. Alternate protocols may be appropriate for individual patients. A suitable dose is an amount of polypeptide or DNA that, when administered as described above, is capable of raising an immune response in an immunized patient sufficient to protect the patient from HGE for at least 1–2 years. In general, the amount of polypeptide present in a dose (or produced in situ by the DNA in a dose) ranges from about 1 pg to about 100 mg per kg of host, typically from about 10 pg to about 1 mg, and preferably from about 100 pg to about 1 µg. Suitable dose sizes will vary with the size of the patient, but will typically range from about 0.1 mL to about 5 mL.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos 4,897,268 and 5,075,109.

Any of a variety of adjuvants may be employed in the vaccines of this invention to nonspecifically enhance the immune response. Most adjuvants contain a substance designed to protect the antigen from rapid catabolism, such as aluminum hydroxide or mineral oil, and a nonspecific stimulator of immune responses, such as lipid A, *Bortadella pertussis* or *Mycobaclerium tuberculosis*. Suitable adjuvants ate commercially available as, for example, Freund's Incomplete Adjuvant and Freund's Complete Adjuvant (Difco Laboratories. Detroit. Mich.) and Merck Adjuvant 65 (Merck and Company, Inc., Rahway, N.J.). Other suitable adjuvants include alum, biodegradable microspheres, moriophosphoryl lipid A and quil A.

The following Examples are offered by way of illustration and not by way of limitation.

EXAMPLE 1

ISOLATION OF DNA SEQUENCES ENCODING EHRLICHIA ANTIGENS

This example illustrates the preparation of DNA sequences encoding Ehrlichia antigens by screening an Ehrlichia genomic expression library with sera obtained from mice infected with the HGE agent.

Ehrlichia genomic DNA was isolated from infected human HL60 cells and sheared by sonication. The resulting randomly sheared DNA was used to construct an Ehrlichia genomic expression library (approximately 0.5–4.0 kbp inserts) with FcoRI adaptors and a Lambda ZAP Il/EcoRI/CIAP vector (Stratagene, La Jolla. Calif.). The unamplified library ($6.5\times10^6$/ml) was screened with an *E. coli* lysate-absorbed Ehrlichia mouse serum pool, as described in Sambrook et al., *Molecular Cloning. A Laboratory Manual*, Cold Spring Harbor Laboratories, Cold Spring Harbor, N.Y., 1989. Positive plaques were visualized and purified with goat-anti-mouse alkaline phosphatase. Phagemid from the plaques was rescued and DNA sequence for positive clones was obtained using forward, reverse, and specific internal primers on a Perkin Elmer/Applied Biosystems Inc. Automated Sequencer Model 373A (Foster City, Calif.).

Of the eighteen antigens isolated using this technique, seven (hereinafter referred to as HGE-1, HGE-3, HGE-6, HGE-7, HGE-12, HGE-23 and HGE-24) were found to be related. The determined DNA sequences for HGE-1, HGE-3, HGE-6, HGE-12, HGE-23 and HGE-24 are shown in SEQ ID NO: 1–3 and 5–7, respectively, with the 5' DNA sequence for HGE-7 being provided in SEQ ID NO: 4. The deduced amino acid sequences for HGE-1, HGE-3, HGE-6, HGE-7, HGE-12, HGE-23 and HGE-24 are provided in SEQ ID NO: 8–14, respectively. Comparison of these sequences with known sequences in the gene bank using the DNA STAR system, revealed some degree of homolology to the *Anaplasma marginale* major surface protein.

Of the remaining eleven isolated antigens, no significant homologies were found to HGE-2, HGE-9, HGE- 14, HGE-15, HGE- 16, HGE- 17, HGE- 18 and HGE-25. The determined full-length DNA sequences for HGE-9 and HGE-14 are provided in SEQ ID NO: 16 and 17, respectively, with the determined 5' DNA sequences for HGE-2, HGE-15, HGE-16, HGE-17, HGE-18 and HGE-25 being shown in SEQ ID NO: 15, and 18–22, respectively. The corresponding predicted amino acid sequences for HGE-2, HGE-9, HGE-14 and HGE-18 are provided in SEQ ID NO: 23–26, respectively. The reverse complements of HGE-14, HGE-15 and HGE-18 were found to contain open reading frames which encode the amino acid sequences shown in SEQ ID NO: 27, 28 and 29, respectively. The predicted amino acid sequence from the reverse complement strand of HGE-14 (SEQ ID NO: 27) was found to contain a 41 amino acid repeat, provided in SEQ ID NO: 30.

The determined DNA sequence for the isolated antigen HGE-11 is provided in SEQ ID NO: 31, with the predicted amino acid sequences being provided in SEQ ID NO: 32 and 33. Comparison of these sequences with known sequence in the gene bank, revealed some homology between the amino acid sequence of SEQ ID NO: 32 and that of bacterial DNA-directed RNA polymerase beta subunit rpoB (Monastyrskaya, G. S. et al., 1990*, Bioorg. Khim.* 6:1106–1109), and further between the amino acid sequence of SEQ ID NO: 33 and that of bacterial DNA-directed RNA polymerase beta' subunit rpoC (Borodin A. M. et al, 1988 *Bioorg. Khim.* 14:179–1182).

The determined 5' DNA sequence for the antigen HGE-13 is provided in SEQ ID NO: 34. The opposite strand for HGE-13 was found to contain an open reading frame which encodes the amino acid sequence provided in SEQ ID NO: 35. This sequence was found to have some homology to bacterial 2,3-biphosphoglycerate-independent phosphoglycerate mutase (Leyva-Vazquez, M. A. and Setlow, P., 1994. *J Bacteriol.* 176:3903–3910).

The determined partial nucleotide sequence for the isolated antigen HGE-8 (SEQ ID NO: 36) was found to include, on the reverse complement of the 5' end, two open reading frames encoding the amino acid sequences provided in SEQ ID NO: 37 and 38. The amino acid sequences of SEQ ID NO: 37 and 38 were found to show some homology to prokaryotic and eukaryotic dihydrolipamide succinyltransferase (Fleischmann R. D. et al, 1995 Science 269:496–512) and methionine aminopeptidase (Chang, Y. H., 1992 J Biol. Chem. 267:8007–8011), respectively.

Subsequent studies resulted in the determination of extended DNA sequences for HGE-2, HGE-7, HGE-8, HGE-11, HGE-14, HGE-15, HGE-16, HGE-18, HGE-23 and HGE-25 (SEQ ID NO: 39–48, respectively) and in the determination of the 3' sequence for HGE-17 (SEQ ID NO: 49). The complement of the extended HGE-2 DNA sequence was found to contain an open reading frame which encodes for a 61.4 kDa protein (SEQ ID NO: 50) having three copies of a 125 amino acid repeat (SEQ ID NO: 51). The extended DNA sequence of HGE-7 was found to contain two open reading frames encoding for the amino acid sequences shown in SEQ ID NO: 52 and 53. The extended DNA sequence of HGE-8 was found to contain four open reading frames encoding the proteins of SEQ ID NO: 54–57. Each of these four proteins was found to show some similarity to known proteins, however, to the best of the inventors' knowledge, none have previously been identified in Ehrlichia.

The extended DNA sequence of HGE-11 was found to contain two open reading frames encoding for the amino acid sequences provided in SEQ ID NO: 58 and 59. These two proteins were found to show some homology to the bacterial DNA-directed RNA polymerase beta subunits rpoB and rpo C, respectively. The reverse complement of the extended DNA sequence of HGE-14 was found to contain two open reading frames, with one encoding the amino acid sequence provided in SEQ ID NO: 60. The second open reading frame encodes the amino acid sequence provided in SEQ ID NO: 61, which contains the amino acid sequence provided in SEQ ID NO: 27. The extended DNA sequence of HGE-15 was found to contain two open reading frames encoding for the sequences provided in SEQ ID NO: 62 and 63, with a third open reading frame encoding the sequence of SEQ ID NO: 64 being located on the reverse complement. The extended DNA sequence of HGE-16 was found to contain an open reading frame encoding the amino acid sequence of SEQ ID NO: 65. The reverse complement of the 3' DNA sequence of HGE-17 was found to contain two open reading frames encoding the amino acid sequences of SEQ ID NO: 66 and 67.

The reverse complement of the extended DNA sequence of HGE-18 was found to contain three open reading frames encoding the amino acid sequences of SEQ ID NO: 68–70. The sequence of SEQ ID NO: 70 was found to show some homology to bacterial DNA helicase. The extended DNA sequence of HGE-23 was found to contain two open reading frames encoding for the sequences of SEQ ID NO:71 and 72. Both of these sequences, together with those of SEQ ID NO:52 and 53, were found to share some homology with the *Anaplasma marginale* major surface protein. The predicted amino acid sequence for the extended DNA sequence of HGE-is provided in SEQ ID NO:73. This sequence was found to show some similarity to that of SEQ ID NO:64 (HGE-15). No significant homologies were found to the sequences of HGE-2, HGE-14, HGE-15, HGE-16, HGE-17 and HGE-25 (SEQ ID NO: 50, 60–67 and 73).

EXAMPLE 2

USE OF REPRESENTATIVE ANTIGENS FOR SERODIAGNOSIS OF HGE INFECTION

The diagnostic properties of representative Ehrlichia antigens were determined by Western blot analysis as follows. Antigens were induced as pBluescript SK- constructs (Stratagene), with 2 mM IPTG for three hours (T3), after which the resulting proteins from time 0 (T0) and T3 were separated by SDS-PAGE on 15% gels. Separated proteins were then transferred to nitrocellulose and blocked for 1 hr in 1% BSA in 0.1% Tween 20™/PBS. Blots were then washed 3 times in 0.1% Tween 20™/PBS and incubated with either an HGE patient serum pool (1:200) or an Ehrlichia-infected mouse serum pool for a period of 2 hours. After washing in 0.1% Tween 20™/PBS 3 times, blots were incubated with a second antibody (goat-anti-human IgG conjugated to alkaline phosphatase (AP) or goat-anti-mouse IgG-AP, respectively) for 1 hour. Immunocomplexes were visualized with NBT/BCIP (Gibco BRL) after washing with Tween 20™/PBS three times and AP buffer (100 mM Tris-HCI, 100 mM Na Cl, 5 mM $MgCl_2$, pH 9.5) two times.

As shown in FIG. 1, resulting bands of reactivity with serum antibody were seen at 37 kDa for HGE-1 and HGE-3 for both the mouse serum pool and the human serum pool. Protein size standards, in kDa (Gibco BRL, Gaithersburg, Md.), are shown to the left of the blots.

Western blots were performed on partially purified HGE-1 and HGE-3 recombinant antigen with a series of patient sera from HGE patients, patients with Lyme disease, babesiosis patients or from normal donors. Specifically, purified antigen (4 μg) was separated by SDS-PAGE on 12% gels. Protein was then transferred to nitrocellulose membrane for immunoblot analysis. The membrane was first blocked with PBS containing 1% Tween 20™ for 2 hours. Membranes were then cut into strips and incubated with individual sera (1/500) for two hours. The strips were washed 3 times in PBS/0.1% Tween 20™ containing 0.5 M NaCl prior to incubating with Protein A-horseradish peroxidase conjugate (1/20,000) in PBS/0.1% Tween 20™/0.5 M NaCl for 45 minutes. After further washing three times in PBS/0.1% Tween 20™/0.5 M NaCl, ECL, chemiluminescent substrate (Amersham, Arlington Heights, Ill.) was added for 1 min. Strips were then reassembled and exposed to Hyperfilm ECL (Amersham) for 5–30 seconds.

Figure 2B:
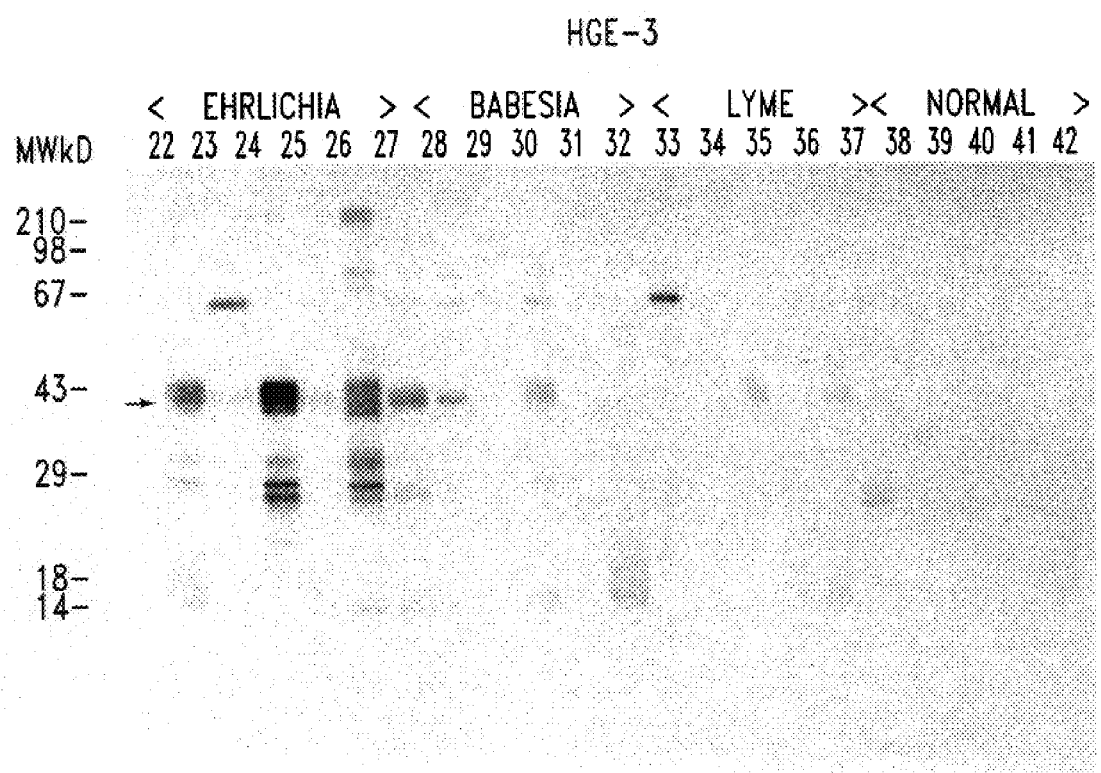

Lanes 1–6 of FIG. 2A show the reactivity of purified recombinant HGE-1 (MW 37 kD) with sera from six HGE-infected patients, of which all were clearly positive. In contrast, no immunoreactivity with HGE-1 was seen with sera from patients with either babesiosis (lanes 7–11), or Lyme disease (lanes 12–16), or with sera from normal individuals (lanes 17–21). As shown in FIG. 2B, HGE-3 (MW 37 kD) was found to react with sera from all six HGE patients (lanes 22–27), while cross-reactivity was seen with sera from two of the five babesiosis patients and weak cross-reactivity was seen with sera from two of the five Lyme disease patients. This apparent cross-reactivity may represent the ability of the antigen HGE-3 to detect low antibody titer in patients co-infected with HGE. No immunoreactivity of HGE-3 was seen with sera from normal patients.

Table 1 provides representative data from studies of the reactivity of HGE-1, HGE-3 and HGE-9 with both IgG and IgM in sera from patients with acute (A) or convalescent (C) HGE, determined as described above. The antibody titer for each patient, as determined by immunofluorescence, is also provided.

TABLE 1

| Patient ID | HGE titer | IgG | | | IgM | | |
|---|---|---|---|---|---|---|---|
| | | HGE-1 | HGE-3 | HGE-9 | HGE-1 | HGE-3 | HGE-9 |
| 1 (A) | 128 | 0.346 | 0.154 | 0.423 | 0.067 | 0.028 | 0.022 |
| 2 (A) | 1024 | 1.539 | 1.839 | 0.893 | 2.75 | 3.256 | 1.795 |
| 3 (A) | <16 | 0.412 | 0.16 | 0.659 | 0.043 | 0.088 | 0.047 |
| 4 (A) | <16 | 0.436 | 0.072 | 0.472 | 0.017 | 0.032 | 0.064 |
| 5 (C) | 256 | 0.322 | 0.595 | 0.694 | 0.229 | 0.345 | 0.269 |
| 6 (A) | 512 | 1.509 | 2.042 | 1.241 | 0.721 | 0.695 | 0.313 |
| 7 (C) | 512 | 0.508 | 1.019 | 0.777 | 0.45 | 0.777 | 0.29 |
| 8 (C) | 128 | 0.635 | 0.979 | 1.684 | 0.729 | 2.079 | 0.729 |
| 9 (C) | 256 | 0.408 | 0.74 | 0.679 | 0.052 | 0.11 | 0.062 |
| 10 (A) | 64 | 0.579 | 0.133 | 0.239 | −0.002 | 0.015 | 0.126 |
| 11 (A) | 256 | 0.13 | 0.066 | 1.002 | −0.018 | 0.003 | 0.047 |
| 12 (A) | 16 | 0.347 | 0.249 | 0.727 | 0.135 | 0.071 | 0.113 |
| 14 (A) | 1024 | 2.39 | 3.456 | 2.635 | 1.395 | 1.52 | 0.55 |

These results indicate that HGE-9 is able to complement the serological reactivity of HGE-1 and HGE-3, leading to increased sensitivity in the serodiagnosis of HGE-infection in convalescent and acute patient sera, as shown, for example, with patients 5, 8, 11 and 12 in Table 1.

EXAMPLE 3

PREPARATION AND CHARACTERIZATION OF EHRLICHIA FUSION PROTEINS

A fusion protein containing the Ehrlichia antigens HGE-9, HGE-3 and HGE-1 is prepared as follows.

Each of the DNA constructs HGE-9, HGE-3 and HGE-1 are modified by PCR in order to facilitate their fusion and the subsequent expression of the fusion protein. HGE-9, HGE-3 and HGE-1 DNA was used to perform PCR using the primers PDM-225 and PDM-226 (SEQ ID NO: 74 and 75), PDM-227 and PDM-228 (SEQ ID NO: 76 and 77), and PDM-229 and PDM-209 (SEQ ID NO: 78 and 79), respectively. In each case, the DNA amplification is performed using 10 μl of 100×Pfu buffer (Stratagene), 1 μl of 12.5 mM dNTPs 2 μl each of the PCR primers at 10 μM concentration, 82 μl water, 2 μl Pfu DNA polymerase (Stratagene, La Jolla, Calif.) and 1 μl DNA at 110 μg/μl. Denaturation at 96° C. is performed for 2 min, followed by 40 cycles of 96° C. for 20 sec, 60° C. for 15 sec and 72° C. for 5 min, and by 72° C. for 5 min.

The HGE-9 PCR fragment is cloned into pPDM HIS at the Eco 72 I sites along with a three-way ligation of HGE-3 or HGE-1 by cutting with Pvu I. HGE-3 is cloned into pPDM HIS which has been cut with Eco 72I/ Xho I. HGE-1 is cloned into pPDM HIS which has been cut with Eco 72I/ Eco RI. PCR is performed on the ligation mix of each fusion with the primers PDM-225, PDM-228 and PDM-209 using the conditions provided above. These PCR products are digested with Eco RI (for HGE-1) or Xho I (for HGE-3) and cloned into pPDM HIS which is digested with Eco RI (or Xho I) and Eco 72I. The fusion construct is confirmed by DNA sequencing.

The expression construct is transformed to BLR pl.ys S *E. coli* (Novagen, Madison, Wis.) and grown overnight in LB broth with kanamycin (30 μg/ml) and chloramphenicol (34 μg/ml). This culture (12 ml) is used to inoculate 500 ml 2XYT with the same antibiotics and the culture is induced with IPTG. Four hours post-induction, the bacteria are harvested and sonicated in 20 mM Tris (8.0), 100 mM NaCl, 0.1 % DOC, followed by centrifugation at 26,000×g. The resulting pellet is resuspended in 8 M urea, 20 mM Tris (8.0), 100 mM NaCl and bound to Ni NTA agarose resin (Qiagen, Chatsworth, Calif.). The column is washed several times with the above buffer then eluted with an imidazole gradient (50 mM, 100 mM, 500 mM imidazole is added to 8 M urea, 20 mM tris (8.0), 100 mM NaCl). The eluates containing the protein of interest are then dialyzed against 10 mM Tris (8.0).

A fusion protein containing the Ehrlichia antigens HGE-3 and HGE- 1, referred to as ErF-1, was prepared as follows.

HGE-3 and HGE-1 DNA was used to perform PCR using the primers PDM-263 and PDM-264 (SEQ ID NO: 80 and 81), and PDM-208 and PDM-265 (SEQ ID NO: 82 and 83), respectively. In both cases, the DNA amplification was performed using 10 μl of 10× Pfii buffer (Stratagene), 1 μl of 10 mM dNTPs, 2 μl each of the PCR primers at 10 μM concentration, 83 μl water, 1.5 μl Pfu DNA polymerase (Stratagene, La Jolla, Calif.) and 1 μl DNA at 50 ng/μl. Denaturation at 96° C. was performed for 2 min, followed by, 40 cycles of 96° C. for 20 sec, 60° C. 15 sec and 72° C. for 3 min and lastly by 72° C. for 4 min. The HG E-3 PCR product was digested with Eco 72I and Xho I, and cloned into pPDM His which had been digested with Eco 72I and Xho I. The IGE-1 PCR product was digested with ScaI. cloned into the above construct at the ScaI site, and screened for orientation. The fusion construct was confirmed by DNA sequencing. The determined DNA sequence of the fusion construct is provided in SEQ ID NO: 84.

The expression construct was transformed into BL21 pLys S *E. coli* (Novagen, Madison, Wis.) and grown overnight in LB broth with kanamycin (30 μg/ml) and chloramphenicol (34 μg/ml). This culture (12 ml) was used to inoculate 500 ml 2XYT with the same antibiotics and the culture was induced with IPTG. Four hours post-induction, the bacteria were harvested and sonicated in 20 mM Tris (8.0), 100 mM NaCl, 0.1% DOC, followed by centrifugation at 26,000×g. The protein came out in the inclusion body pellet. This pellet was washed three times with a 0.5% CHAPS wash in 20 mM Tris (8.0), 300 mM NaCl. The pellet was then solubilized in 6 M GuHCl, 20 mM Tris (9.0), 300 mM NaCl, 1% Triton X-100 and batch bound to Nickel NTA resin (Qiagen). The column was washed with 100 ml 8M urea, 20 mM Tris (9.0), 300 mM NaCl and 1% DOC. This wash was repeated but without DOC. The protein was eluted with 8 M urea, 20 mM Tris (9.0), 100 mM NaCl and 500 mM imidazole. In a second elution, the imidazole was increased to 1 M. The elutions were run on a 4–20% SDS-PAGE gel and the fractions containing the protein of interest were pooled and dialyzed against 10 mM Tris (9.0). The amino acid sequence of the fusion protein ErF-1 is provided in SEQ ID NO: 85.

One of skill in the art will appreciate that the order of the individual antigens within the fusion protein may be changed and that comparable or enhanced activity could be expected provided each of the epitopes is still functionally available. In addition, truncated forms of the proteins containing active epitopes may be used in the construction of fusion proteins.

Table 2 provides representative data from studies of the reactivity of ErF-1, HGE-1 and HGE-3 with both IgG and IgM in sera from patients with acute (A) or convalescent (C) HGE, determined as described above in Example 2. The antibody titer for each patient, as determined by immunofluorescence, is also provided.

TABLE 2

| Patient ID | HGE titer | IgG HGE-1 | IgG HGE-3 | IgG HGE-9 | IgM HGE-1 | IgM HGE-3 | IgM HGE-9 |
|---|---|---|---|---|---|---|---|
| 1 (A) | 128 | 0.346 | 0.154 | 0.114 | 0.067 | 0.028 | 0.149 |
| 2 (A) | 1024 | 1.539 | 1.839 | 1.911 | 2.75 | 3.256 | 1.916 |
| 3 (A) | <16 | 0.412 | 0.16 | 0.096 | 0.043 | 0.088 | 0.104 |
| 4 (A) | <16 | 0.436 | 0.072 | 0.111 | 0.017 | 0.032 | 0.081 |
| 5 (C) | 256 | 0.322 | 0.595 | 0.713 | 0.229 | 0.345 | 0.190 |
| 6 (A) | 512 | 1.509 | 2.042 | 1.945 | 0.721 | 0.695 | 0.314 |
| 7 (C) | 512 | 0.508 | 1.019 | 1.206 | 0.45 | 0.777 | 0.361 |
| 8 (C) | 128 | 0.635 | 0.979 | 1.212 | 0.729 | 2.079 | 0.551 |
| 9 (C) | 256 | 0.408 | 0.74 | 0.767 | 0.052 | 0.11 | 0.157 |
| 10 (A) | 64 | 0.579 | 0.133 | 0.116 | -0.002 | 0.015 | 0.052 |
| 11 (A) | 256 | 0.13 | 0.066 | 0.039 | -0.018 | 0.003 | 0.022 |
| 12 (A) | 16 | 0.347 | 0.249 | 0.063 | 0.135 | 0.071 | 0.032 |
| 14 (A) | 1024 | 2.39 | 3.456 | 2.814 | 1.395 | 1.52 | 0.773 |

EXAMPLE 4

PREPARATION OF SYNTHETIC POLYPEPTIDES

Polypeptides may be synthesized on a Millipore 9050 peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugating or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0–60% acetonitrile (containing 0.1% TFA) in water (containing 0.1% TFA) may be used to elute the peptides. Following lyophilization of the pure fractions, the peptides may be characterized using electrospray mass spectrometry and by amino acid analysis.

Although the present invention has been described in some detail by way of illustration and example for purposes of clarity of understanding, changes and modifications can be carried out without departing from the scope of the invention which is intended to be limited only by the scope of the appended claims.

What is claimed is:

1. An isolated antigenic epitope of an Ehrlichia antigen wherein the epitope comprises an amino acid sequence selected from the group consisting of SEQ ID NO:30 and 51.

2. An isolated polypeptide comprising at least two antigenic epitopes according to claim 1.

3. A pharmaceutical composition comprising at least one antigenic epitope according to claim 1 and a physiologically acceptable carrier.

4. A composition comprising at least one antigenic epitope according to claim 1 and a non-specific immune response enhancer.

5. An isolated polypeptide comprising an immunogenic portion of an Ehrlichia antigen associated with human granulocytic ehrlichiosis.

6. An isolated polypeptidc comprising SEQ ID NO:24.

7. An isolated polypeptide comprising an immunogenic portion of SEQ ID NO:24.

8. An isolated polypeptide comprising an amino acid sequence selected from the group consisting of:

(a) sequences having at least 90% identity to SEQ ID NO:24; and (b) sequences encoded by a DNA sequence selected from the group consisting of: SEQ ID NO: 16 and the complements of SEQ ID NO:16.

9. A pharmaceutical composition comprising at least one polypeptide according to any one of claims 2, and 6–8, and a physiologically acceptable carrier.

10. A composition comprising at least one polypeptide according to any one of claims 2, and 6–8 and a non-specific immune response enhancer.

* * * * *

UNITED STATES PATENT AND TRADEMARK OFFICE
CERTIFICATE OF CORRECTION

PATENT NO. : 6,277,381 B1
DATED : August 21, 2001
INVENTOR(S) : Steven G. Reed et al.

It is certified that error appears in the above-identified patent and that said Letters Patent is hereby corrected as shown below:

Column 153, claim 1,
Line 29, "An isolated antigenic epitopc" should read -- An isolated antigenic epitope --.

Column 154, claim 10,
Line 41, "and 6-8 and" should read -- and 6-8, and --.

Signed and Sealed this

Twenty-sixth Day of February, 2002

Attest:

Attesting Officer

JAMES E. ROGAN
*Director of the United States Patent and Trademark Office*